United States Patent
Galili

(10) Patent No.: US 7,820,628 B2
(45) Date of Patent: Oct. 26, 2010

(54) TUMOR LESION REGRESSION AND CONVERSION IN SITU INTO AUTOLOGOUS TUMOR VACCINES BY COMPOSITIONS THAT RESULT IN ANTI-GAL ANTIBODY BINDING

(75) Inventor: Uri Galili, Shrewsbury, MA (US)

(73) Assignee: University of Massachusetts Medical School, Shrewsbury, MA (US)

( * ) Notice: Subject to any disclaimer, the term of this patent is extended or adjusted under 35 U.S.C. 154(b) by 269 days.

(21) Appl. No.: 11/355,804

(22) Filed: Feb. 16, 2006

(65) Prior Publication Data
US 2006/0251661 A1 Nov. 9, 2006

Related U.S. Application Data

(60) Provisional application No. 60/654,921, filed on Feb. 22, 2005.

(51) Int. Cl.
| A61K 31/70 | (2006.01) |
| A61K 31/715 | (2006.01) |
| C07H 1/00 | (2006.01) |
| C13K 5/00 | (2006.01) |
| C13K 7/00 | (2006.01) |

(52) U.S. Cl. .................. 514/25; 514/61; 536/123.1; 536/123.13

(58) Field of Classification Search .................. None
See application file for complete search history.

(56) References Cited

U.S. PATENT DOCUMENTS

| 5,869,035 | A | 2/1999 | Link, Jr. et al. ............. 424/93.7 |
| 5,879,675 | A | 3/1999 | Galili et al. ................. 424/93.7 |
| 6,361,775 | B1 | 3/2002 | Galili et al. ............... 424/184.1 |
| 6,420,335 | B1 * | 7/2002 | Weichselbaum et al. ........ 514/2 |
| 2002/0041869 | A1 | 4/2002 | Ali et al. .................... 424/93.21 |
| 2004/0191229 | A1 | 9/2004 | Link, Jr. et al. ........... 424/93.21 |
| 2004/0214783 | A1 | 10/2004 | Terman ........................ 514/33 |

OTHER PUBLICATIONS

Galili, U, "Autologous Tumor Vaccines Processed to Express [alpha]-gal Epitopes: A Practical Approach to Immunotherapy in Cancer," Cancer Immunology and Immunotherapy, 53, 635-645 (2004); published online on Jun. 16, 2004.*
Manches et al., "Anti-GAL-mediated Targeting of Human B Lymphoma Cells to Antigen-presenting Cells: A Potential Method for Immunotherapy Using Autologous Tumor Cells," Haematologica, 90(5), 625-634 (2005).*
Galili et al., "Intratumoral Injection of [alpha]-gal Glycolipids Induces Zenograft-Like Destruction and Conversion of Lesions into Endogenous Vaccines," Journal of Immunology, 178, 4626-4687 (2007).*
Beers et al. (eds.), a portion of the Index of The Merck Manual of Diagnosis and Therapy, 17th Edition, Merck & Co., Inc., Rahway, NJ, Jan. 1999, only title pages and text pp. 2769-2770, 2808 & 2823 supplied.*
Buehler et al., "Use of the enzyme-linked immunoadsorbent assay to monitor the purification of glycosphingolipid antigens by high-performance liquid chromatography," Anal Biochem, 164:521-525, 1987 abstract only.
Chen et al., "Synthesis of alpha-gal epitopes (Galalpha1-3Galbeta1-4GlcNAc-R) on human tumor cells by recombinant alpha1,3galactosyltransferase produced in Pichia pastoris," Glycobiology, 11:577-586, 2001.
Chien et al., "Isolation and characterization of a heptaglycosylceramide from bovine erythrocyte membranes," J Lipid Res, 20:669-673, 1979.
Collins et al., "Cardiac xenografts between primate species provide evidence for the importance of the alpha-galactosyl determinant in hyperacute rejection," J Immunol, 154:5500-5510, 1995.
Dabrowski et al., "Immunochemistry of I/i-active oligo- and polyglycosylceramides from rabbit erythrocyte membranes," J Biol Chem, 259:7648-7651, 1984.
Deriy et al., "Expression of alpha-gal epitopes on HeLa cells transduced with adenovirus containing alpha1,3galactosyltransferase cDNA," Glycobiology, 12:135-144, 2002.
Deriy et al., "In vivo targeting of vaccinating tumor cells to antigen-presenting cells by a gene therapy method with adenovirus containing the α1,3galatosyltransferase gene," Cancer Gene Therapy, 12:528-539, 2005.
Dunn et al., "Cancer immunoediting: from immunosurveillance to tumor escape," Nat Immunol, 3:991-998, 2002.
Galili et al., "A unique natural human IgG antibody with anti-alpha-galactosyl specificity," J Exp Med, 160:1519-1531, 1984.
Galili et al., Human natural anti-alpha-galactosyl IgG. II. The specific recognition of alpha (1—3)-linked galactose residues, J Exp Med, 162:573-582, 1985.
Galili et al., "Evolutionary relationship between the natural anti-Gal antibody and the Gal alpha 1—3Gal epitope in primates," Proc Natl Acad Sci USA, 84:1369-1373, 1987.
Galili et al., "Interaction between human natural anti-alpha-galactosyl immunoglobulin G and bacteria of the human flora," Infect Immun, 56:1730-1737, 1988.

(Continued)

Primary Examiner—Lawrence E Crane
(74) Attorney, Agent, or Firm—Medlen & Carroll, LLP

(57) ABSTRACT

The present invention discloses that an intratumoral injection of: i) glycolipids with α-gal epitope; ii) gene vectors comprising an α1,3galactosyltransferase gene; or iii) a mixture of α1,3galactosyltransferase, neuraminidase, and uridine diphosphate galactose results in tumor regression and/or destruction. Binding of the natural anti-Gal antibody to de novo expressed tumoral α-gal epitopes induces inflammation resulting in an anti-Gal antibody mediated opsonization of tumor cells and their uptake by antigen presenting cells. These antigen presenting cells migrate to draining lymph nodes and activate tumor specific T cells thereby converting the treated tumor lesions into in situ autologous tumor vaccines. This therapy can be applied to patients with multiple lesions and in neo-adjuvant therapy to patients before tumor resection. In addition to the regression and/or destruction of the treated tumor, such a vaccine will help in the immune mediated destruction of micrometastases that are not detectable during the removal of the treated tumor.

40 Claims, 38 Drawing Sheets
(8 of 38 Drawing Sheet(s) Filed in Color)

OTHER PUBLICATIONS

Galili et al., "Man, apes, and Old World monkeys differ from other mammals in the expression of alpha-galactosyl epitopes on nucleated cells," *J Biol Chem*, 263:17755-17762, 1988.

Galili et al., "Gene sequences suggest inactivation of alpha-1,3-galactosyltransferase in catarrhines after the divergence of apes from monkeys," *Proc Natl Acad Sci USA*; 88:7401-7404, 1991.

Galili, "Evolution and pathophysiology of the human natural anti-alpha-galactosyl IgG (anti-Gal) antibody," *Springer Semin Immunopathol*. 15:155-171, 1993.

Galili et al., "Suppression of α-galactosyl epitopes synthesis and production of the natural anti-Gal antibody: a major evolutionary event in ancestral Old World primates," *Human Evolution*, 29:433-442, 1995.

Galili, "Autologous tumor vaccines processed to express alpha-gal epitopes: a practical approach to immunotherapy in cancer," *Cancer Immunology Immunotherapy*, 53:935-945, 2004.

Hamadeh et al., "Anti-alpha-galactosyl immunoglobulin A (IgA), IgG, and IgM in human secretions," *Clin Diagnos Lab Immunol*, 2:125-131, 1995.

Honma et al., "Isolation and partial structural characterization of macroglycolipid from rabbit erythrocyte membranes," *J Biochem* (Tokyo). 90:1187-1196, 1981 abstract only.

Kanda et al., "Incorporation of spin-labeled ganglioside analogues into cell and liposomal membranes," *J Biochem* (Tokyo). 91:1707-1718, 1982 abstract only.

Karttunen et al., "Detection of rare antigen-presenting cells by the lacZ T-cell activation assay suggests an expression cloning strategy for T-cell antigens," *Proc Natl Acad Sci USA*, 89:6020-6024, 1992.

LaTemple et al., "Increased immunogenicity of tumor vaccines complexed with anti-Gal: studies in knockout mice for alpha1,3galactosyltransferase," *Cancer Res*, 59:3417-3423, 1999.

Lugade et al., "Local radiation therapy of B16 melanoma tumors increases the generation of tumor antigen-specific effector cells that traffic to the tumor," *J Immunol*, 174:7516-7523, 2005.

Manches et al., "Anti-Gal-mediated targeting of human B lymphoma cells to antigen-presenting cells: a potential method for immunotherapy using autologous tumor cells," *Haematologica*, 90:625-634, 2005.

Marrogi et al., "Study of tumor infiltrating lymphocytes and transforming growth factor-beta as prognostic factors in breast carcinoma," *Int J Cancer*, 74:492-501, 1997.

Naito et al., "CD8+ T cells infiltrated within cancer cell nests as a prognostic factor in human colorectal cancer," *Cancer Res*. 58:3491-3494, 1998.

Nakano et al., "Proliferative activity of intratumoral CD8+ T-lymphocytes as a prognostic factor in human renal cell carcinoma: clinicopathologic demonstration of antitumor immunity," *Cancer Res*, 61:5132-5136, 2001.

Palmetshofer et al., "Alpha-galactosyl epitope-mediated activation of porcine aortic endothelial cells: type I activation," *Transplantation*, 65:844-853, 1998.

Palmetshofer et at, "Alpha-galactosyl epitope-mediated activation of porcine aortic endothelial cells: type II activation," *Transplantation*, 65:971-978, 1998.

Pardoll, "Therapeutic vaccination for cancer," *Clin Immunol*, 95:S44-49, 2000.

Sandrin et al., "Natural human anti-Gal alpha(1,3)Gal antibodies react with human mucin peptides," *Glycoconj J*, 14:97-105, 1997.

Schumacher et al., "Prognostic significance of activated CD8(+) T cell infiltrations within esophageal carcinomas," *Cancer Res*, 61:3932-3936, 2001.

Spiegel et al., "Fluorescent gangliosides as probes for the retention and organization of fibronectin by ganglioside-deficient mouse cells," *J Cell Biol*, 100:721-726, 1985.

Tanemura et al., "Differential immune responses to alpha-gal epitopes on xenografts and allografts: implications for accommodation in xenotransplantation," *J Clin Invest*, 105:301-310, 2000.

Thall et al., "Oocyte Gal alpha 1,3Gal epitopes implicated in sperm adhesion to the zona pellucida glycoprotein ZP3 are not required for fertilization in the mouse," *J Biol Chem*, 270:21437-21440, 1995.

Uemura et al., "Characterization of major glycolipids in bovine erythrocyte membrane," *J Biochem* (Tokyo), 83:463-471, 1978 abstract only.

Zhang et al., "Intratumoral T cells, recurrence, and survival in epithelial ovarian cancer," *N Engl J Med*, 348:203-213, 2003.

Anidjar et al., "Ureteral gene transfer to porcine induced strictures using endourologic delivery of an adenoviral vector," *J Urol*, 161:1636-1643, 1999.

Galili et al., "Intratumoral injection of α-gal glycolipids induces xenograft-like destruction and conversion of lesions in to endogenous vaccines," *J Immunol*, 178: 4676-4687, 2007.

Link et al., "Eliciting hyperacute xenograft response to treat human cancer: alpha(1,3) galactosyltransferase gene therapy," *Anticancer Res*. 18:2301-2308, 1998.

Swisher et al., "Induction of p53-regulated genes and tumor regression in lung cancer patients after intratumoral delivery of adenoviral p53 (INGN 201) and radiation therapy," *Clin Cancer Res*. 9:93-101, 2003.

\* cited by examiner

α-gal EPITOPE
ON CARBOHYDRATE CHAIN
OF GLYCOPROTIENS

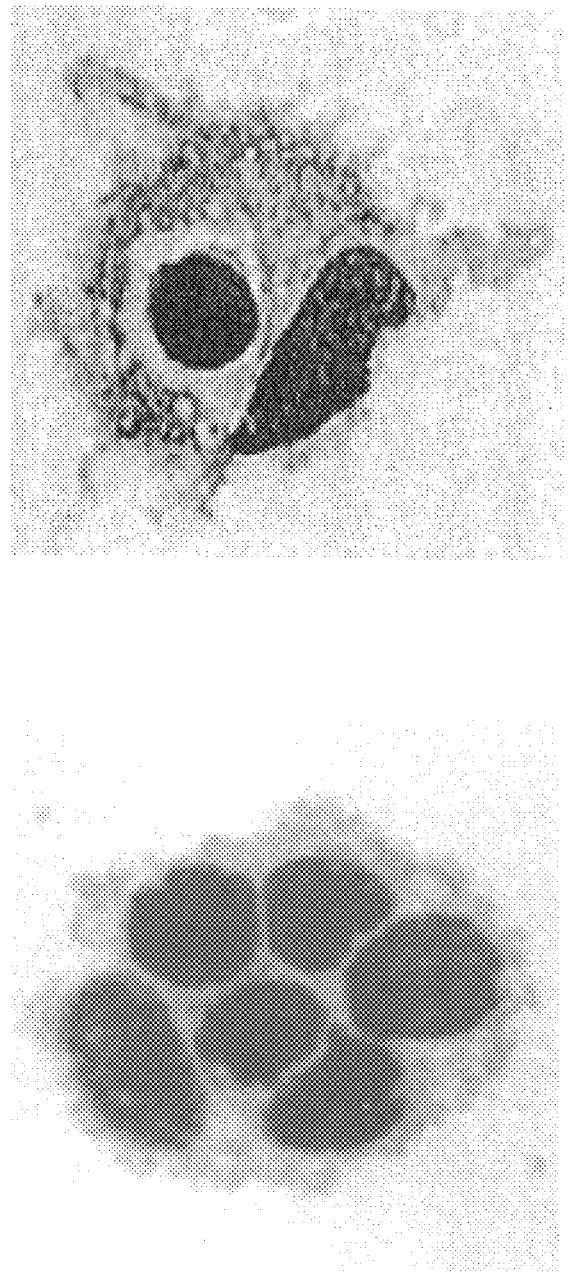

GAGAAAATA ATG AAT GTC AAA GGA AAA GTA ATT CTG TCG ATG CTG GTT     48
         MET Asn Val Lys Gly Lys Val Ile Leu Ser Met Leu Val
         1                   5                   10

GTC TCA ACT GTG ATT GTT TGT GTG TTT TGG GAA TAT ATC CCA AGC GAA    96
Val Ser Thr Val Ile Val Cys Val Phe Trp Glu Tyr Ile Pro Ser Glu
        15                  20                  25

GGC TCT TTC TTG ATA TAT TAT TCA AAG CCT AAC AAA CCA GAT GTT GAC   144
Gly Ser Phe Leu Ile Tyr Tyr Ser Lys Pro Asn Lys Pro Asp Val Asp
    30                  35                  40              45

AGC AGT GCT GCT ATT TGG AAG GAC CAG CTT TAT CAC TTC CCT TGG GGA   192
Ser Ser Ala Ala Ile Trp Lys Asp Gln Leu Tyr His Phe Pro Trp Gly
                50                  55                  60

ATC AGA AAT CAC GAG GAA TAT TAT CAG CAA AAA GAG TTT AAA GAA GGA   240
Ile Arg Asn His Glu Glu Tyr Tyr Gln Gln Lys Glu Phe Lys Glu Gly
        65                  70                  75

AGA GAG GAG AAG AAA CAA AAA AAA GAG GAT GAC ACA ACA GAG AAA CGG   288
Arg Glu Glu Lys Lys Gln Lys Lys Glu Asp Asp Thr Thr Glu Lys Arg
80                  85                  90

TGG GAT TGG AAG CCA CAA GAA AAG AAG GTT ATG ACA CTT CGG GTG ACC   336
Trp Asp Trp Lys Pro Gln Glu Lys Lys Val Met Thr Leu Arg Val Thr
                100                 105                 110

CAA TGG TTT CCG GCG AAT TTT GAA GGC AGG ATC ACA AAA AAA ACC ATC   384
Gln Trp Phe Pro Ala Asn Phe Glu Gly Arg Ile Thr Lys Lys Thr Ile
        115                 120                 125

Mel Asn Val Lys Gly Lys Val Ile Leu Ser Met Leu Val Val Ser Thr
1              5                    10                   15
Val Ile Val Val Phe Trp Glu Tyr Ile Asn Ser Pro Glu Gly Ser Phe
           20                   25                   30
Leu Trp Ile Tyr His Ser Lys Asn Pro Glu Val Asp Asp Ser Ser Ala
           35                   40                   45
Gln Lys Asp Trp Trp Phe Pro Gly Trp Phe Asn Asn Gly Ile His Asn
    50                   55                   60
Tyr Gln Gln Glu Glu Glu Asp Thr Asp Lys Glu Lys Gly Arg Glu Glu
65                   70                   75                   80
Glu Gln Lys Lys Glu Asp Asp Thr Thr Glu Leu Arg Leu Trp Asp Trp
                85                   90                   95
Phe Asn Pro Lys Lys Arg Pro Glu Val Met Thr Val Thr Gln Trp Lys
           100                  105                  110
Ala Pro Val Val Trp Glu Gly Thr Tyr Asn Lys Ala Ile Leu Glu Asn
       115                  120                  125
Tyr Tyr Ala Lys Gln Lys Ile Thr Val Gly Leu Thr Val Phe Ala Ile
    130                  135                  140
Gly Arg Tyr Ile Glu His Tyr Leu Glu Glu Phe Val Thr Ser Ala Asn
145                  150                  155                  160
Arg Tyr Phe Met Val Gly His Lys Val Ile Phe Tyr Val Met Val Asp
                165                  170                  175
Asp Val Ser Lys Ala Pro Phe Ile Glu Leu Gly Pro Leu Arg Ser Phe
                180                  185                  190
Lys Val Phe Glu Val Lys Pro Glu Lys Arg Trp Gln Asp Ile Ser Met
       195                  200                  205
Met Arg Met Lys Thr Ile Gly Glu His Ile Leu Ala His Ile Gln His
    210                  215                  220
Glu Val Asp Phe Leu Phe Cys Met Asp Val Asp Gln Val Phe Gln Asp
225                  230                  235                  240
His Phe Gly Val Glu Thr Leu Gly Gln Ser Val Ala Gln Leu Gln Ala
                245                  250                  255
Trp Trp Tyr Lys Ala Asp Pro Asp Asp Phe Thr Tyr Glu Arg Arg Lys
                260                  265                  270
Glu Ser Ala Ala Tyr Ile Pro Phe Gly Gln Gly Asp Phe Tyr Tyr His
       275                  280                  285
Ala Ala Ile Phe Gly Gly Thr Pro Ile Gln Val Leu Asn Ile Thr Gln
    290                  295                  300
Glu Cys Phe Lys Gly Ile Leu Leu Asp Lys Lys Asn Asp Ile Glu Ala
305                  310                  315                  320
Glu Trp His Asp Glu Ser His Leu Asn Lys Tyr Phe Leu Leu Asn Lys
                325                  330                  335
Pro Ser Lys Ile Leu Ser Pro Glu Tyr Cys Trp Asp Tyr His Ile Gly
       340                  345                  350
Leu Pro Ser Asp Ile Lys Thr Val Lys Leu Ser Trp Gln Thr Lys Glu
    355                  360                  365
Tyr Asn Leu Val Arg Lys Asn Val
370                  375

TUMOR LESION REGRESSION AND CONVERSION IN SITU INTO AUTOLOGOUS TUMOR VACCINES BY COMPOSITIONS THAT RESULT IN ANTI-GAL ANTIBODY BINDING

This application claims the benefit of U.S. Provisional Application No. 60/654,921, filed on Feb. 22, 2005.

FIELD OF INVENTION

The present invention is related to the field of cancer treatment. In one embodiment, the invention contemplates administering compounds to tumor lesions that induce local expression of α-gal epitopes within the tumor. In one embodiment, the administration induces regression and/or destruction of the treated tumor lesions. In another embodiment, the administration converts the treated tumor lesions into an autologous tumor vaccine. In one embodiment, the compounds comprise glycolipids having an α-gal epitope. In another embodiment, the compounds comprise a mixture of α1,3galactosyltransferase, neuraminidase, and uridine diphosphate galactose.

BACKGROUND

The major cause of death in cancer patients with solid tumors is the recurrence of the cancer after surgery as multiple metastases that are nonresectable and/or refractory to any therapy. The majority of these patients are considered to have a terminal cancer disease. As no treatment is available for them, many of these patients die within weeks or few months after detection of metastatic tumor lesions.

Tumors develop in cancer patients because the immune system fails to detect tumor cells as cells that ought to be destroyed. Tumor cells express autologous tumor antigens in a large proportion of cancer patients. These autologous tumor antigens may elicit a protective anti-tumor immune response. Tumor cells, or tumor cell membranes, have to be internalized by antigen presenting cells in order to induce the development of an anti-tumor immune response. However, the immune system in cancer patients displays "ignorance" toward the tumor antigens that is associated with early development of the tumor in a "stealthy" way, so it is "invisible" to antigen presenting cells (Pardoll D M. 2000; *Clin Immunol.* 95:S44-49, and Dunn G P, Bruce A T, Ikeda H, Old L J, Schreiber R D. *Nat Immunol* 2002; 3: 991-8).

In addition, the tumor microenvironment and local cytokine milieu are often suppressive toward immune function and can actively induce immune cell anergy and death (Malmberg K J. *Cancer Immunol Immunother.* 2004; 53: 879-92; Lugade A A, Moran J P, Gerber S A, Rose R C, Frelinger J G, Lord E M. *J Immunol.* 2005; 174: 7516-23). Effective treatment of such metastatic tumor lesions requires two components:
1. Destruction of the lesions that are large enough to be detected visually or by imaging technology, and
2. Induction of a protective anti-tumor immune response against tumor antigens.

Such an immune response results in immune mediated detection, regression, and/or destruction of micrometastases which can not be detected visually and are not detectable by imaging.

Induction of a protective anti-tumor immune response requires uptake of the tumor cells or cell membranes by antigen presenting cells and their transportation to the draining lymph nodes, where the antigen presenting cells process the tumor antigen molecules. The immunogenic tumor antigen peptides are presented by antigen presenting cells in association with class I or class II MHC molecules for the activation of tumor specific $CD8^+$ and $CD4^+$ T cells, respectively. Only after these T cells are activated by the processed and presented tumor antigen peptides, these lymphocytes can leave the lymph nodes, circulate in the body, seek and destroy metastatic tumor cells expressing tumor antigens. In addition, only after they are activated, helper T cells can provide help to B cells for producing antibodies against the tumor antigens. However, since the tumor cells naturally evolve to be "invisible" to antigen presenting cells, the developing tumor metastases are usually ignored by the immune system to the extent that metastasizing tumor cells can proliferate even within lymph nodes. Therefore, eliciting an effective anti-tumor immune response requires effective targeting of tumor cells to antigen presenting cells.

What is needed in the art are compositions and methods to non-surgically introduce compounds into a solid tumor under conditions such that a naturally occurring antibody will interact with the introduced compound. Such interaction will induce local inflammation for the regression and/or destruction of the tumor and the targeting tumor cells and/or tumor cell membranes to antigen presenting cells. This process elicits a protective immune response in the host against tumor antigens on tumor cells in micrometastases that can not be detected visually or by imaging and therefore can not be removed by resection.

SUMMARY OF THE INVENTION

The present invention is related to the field of cancer treatment. In one embodiment, the invention contemplates administering compounds to tumor lesions that induce local expression of α-gal epitopes within the tumor. In one embodiment, the administration induces regression and/or destruction of the treated tumor lesions. In another embodiment, the administration converts the treated tumor lesions into an autologous tumor vaccine. In one embodiment, the compounds comprise glycolipids having an α-gal epitope. In another embodiment, the compounds comprise a mixture of α1,3galactosyltransferase, neuraminidase, and uridine diphosphate galactose.

In one embodiment, the present invention contemplates a method, comprising: a) providing: i) a subject having endogenous anti-Gal antibody and at least one solid tumor comprising a plurality of tumor cells; and ii) a glycolipid preparation comprising an α-gal epitope having a terminal Galα1-3Gal; and b) introducing said glycolipid preparation into at least one solid tumor to create a treated solid tumor. In one embodiment, the method further comprises displaying a membrane-bound α-gal epitope on said tumor cell. In one embodiment, the method further comprises inducing an intratumoral inflammation. In one embodiment, the introducing comprises a procedure including, but not limited to, injection, imaging guided injection, endoscopy, bronchoscopy, cystoscopy, colonoscopy, laparoscopy, and catheterization. In one embodiment, the solid tumor is a tumor originating from an organ including, but not limited to, peritoneum, liver, pancreas, lung, urinary bladder, prostate, uterus, cervix, vagina, breast, skin, brain, lymph node, head and neck, stomach, intestine, colon, and ovaries. In one embodiment, the subject was treated previously to surgically remove said tumor. In one embodiment, the subject was not treated to remove said tumor. In one embodiment, the tumor comprises a primary tumor. In one embodiment, the method further comprises converting said treated solid tumor into an autologous vaccine. In one embodiment, the glycolipid preparation is derived from a source selected from the group consisting of rabbit red blood cells, bovine red blood cells, and any other mammalian cell. In one embodiment, the tumor is melanoma. In one embodiment, the introducing is selected from the group including, but not limited to, intradermal injection, topical ointment, topical lotion, and topical solution. In one embodiment, the treated solid tumor undergoes regression. In one embodiment, the treated solid tumor is destroyed. In one embodiment, the glycolipid is an isolated glycolipid.

In one embodiment, the present invention contemplates a method of treating a human, comprising: a) providing: i) a human having endogenous anti-Gal antibody and a plurality of nonresectable solid tumors having a membrane, wherein at least a subset of said nonresectable solid tumors is accessible via a procedure selected from the group consisting of endoscopy, bronchoscopy, cystoscopy, colonoscopy, laparoscopy, and catheterization, ii) an aqueous glycolipid preparation comprising an galactosyl epitope, wherein said preparation comprises glycolipid micelles; and b) intratumorally injecting said preparation using said procedure. In one embodiment, the galactosyl epitope becomes opsonized. In one embodiment, the opsonized galactosyl epitope induces an antigen presenting cell to produce an autologous vaccine against said solid tumor.

In one embodiment, the present invention contemplates a method, comprising: a) providing: i) a subject having endogenous anti-Gal antibody and at least one solid tumor comprising a plurality of tumor cells; and ii) a glycoconjugate preparation comprising α-gal epitope having a terminal Galα1-3Gal; and b) introducing said glycoconjugate preparation into said at least one solid tumor to create a treated solid tumor. In one embodiment, the method further comprises displaying a membrane-bound α-gal epitope on said tumor cell. In one embodiment, the method further comprises an intratumoral inflammation. In one embodiment, the introducing comprises a procedure including, but not limited to, injection, imaging guided injection, endoscopy, bronchoscopy, cystoscopy, colonoscopy, laparoscopy, and catheterization. In one embodiment, the solid tumor is a tumor originating from an organ including, but not limited to, peritoneum, liver, pancreas, lung, urinary bladder, prostate, uterus, cervix, vagina, breast, skin, brain, lymph node, head and neck, stomach, intestine, colon, and ovaries. In one embodiment, the subject was treated previously to surgically remove said tumor. In one embodiment, the subject was not treated to remove said tumor. In one embodiment, the tumor is a primary tumor. In one embodiment, the method further comprises converting said treated solid tumor into an autologous vaccine. In one embodiment, the tumor is melanoma. In one embodiment, the introducing is selected from the group including, but not limited to, intradermal injection, topical ointment, topical lotion, and topical solution. In one embodiment, the treated solid tumor undergoes regression. In one embodiment, the treated solid tumor is destroyed. In one embodiment, the glycoconjugate is an isolated glycoconjugate.

In one embodiment, the present invention contemplates a method, comprising: a) providing: i) a subject having endogenous anti-Gal antibody and at least one solid tumor comprising a plurality of tumor cells; and ii) a molecule comprising an epitope capable of binding a natural anti-Gal antibody; and b) introducing said molecules into said at least one solid tumor to create a treated solid tumor. In one embodiment, the method further comprises inducing an intratumoral inflammation within said tumor. In one embodiment, the method further comprises displaying a membrane-bound anti-Gal binding molecule. In one embodiment, the introducing comprises a procedure including, but not limited to, injection, imaging guided injection, endoscopy, bronchoscopy, cystoscopy, colonoscopy, laparoscopy, and catheterization. In one embodiment, the solid tumor is a tumor originating from an organ including, but not limited to, peritoneum, liver, pancreas, lung, urinary bladder, prostate, uterus, cervix, vagina, breast, skin, brain, lymph node, head and neck, stomach, intestine, colon, and ovaries. In one embodiment, the subject was treated previously to surgically remove a primary tumor. In one embodiment, the subject was not treated to remove said tumor. In one embodiment, the tumor is a primary tumor. In one embodiment, the method further comprises converting said treated solid tumor into an autologous vaccine. In one embodiment, the solid tumor is melanoma. In one embodiment, the introducing is selected from the group consisting of intradermal injection, topical ointment, topical lotion, topical powder, and topical solution. In one embodiment, the treated solid tumor undergoes regression. In one embodiment, the treated solid tumor is destroyed. In one embodiment, the molecule is an isolated molecule.

In one embodiment, the present invention contemplates a method, comprising: a) providing: i) a subject having endogenous anti-Gal antibody and at least one solid tumor comprising a plurality of tumor cells; and ii) a gene therapy vector comprising a polynucleotide sequence encoding a galactosyl transferase capable of synthesizing an α-gal epitope having a terminal Galα1-3Gal; and b) introducing said gene therapy vector into said at least one solid tumor to create a treated solid tumor. In one embodiment, the method further comprises displaying a membrane bound galactosyl epitope on said tumor cell. In one embodiment, the introducing comprises a procedure including, but not limited to, injection, imaging guided injection, endoscopy, bronchoscopy, cystoscopy, colonoscopy, laparoscopy, gene gun, and catheterization. In one embodiment, the polynucleotide sequence encodes a murine α1,3 galactosyl transferase. In one embodiment, the gene therapy vector is selected from the group consisting of an adenoviral vector, a RNA viral vector, and a DNA viral vector. In one embodiment, the solid tumor is a tumor originating from an organ including, but not limited to peritoneum, liver, pancreas, lung, urinary bladder, prostate, uterus, cervix, vagina, breast, skin, brain, lymph node, head and neck, stomach, intestine, colon, and ovaries. In one embodiment, the subject was treated previously to surgically remove a primary tumor. In one embodiment, the tumor is a primary tumor. In one embodiment, the method further comprises converting said treated solid tumor into an autologous vaccine.

In one embodiment, the present invention contemplates a method, comprising: a) providing: i) a subject having endogenous anti-Gal antibody and at least one solid tumor comprising a plurality of tumor cells; and ii) a solution comprising α1,3galactosyltransferase, neuraminidase, and uridine diphosphate galactose, and b) introducing said solution into said at least one solid tumor to create a treated solid tumor. In one embodiment, the method further comprises displaying a membrane bound α-gal epitope on said tumor cell. In one embodiment, the introducing comprises a procedure including, but not limited to, injection, imaging guided injection, endoscopy, bronchoscopy, cystoscopy, colonoscopy, laparoscopy, gene gun and catheterization. In one embodiment, the α1,3 galactosyltransferase is a recombinant enzyme. In one embodiment, the neuraminidase is derived from *Vibrio Cholera*. In one embodiment, the solid tumor is a tumor originating from an organ including, but not limited to, peritoneum, liver, pancreas, lung, urinary bladder, prostate, uterus, cervix, vagina, breast, skin, brain, lymph node, head and neck, stomach, intestine, colon, and ovaries. In one embodiment, the subject was treated previously to surgically remove a primary tumor. In one embodiment, the tumor is a primary tumor. In one embodiment, the method further comprises converting said treated solid tumor into an autologous vaccine. In one embodiment, the introducing is selected from the group including, but not limited to, intradermal injection, topical ointment, topical lotion, and topical solution.

In one embodiment, the invention contemplates administering compounds having α-gal epitopes (i.e., for example, Galα1-3Galβ1-4GlcNAc-R or Galα1-3Galβ1-3GlcNAc-R or any carbohydrate chain with terminal Galα1-3Gal at the non-reducing end) into tumor lesions thereby inducing expression and/or display of α-gal epitopes on tumor cells within the treated lesion. In one embodiment, the compounds comprise a glycolipid. In another embodiment, the compounds comprise a gene therapy vector that induces expression of α-gal epitopes on the tumor cells.

In one embodiment, the present invention contemplates a method of treating a human, comprising: a) providing; i) a human having endogenous anti-Gal antibody and a plurality of solid tumors; and ii) a glycolipid preparation comprising α-gal epitopes; and b) introducing said glycolipid preparation into at least one solid tumor to create a treated solid tumor, thereby inducing an inflammation within the treated tumor lesion. In one embodiment, introducing the glycolipid preparation displays a membrane-bound α-gal epitope capable of binding to said anti-Gal antibody. In one embodiment, the introducing comprises a procedure selected from the group including, but not limited to, direct intratumoral injection by endoscopy, bronchoscopy, cystoscopy, colonoscopy, laparoscopy, and catheterization; or topically applied as an ointment, lotion, solution or powder. In one embodiment, the solid tumor is a tumor metastasis in an organ selected from the group including, but not limited to, peritoneum, liver, pancreas, lung, urinary bladder, prostate, uterus, cervix, vagina, breast, skin, brain, lymph node, head and neck, stomach, intestine, colon, or ovaries. In one embodiment, the human was treated before a surgical removal of a primary tumor. In one embodiment, the treated tumor is a primary tumor originating from an organ including, but not limited to, peritoneum, liver, pancreas, lung, urinary bladder, prostate, uterus, cervix, vagina, breast, skin, brain, lymph node, head and neck, stomach, intestine, colon, or ovaries. In one embodiment, the α-gal epitope is displayed and a protective anti-tumor immune response is generated (i.e., for example, an autologous in situ vaccination). In one embodiment, the treated solid tumor is at least partially diminished in size (i.e., for example, regression). Although it is not necessary to understand the mechanism of an invention, it is believed that such regression may be due to intratumoral inflammation induced by interaction between the natural anti-Gal antibody and α-gal epitopes in the treated tumor lesions. In one embodiment, the glycolipid preparation is derived from rabbit red blood cells. In another embodiment, the glycolipid preparation is derived from bovine red blood cells, or any other cell. In one embodiment, the glycolipid preparation comprises at least one synthetic glycolipid comprising a carbohydrate chain with a terminal group including, but not limited to, a terminal α-Gal (α-galactosyl), a terminal Galα1-3Gal, a terminal Galα1-6Gal, a terminal Galα1-3Galβ1-4GlcNAc, or a terminal Galα1-3Galβ1-3GlcNAc that may be linked to an anchor group selected from the group comprising a fatty acid, a sphingosine, a ceramide, or any other synthetic or natural molecule that is capable of anchoring an α-gal epitope to a cell membrane. In one embodiment, the glycolipid preparation administered into the tumor includes any molecule or epitope (i.e. part of a molecule capable of interacting with a specific antibody) that is capable of binding the natural anti-Gal antibody (i.e., for example, an anti-Gal binding epitope).

In one embodiment, the present invention contemplates a method of treating a human, comprising: a) providing; i) a human having endogenous anti-Gal antibody and a plurality of solid tumors, and ii) a synthetic or natural glycoconjugate preparation comprising a binding site including, but not limited to, an α-gal epitope, an anti-Gal binding epitope, or a conjugate linker (i.e., for example, succinimide, polylysine, fatty acid lipids etc.) comprising at least one peptide capable of binding to the anti-Gal antibody; and b) introducing said conjugate preparation into at least one solid tumor to create a treated solid tumor, whereby the tumor cells display a membrane-bound epitope capable of binding said anti-Gal antibody.

In one embodiment, the present invention contemplates a method of treating a human, comprising: a) providing; i) a human having endogenous anti-Gal antibody and a plurality of solid tumors, wherein at least a subset of the solid tumors are accessible via a procedure selected from the group including, but not limited to, direct intratumoral injection, injection by a procedure including, but not limited to, endoscopy, bronchoscopy, cystoscopy, colonoscopy, laparoscopy, and catheterization; or topically applied as an ointment, lotion, solution or powder; and ii) a preparation comprising an anti-Gal binding epitope including, but not limited to, an α-gal glycolipid, or any epitope capable of binding the natural anti-Gal antibody, wherein the anti-Gal binding epitope becomes linked to a cell membrane by a chemically reactive group or by a membrane anchoring molecule (i.e., for example, a fatty acid lipid); and b) introducing the preparation into at least one of the solid tumor subset via the procedure to create a treated solid tumor, thereby inducing inflammation in the treated tumor. In one embodiment, the preparation introduction further comprises displaying a membrane-bound anti-Gal binding epitope.

In one embodiment, the present invention contemplates a method comprising an intratumoral injection of a gene therapy vector comprising a α1,3galactosyltransferase gene. In one embodiment, the vector includes, but is not limited to, a viral vector, a DNA vector, or an RNA vector. Although it is not necessary to understand the mechanism of an invention, it is believed that vector insertion and replication of the α1,3-galactosyltransferase gene leads to the synthesis of α-gal epitopes. It is also believed that the binding of anti-Gal to these de novo α-gal epitopes will enable the achievement of the above two goals of lesion regression and conversion of the treated lesion into an in situ autologous tumor vaccine.

One embodiment of the present invention contemplates a method of treating a human, comprising: a) providing; i) a human having endogenous anti-Gal antibody and a single or plurality of solid tumors, wherein at least a subset of said solid tumors are accessible via a procedure selected from the group including, but not limited to, a direct intratumoral injection, or injection by endoscopy, bronchoscopy, cystoscopy, colonoscopy, laparoscopy, and catheterization; and ii) a viral vector comprising a polynucleotide sequence encoding a galactosyltransferase; and b) introducing said viral vector into at least one nonresectable or resectable solid tumor of said subset via said procedure to create a treated solid tumor, wherein said sequence encoding said galactosyltransferase is expressed, whereby the expression creates a galactosyl epitope capable of binding to said anti-Gal antibody. In one embodiment, the polynucleotide sequence encodes murine α1,3galactosyltransferase. In one embodiment, the polynucleotide sequence encodes nonmutated or mutated mammalian α1,3galactosyltransferase. In one embodiment, the polynucleotide sequence encodes nonmutated or mutated vertebrate α1,3galactosyltransferase. In one embodiment, the viral vector comprises an adenoviral vector. In one embodiment, the viral vector comprises a vector selected from the group consisting of a retrovirus vector, an adeno-associated virus vector, a herpes virus vector, an Epstein-Barr virus vector, a lentivirus vector, a vaccinia virus vector. In one embodiment, the vector comprises a naked DNA vector or a naked RNA vector. In one embodiment, the nonresectable solid tumor is a tumor metastasis in an organ selected from the group including, but not limited to, peritoneum, liver, pancreas, lung, urinary bladder, prostate, uterus, cervix, vagina, breast, skin, brain, lymph node, head and neck, stomach, intestine, colon, and ovaries. In one embodiment, the human was treated previously to surgically remove a primary tumor. In one embodiment, the treated tumor comprises a primary tumor. In one embodiment, the treated solid tumor is at least partially diminished in size by the anti-Gal induced inflammation (i.e., for example, regression). In one embodiment, the α-gal epitopes are expressed on cells, and a protective anti-tumor immune response is generated (i.e., for example, an autologous vaccination). In one embodiment, the viral vector has been purified from cells and is substantially cell-free.

In one embodiment, the present invention contemplates a method of treating a human, comprising: a) providing: i) a human having endogenous anti-Gal antibody and a plurality of nonresectable solid tumors, wherein at least a subset of said nonresectable solid tumors is accessible via a procedure selected from the group consisting of endoscopy, bronchoscopy, cystoscopy, colonoscopy, laparoscopy, and catheterization, ii) a viral vector comprising a polynucleotide sequence encoding a galactosyltransferase; and b) introducing said viral vector into at least one nonresectable solid tumor of said subset via said procedure to create a treated nonresectable solid tumor, wherein said sequence encoding said galactosyl transferase is expressed, whereby the expression creates a galactosyl epitope capable of binding to said anti-Gal antibody. In one embodiment, the polynucleotide sequence is murine alpha. 1,3 galactosyl transferase. In one embodiment, the viral vector comprises an adenoviral vector. In one embodiment, the nonresectable solid tumor is a tumor metastasis in an organ selected from the group consisting of liver, colon, and ovaries. In one embodiment, the human was treated previously to surgically remove a primary tumor. In one embodiment, the treated nonresectable solid tumor is at least partially diminished in size.

In one embodiment, the present invention contemplates a method of treating a human, comprising: a) providing: i) a human having endogenous anti-Gal antibody and a plurality of nonresectable solid tumors, wherein at least a subset of said nonresectable solid tumors is accessible via a procedure selected from the group consisting of endoscopy, bronchoscopy, cystoscopy, colonoscopy, laparoscopy, and catheterization, ii) a viral vector comprising a polynucleotide sequence encoding a galactosyl transferase; and b) introducing said viral vector into fewer than all nonresectable solid tumors of said subset via said procedure to create untreated and treated nonresectable solid tumors, wherein said sequence encoding said galactosyl transferase is expressed, whereby the expression creates a galactosyl epitope capable of binding to said anti-Gal antibody. In one embodiment, the polynucleotide sequence is murine alpha. 1,3 galactosyl transferase. In one embodiment, the viral vector comprises an adenoviral vector. In one embodiment, the nonresectable solid tumor is a tumor metastasis in an organ selected from the group consisting of liver, colon, and ovaries. In one embodiment, the human was treated previously to surgically remove a primary tumor. In one embodiment, the growth of at least one of said untreated nonresectable solid tumors is reduced.

In one embodiment, the present invention contemplates a method of treating a human, comprising: a) providing: i) a human having endogenous anti-Gal antibody and a plurality of solid tumor metastases, wherein at least a subset of said metastases is accessible through the skin, ii) a viral vector comprising a polynucleotide sequence encoding a galactosyl transferase; and b) introducing said viral vector into at least one of said metastases of said subset to create a treated metastasis, wherein said sequence encoding said galactosyl transferase is expressed, whereby the expression creates a galactosyl epitope capable of binding to said anti-Gal antibody. In one embodiment, the polynucleotide sequence is murine alpha. 1,3 galactosyl transferase. In one embodiment, the viral vector comprises an adenoviral vector. In one embodiment, the metastases comprise melanoma. In one embodiment, the human was treated previously to surgically remove a primary tumor.

In one embodiment, the present invention contemplates a method of treating a human, comprising: a) providing; i) a human having endogenous anti-Gal antibody and a plurality of solid tumors; and ii) a solution comprising α1,3galactosyltransferase, neuraminidase, and uridine diphosphate galactose; and b) introducing the solution into at least one solid tumor to create a treated solid tumor. In one embodiment, the solid tumor is a tumor metastasis in an organ including, but not limited to, liver, pancreas, lung, urinary bladder, prostate, uterus, cervix, vagina, breast, skin, brain, lymph node, head and neck, stomach, intestine, colon, or ovaries. In one embodiment, the human was treated before a surgical removal of a primary tumor. In one embodiment, the treated tumor is a primary tumor originating from an organ including, but not limited to, liver, pancreas, lung, urinary bladder, prostate, uterus, cervix, vagina, breast, skin, brain, lymph node, head and neck, stomach, intestine, colon, or ovaries. In one embodiment, the α-gal epitope is displayed and a protective anti-tumor immune response is generated (i.e., for example, an autologous vaccination).

Although it is not necessary to understand the mechanism of an invention, it is believed that the combined catalytic activity of α1,3galactosyltransferase and neuraminidase results in synthesis of α-gal epitopes on the tumor cells. It is further believed that the binding of anti-Gal antibody to these de novo α-gal epitopes results in tumor lesion regression and/or destruction and conversion of the treated lesion into an in situ autologous tumor vaccine.

Definitions

The term "α-gal epitopes", as used herein, refers to any molecule, or part of a molecule, with a terminal structure comprising Galα1-3Galβ1-4GlcNAc-R, Galα1-3Galβ1-3GlcNAc-R, or any carbohydrate chain with terminal Galα1-3Gal at the non-reducing end.

The term "glycolipids", as used herein, refers to any molecule with at least one carbohydrate chain linked to a ceramide, a fatty acid chain, or any other lipid. Alternatively, a glycolipid maybe referred to as a glycosphingolipid.

The term "α1,3galactosyltransferase" as used herein, refers to any enzyme capable of synthesizing α-gal epitopes.

The term "anti-Gal binding epitope", as used herein, refers to any molecule or part of molecule that is capable of binding in vivo the natural anti-Gal antibody.

The term "nonresectable", as used herein, refers to any part of an organ or bodily structure that cannot be surgically removed. For example, a "nonresectable tumor" may be a tumor physically unreachable by conventional surgical techniques or a tumor where its removal does not improve the overall cancer disease of the patient.

The term "membrane-bound", as used herein, refers to any molecule that is stably attached to, or embedded within, a phospholipid bilayer. Such attaching or embedding may involve forces including, but not limited to, ionic bonds, covalent bonds, hydrophobic forces, or Van der Waals forces etc. For example, a protein comprising a hydrophobic amino acid region may insert itself into a phospholipid bilayer membrane, or a molecule that contains a lipid tail can insert itself into the phospholipid bilayer of cells and become embedded.

The term "subset", as used herein, refers to a specialized group lower in number than the whole group. For example, a patient may present with a plurality of nonresectable solid tumors. Of this plurality, a subset may be accessible by non-surgical techniques whereas another subset may not be accessible by non-surgical techniques.

The term "accessible", as used herein, refers to any ability to treat a solid tumor by non-surgical techniques. Such techniques may include, but are not limited to, injection into the skin or injection via endoscopy, bronchoscopy, cystoscopy, colonoscopy, laparoscopy, catheterization, or topical application by a lotion, ointment or powder. For example, an ovarian solid tumor may be accessible by laparoscopy. In another example, a colon solid tumor may be accessible by colonoscopy.

The term "introducing", as used herein, refers to any method of transferring a compound into a tissue and subsequently into cells within said tissue. Such methods of introduction may include, but are not limited to, viral vectors, retroviral vectors, adenoviral vectors, biobalistics, lipofection, and many commercially available DNA vectors known in the art. Alternatively, a compound may be placed adjacent to a cell such that the compound is incorporated into the cell by physiological mechanisms (i.e., for example, hydrophobic interactions or active transport). One method of introduction comprises injection, wherein a compound is placed directly into the intercellular space within the injected tissue. Such an injection may be possible when an organ part, growth (i.e., for example, a solid tumor), or bodily cavity is "accessible".

The term "into", as used herein, refers to the successful penetration of a molecule through or within a cell membrane. For example, a viral vector may be introduced into a solid tumor cell under conditions such that the tumor cell is transfected. In another example, a glycolipid may be introduced into a solid tumor cell under conditions such that the glycolipid becomes inserted into the cell's phospholipid bilayer membrane.

The term "regression", "is at least partially diminished in size" or "reduced", as used herein, refers to a diminution of a bodily growth, such as, for example, a solid tumor. Such a diminution may be determined by a reduction in measured parameters such as, but not limited to, diameter, mass (i.e., weight), or volume. The diminution by no means indicates that the size is completely reduced, only that a measured parameter is quantitatively less than a previous determination.

The term "destruction", as used herein, refers to the complete cellular breakdown of a bodily growth, such as, for example, a solid tumor. Such a destruction may involve intracellular apoptosis and/or macrophage phagocytosis such that the bodily growth is completely digested and eliminated from the body.

The term "fewer than all", as used herein, refers to a subset of a group. In the context of one embodiment of the present invention, treatment of fewer than all of the tumors in a patient is contemplated. In other words, in one embodiment, it is not necessary to treat every tumor by introduction of the $\alpha$-gal epitope (e.g. by introduction of glycolipid(s) having a terminal Gal$\alpha$1-3Gal epitope); rather, introduction to a subset results in an immune response to all tumors (including those not directly treated). In this manner, one can achieve a collective diminution of a plurality of bodily growths, such as, for example, solid tumor metastases. Such a diminution may be determined by a reduction in measured parameters such as, but not limited to, number. The diminution by no means indicates that the parameter is reduced to zero, only that a measured parameter is quantitatively less that a previous determination.

The term "growth", as used herein, refers to any tissue or organ that comprises a cellular mass considered to represent an abnormal proliferation. Such growths may be cancerous, non-cancerous, malignant, or non-malignant. If a growth comprises cancer, it may be a tumor. Such tumors may be solid or non-solid.

The term "accessible through the skin", as used herein, refers to any non-surgical technique that is capable of reaching an internal organ or body cavity. Such non-surgical techniques do not require conventional open site surgery comprising a scalpel incision. Non-surgical techniques include, but are not limited to, percutaneous access, or bodily orifice access to internal organs or body cavities. For example, percutaneous access may include, but is not limited to, laparoscopy and catheterization. In another example, bodily orifice access, may include, but is not limited to, endoscopy, bronchoscopy, cystoscopy, and colonoscopy.

The term "subject", as used herein, refers to any organism that is capable of developing a solid tumor. Such organisms include, but are not limited to, human, dog, cat, horse, cow, sheep, goat, mouse, rat, guinea pig, monkey, avian, reptiles etc.

The term "liposome-free", as used herein, refers to any composition, mixture, or solution that does not contain sufficient lipids (i.e., for example, phospholipids) to attain a critical micellular concentration (CMC). Lipids, in fact, may be present but not at concentrations such that liposomes may form.

The term "isolated", as used herein, refers to any composition or mixture that has undergone a laboratory purification procedure including, but not limited to, extraction, centrifugation, chromatographic separation (i.e., for example, thin layer chromatography or high performance liquid chromatography). Usually such a purification procedures provides an isolated composition or mixture based upon physical, chemical, or electrical potential properties. Depending upon the choice of procedure an isolated composition or mixture may contain other compositions, compounds or mixtures having similar chemical properties. For example, an isolated composition or mixture may contain between 1-20%, preferably, 1-10%, but more preferably 1-5% of compositions or mixtures having similar chemical properties. In one embodiment, an isolated composition or mixture comprises a mixture of glycolipids free of cholesterol and phospholipids. In one embodiment, an isolated composition or mixture comprises glycolipids having from between 5-15 glycosidic linkages.

The term "molecule", as used herein, refers to the smallest particle of a composition that retains all the properties of the composition and is composed of one or more atoms. These one or more atoms are arranged such that the molecule may interact (i.e., ionically, covalently, non-covalently etc) with other molecules to form attachments and/or associations. For example, a molecule may have one or more atoms arranged to provide a capability for an interation with an anti-Gal antibody.

BRIEF DESCRIPTION OF THE FIGURES

The file of this patent contains at least one drawing executed in color. Copies of this patent with color drawings will be provided by the Patent and Trademark Office upon request and payment of the necessary fee.

The following are illustrations of the present invention and are not intended as limiting in any manner.

Panel A: CPH is illustrated as a schematic glycolipid molecule with 5 carbohydrate chains. The α-gal epitope (Galα-1-3Galβ1-4GlcNAc-R) is marked within the broken line squares in the schematic structure. The terminal α-galactosyl (Gal) is linked α1,3 to the penultimate Gal of the carbohydrate chain by the glycosylation enzyme α1,3galactosyltransferase. The carbohydrate chain of the glycolipid is linked to the lipid portion (i.e. the ceramide) comprising the two fatty acid chains. An anti-Gal antibody binding to the α-gal epitope is presented as representative of binding to an anti-Gal binding epitope.

Panel B. CPH is illustrated as a space filling model of CPH based on calculated minimum energy conformation. Green-carbon; red-hydroxyls; blue-nitrogen; white-hydrogen. Structure modified from Teneberg et al. *Glycobiology* 1996; 6: 599-609.

Panel C. One embodiment is described of the structure of α-gal epitope on carbohydrate chains of cell surface glycoproteins. The carbohydrate chain is linked to the protein through asparagine (Asn or N) at the bottom of the panel.

Figure 2:
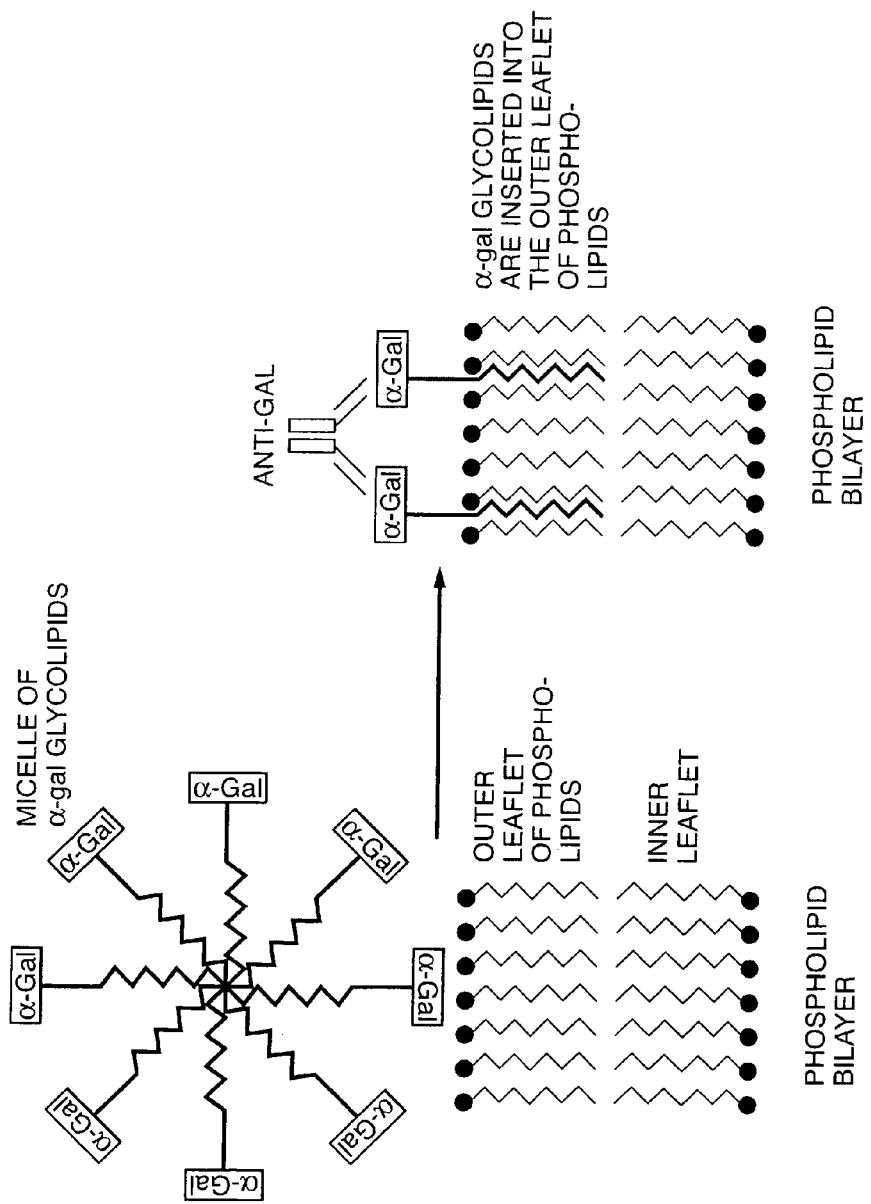

FIG. 2 illustrates one embodiment of the insertion process of α-gal glycolipids into the lipid bilayer of tumor cell membranes.

Panel A. A micelle comprising α-gal glycolipids is shown where the hydrophobic (lipophilic) ceramide chains are clustered in the core adjacent to a phospholipid bilayer membrane.

Panel B. A phospholipid bilayer membrane where individual α-gal glycolipid molecules have inserted themselves into the outer leaflet of the phospholipid bilayer from the adjacent micelle depicted in Panel A. Insertion occurs because the ceramide tail of α-gal glycolipids is in a more stable energetic state when surrounded by the phospholipids of the outer leaflet of cells.

Figure 3A:
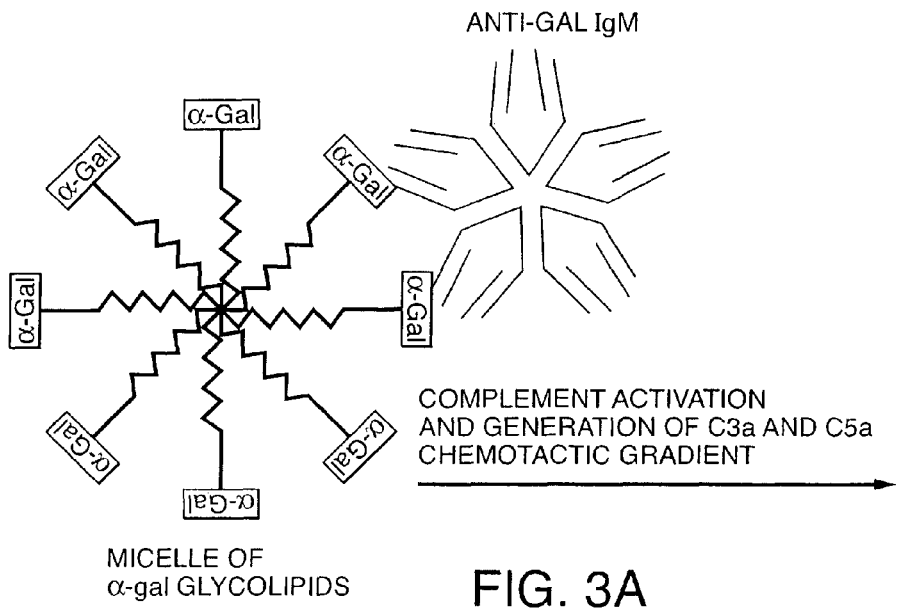

FIG. 3 presents one illustration of interactions between an anti-Gal antibody and α-gal glycolipids.

Panel A. One depiction of micellular α-gal glycolipids binding to an anti-Gal IgM antibody or, alternatively, an anti-Gal IgG antibody. One result of this binding may be an extensive inflammatory reaction.

Panel B. One depiction of membrane inserted α-gal glycolipids binding to an anti-Gal IgM antibody or, alternatively an anti-Gal IgG antibody. One result of this binding may lead to complement mediated cytolysis (CDC) of the cell.

Panel C. One depiction of membrane inserted α-gal glycolipids binding to an anti-Gal IgG antibody (i.e. opsonization) wherein the IgG's Fc portion is bound to Fcγ receptors (FcγR) on macrophages, NK cells, and granulocytes. One result of this binding complex may be the induction of antibody dependent cell mediated cytolysis (ADCC).

Figure 4:
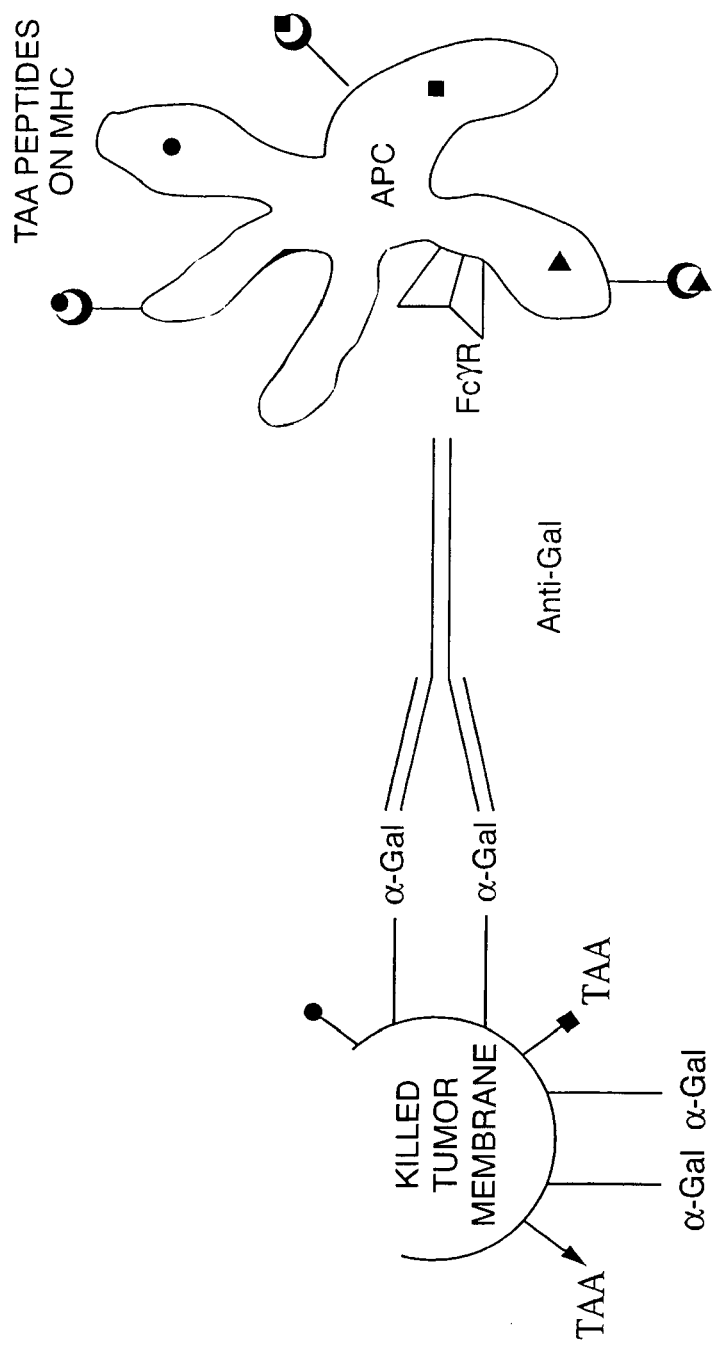

FIG. 4 illustrates an anti-Gal antibody mediated targeting of tumor cell membranes expressing α-gal epitopes to antigen presenting cells. The Fab portion of the anti-Gal IgG is shown bound to killed tumor cell membrane α-gal epitopes. The Fc portion of the anti-Gal IgG is shown bound to the Fcγ receptors (FcγR) on the antigen presenting cells (APC). One result of this binding complex is phagocytosis of the tumor cell membranes by the antigen presenting cells. Consequently, tumor antigens (i.e., for example, TAA-tumor associated antigens; ●, ■, ▲)) are internalized within the APC. Also shown is the ultimate expression of the tumor antigen peptides by the antigen presenting cells in association with major histocompatibility complex (MHC) that are capable of activating tumor specific T cells.

Figure 5B:
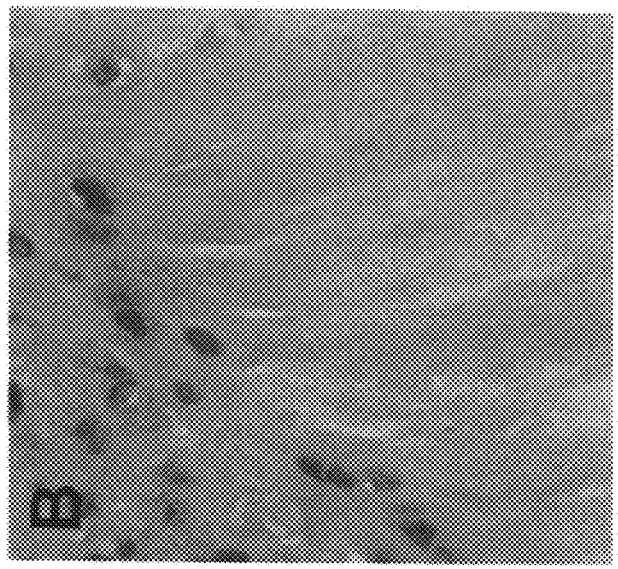
Figure 5A:
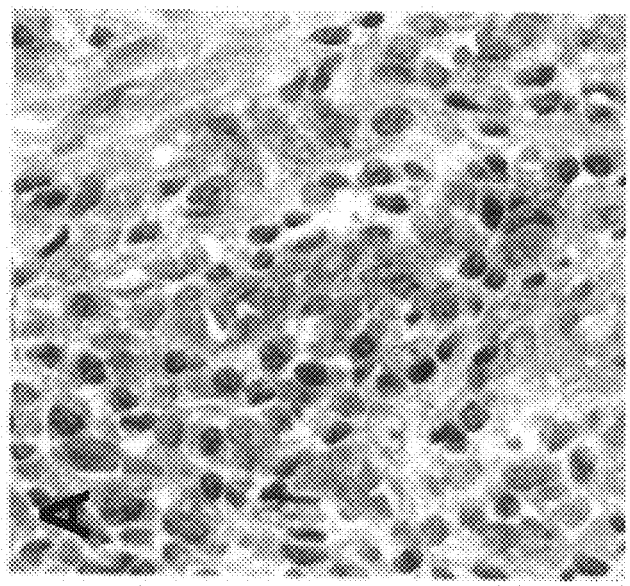
Figure 6A:
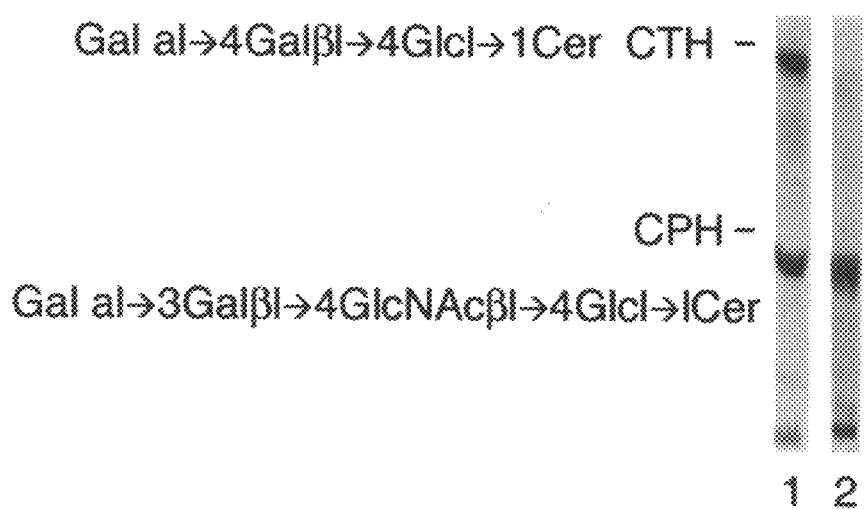
Figure 6B:
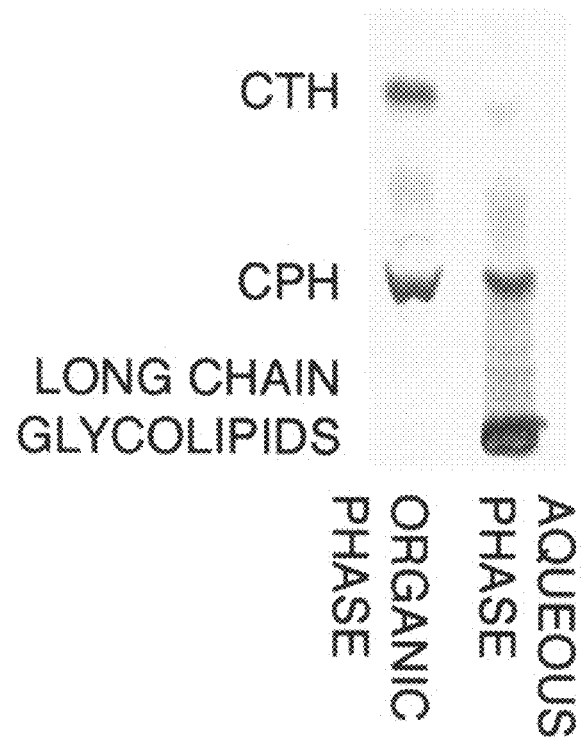
Figure 6C:
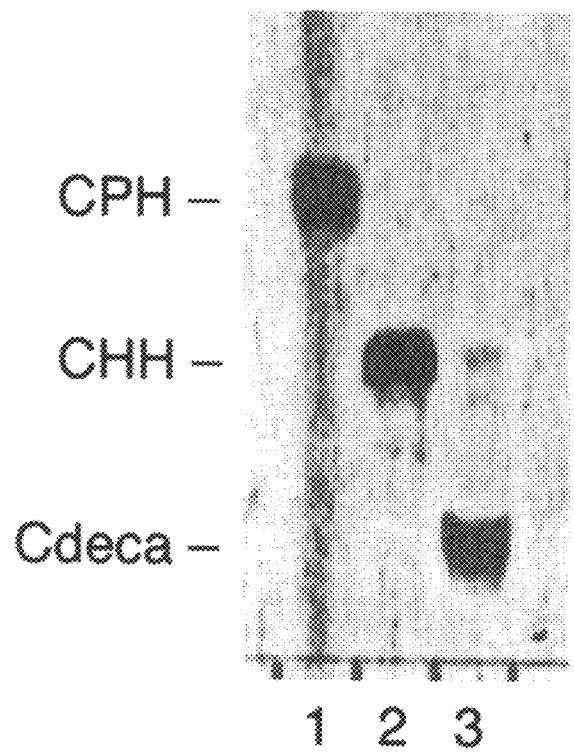
Figure 6D:
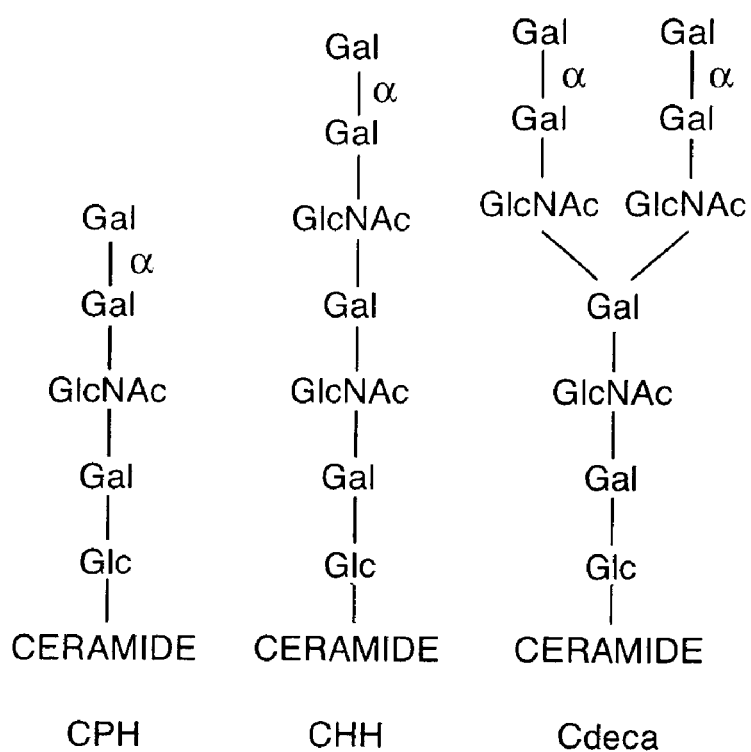

FIG. 5 presents exemplary data showing the rejection of pig meniscus cartilage after a two month implantation into the supra-patellar pouch of rhesus monkeys. Hematoxylin and eosin staining. Magnification: 100×.

Panel A. Inflammatory response in untreated pig cartilage.

Panel B. >95% reduction in inflammatory response in pig cartilage treated with α-galactosidase to eliminate α-gal epitopes.

FIG. 6 presents exemplary data isolating rabbit red blood cell glycolipids by thin layer chromatography and immunostaining with human natural anti-Gal and with mouse monoclonal anti-Gal.

Panel A. Lane 1=Nonspecific orcinol staining of ceramide pentahexoside (CPH) and ceramide trihexoside (CTH). Lane 2=Glycolipid immunostaining with human natural anti-Gal binding to α-gal epitopes occurring in CPH and long-chain (≧7 carbohydrate units) glycolipids (bottom band).

Panel B. Rabbit red blood cell glycolipids extracted into an organic phase (left) and aqueous phase (right) stained nonspecifically with orcinol. Note: The organic phase contains primarily all the ceramide trihexoside (CTH), and a portion of the CPH, whereas the aqueous phase contains the remaining portion of the CPH and all the long-chain glycolipids and almost no CTH.

Panel C. Isolated rabbit red blood cell α-gal glycolipids fractionated by HPLC and identified by immunostaining with monoclonal anti-Gal antibody. CPH: ceramide pentahexoside an α-gal glycolipid with 5 sugars; CHH: ceramide heptahexoside an α-gal glycolipid with 7 sugars; Cdeca: ceramide decahexoside an α-gal glycolipid with 10 sugars.

Panel D. Chemical composition of the α-gal glycolipids CPH, CHH, and Cdeca.

Figure 7:
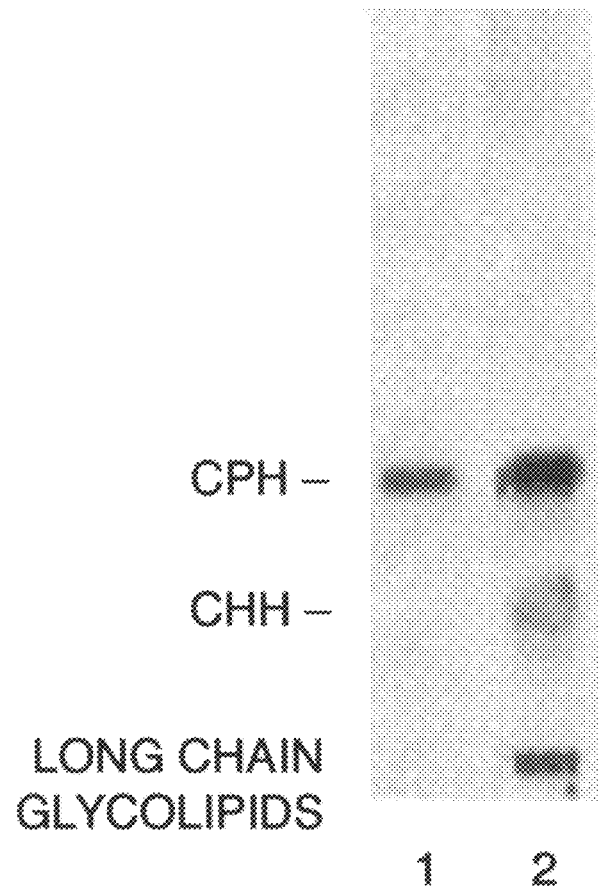

FIG. 7 presents exemplary data isolating bovine red blood cell membrane α-Gal glycolipids using thin layer chromatography. Lane 1 is stained nonspecifically by orcinol and reveals only ceramide pentahexoside (CPH). Lane 2 is immunostained with a natural anti-Gal antibody revealing CPH, CHH, and long chain glycolipids.

Figure 8A:
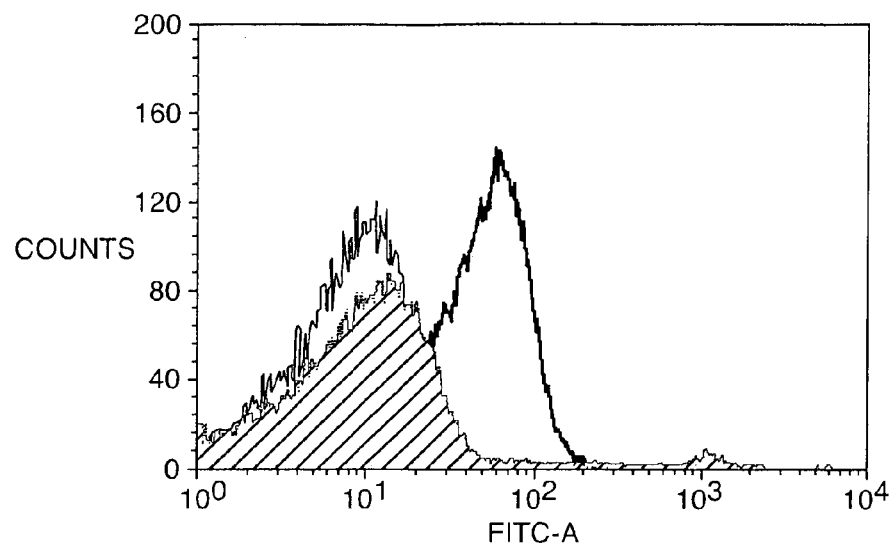
Figure 8B:
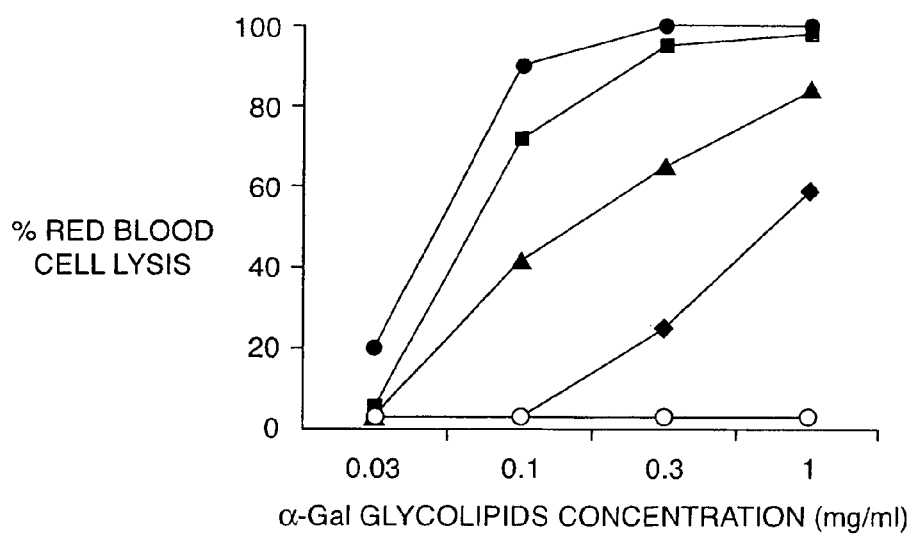

FIG. 8 presents exemplary data demonstrating the insertion of α-gal glycolipids into human red blood cell membranes and subsequent complement mediated lysis of these red blood cells by anti-Gal antibody in autologous serum.

Panel A. Flow cytometry analysis of human red blood cells incubated with 1 mg/ml of α-gal glycolipids 37° C. Solid Line Histogram: Incubation with autologous serum diluted 1:2. Closed Histogram: Incubation with autologous serum depleted of anti-Gal and diluted 1:2.

Dotted Line Histogram: Untreated red blood cells incubated with autologous serum. The dotted line histogram is identical to an isotype control (not shown). IgG binding was assayed by fluorescein (FITC) coupled anti-human IgG.

Panel B. Graphical representation of human red blood cell lysis after 2h glycolipid insertion incubation followed by a 1 h exposure to anti-Gal antibody at various dilutions of autologous serum (37° C.). 1:2 (●); 1:4 (●); 1:8 (▲); 1:16 (♦); heat inactivated serum (56° C.) diluted 1:2 (○).

Figure 9A:
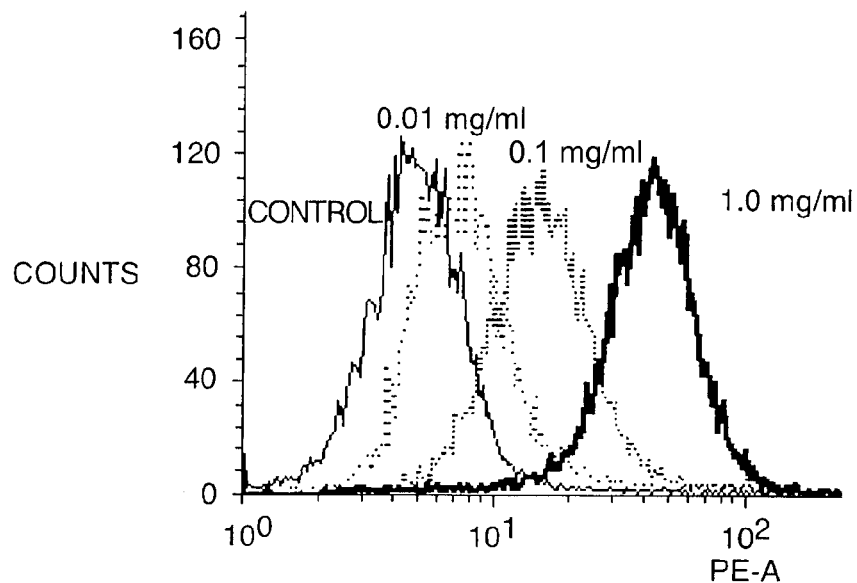
Figure 9B:
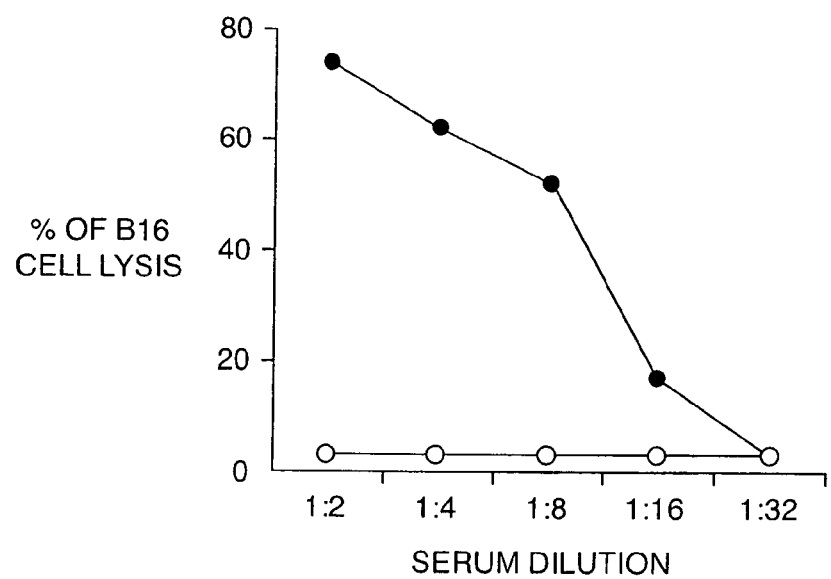

FIG. 9 presents exemplary data showing insertion of α-gal glycolipids into B16 tumor cell membrane and complement dependent cytolysis of these cells after exposure to anti-Gal IgG.

Panel A. Flow cytometry analysis of B16 melanoma cells after 2 h incubation at various α-gal glycolipid concentration (37° C.). Solid Thick Lined Histogram—1 mg/ml α-gal glycolipids; Thick Broken Line Histogram—0.1 mg/ml α-gal glycolipids; Thin Dotted Line Histogram—0.01 mg/ml α-gal glycolipids; Solid Thin Line Histogram—Control without α-gal glycolipids. Expression of α-gal epitopes was determined by the binding of mouse anti-Gal IgG followed by fluorescein coupled goat anti-mouse IgG. The binding of anti-Gal to control cells (i.e. no α-gal glycolipids) was not different than the isotype control (not shown).

Panel B. B16 tumor cell lysis after α-gal glycolipid insertion (1 mg/ml) and exposure to anti-Gal antibody containing mouse serum (1 h, 37° C.). X Axis: Serum Dilutions. Y Axis: % B16 cell lysis. Anti-Gal antibody containing serum (●). Heat inactivated serum at 56° C. for inactivation of complement (○). Viability was determined by exclusion of Trypan blue (penetrates only dead cells).

FIG. 10 presents exemplary data demonstrating an inflammatory response in the skin of anti-Gal antibody producing α1,3galactosyltransferase knockout mice injected with α-gal glycolipids.

Panel A. Hematoxylin and eosin (H&E) stained dermal section (100×) 4 days after 1 mg/ml α-gal glycolipid/PBS injection (SC). Note: Inflammatory cells within the fat tissue. Arrow: Epidermal layer.

Panel B. A α1,3galactosyltransferase knockout mouse (producing anti-Gal antibody) showing injection site skin darkening (i.e., melanin production) 7 days after α-gal glycolipid injection.

Panel C. A wild type mouse (lacking anti-Gal antibody) showing no injection site skin darkening (i.e., no melanin production) 7 days after α-gal glycolipid injection.

Panel D. A α1,3galactosyltransferase knockout mouse showing injection site skin darkening diffusion 3 weeks after α-gal glycolipid injection.

Figure 11A:
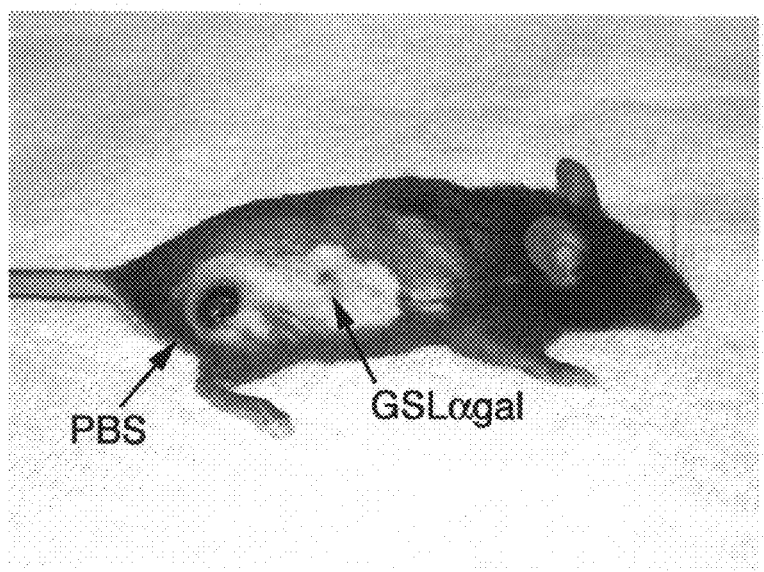

FIG. 11 presents exemplary data comparing cutaneous B16 melanoma tumors (4-5 mm initial diameter) 10 days after treatment with either intratumoral injection of α-gal glycolipids or PBS in eighteen mice.

Panel A. Photograph of a representative mouse. Arrows identified α-gal glycolipid treatment (back tumor) or PBS treatment (front tumor).

Panel B. Bar graph representation of data from all eighteen treated mice. X Axis: KO (knock out) or WT (wild type) mouse number. Y: Axis: Tumor size (mm); Solid Bars: α-gal glycolipids. Open Bars: PBS.

Panel C. Time course representation of tumor growth (presented as mean diameter) in representative mice (18 per group). X Axis: Days after treatment injection. Y Axis: Tumor size (mm). Solid circles: α-gal glycolipids. Open Circles: PBS.

FIG. 12 presents exemplary histological dermal preparations (100×) in α1,3galactosyltransferase knockout mice demonstrating an in vivo inflammatory effect of α-gal glycolipid injection into a melanoma tumor lesion (4-5 mm diameter).

Panel A. An α-gal glycolipid injected tumor resected on day 4 showing moderate peri-vascular inflammation.

Panel B. An α-gal glycolipid injected tumor resected on day 14 showing extensive peri-vascular inflammation.

Panel C. An α-gal glycolipid injected tumor resected on day 16 showing a developing lymphoid nodule. Excess melanin production is indicated by the dark staining of these cells.

Panel D. A PBS injected tumor resected on day 14 showing no inflammatory response. A PBS injected tumor resected on day 4 showed similar results (not shown).

Figure 13A:
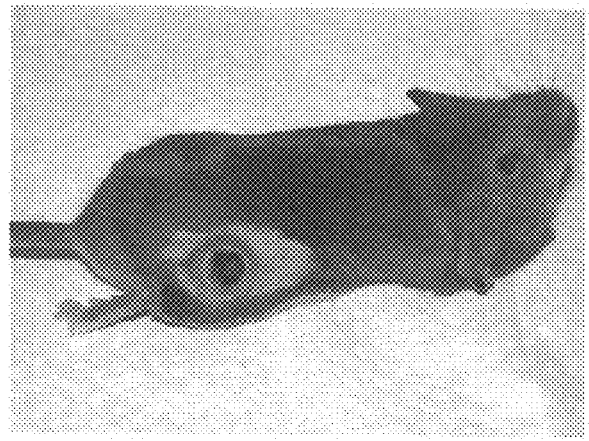
Figure 13B:
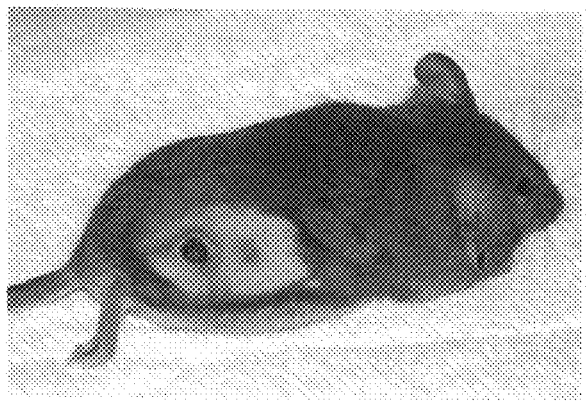
Figure 13C:

FIG. 13 presents exemplary data from a representative α1,3galactosyltransferase knockout mouse showing B16 melanoma tumor regression following intratumoral injection of α-gal glycolipids.

Panel A. A representative tumor immediately before multiple site intratumoral injection of 1 mg α-gal glycolipids.

Panel B. An approximate 50% tumor regression 5 days after intratumoral α-gal glycolipid injection.

Panel C. An almost complete tumor regression 15 days after α-gal glycolipids injection. Note: Skin darkening reflects melanin production in a spot where α-gal glycolipids were injected devoid of a tumor (see FIG. 10B).

FIG. 14 shows representative data showing phagocytosis of anti-Gal antibody (10 μg/ml) opsonized tumor cells by antigen presenting cells (macrophages and dendritic cells).

Panel A. A representative micrograph (1000×) showing internalization of 5 α-gal epitope expressing lymphoma cells in the lowermost portion of a macrophage. The oval structure at the top is the macrophage's nucleus.

Panel B. A representative micrograph (1000×) showing phagocytosis of a α-gal epitope expressing lymphoma cell (round nucleus) by a representative human dendritic cell (elongated nucleus is of the dendritic cell).

Figure 15A:
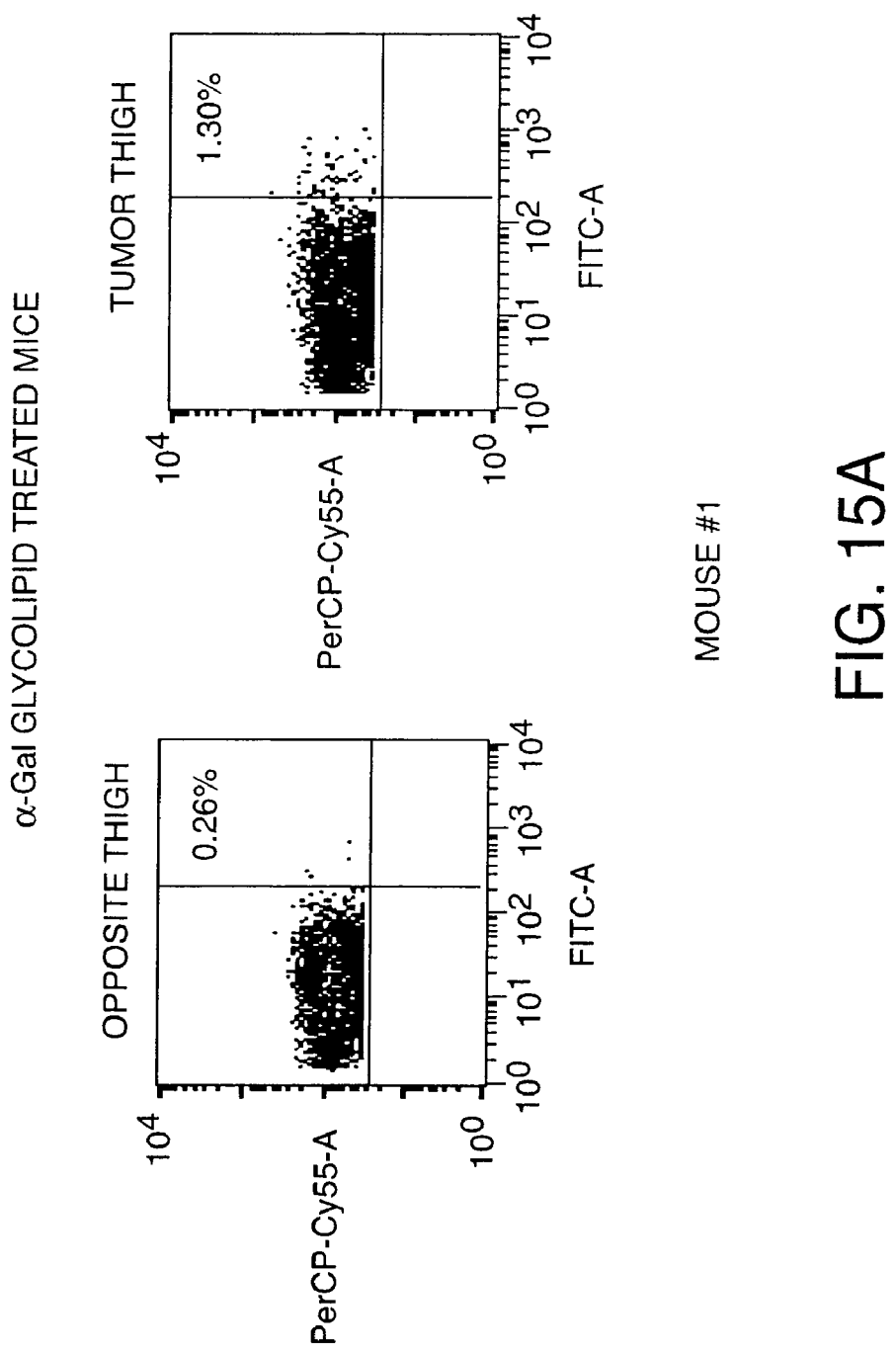
Figure 15B:
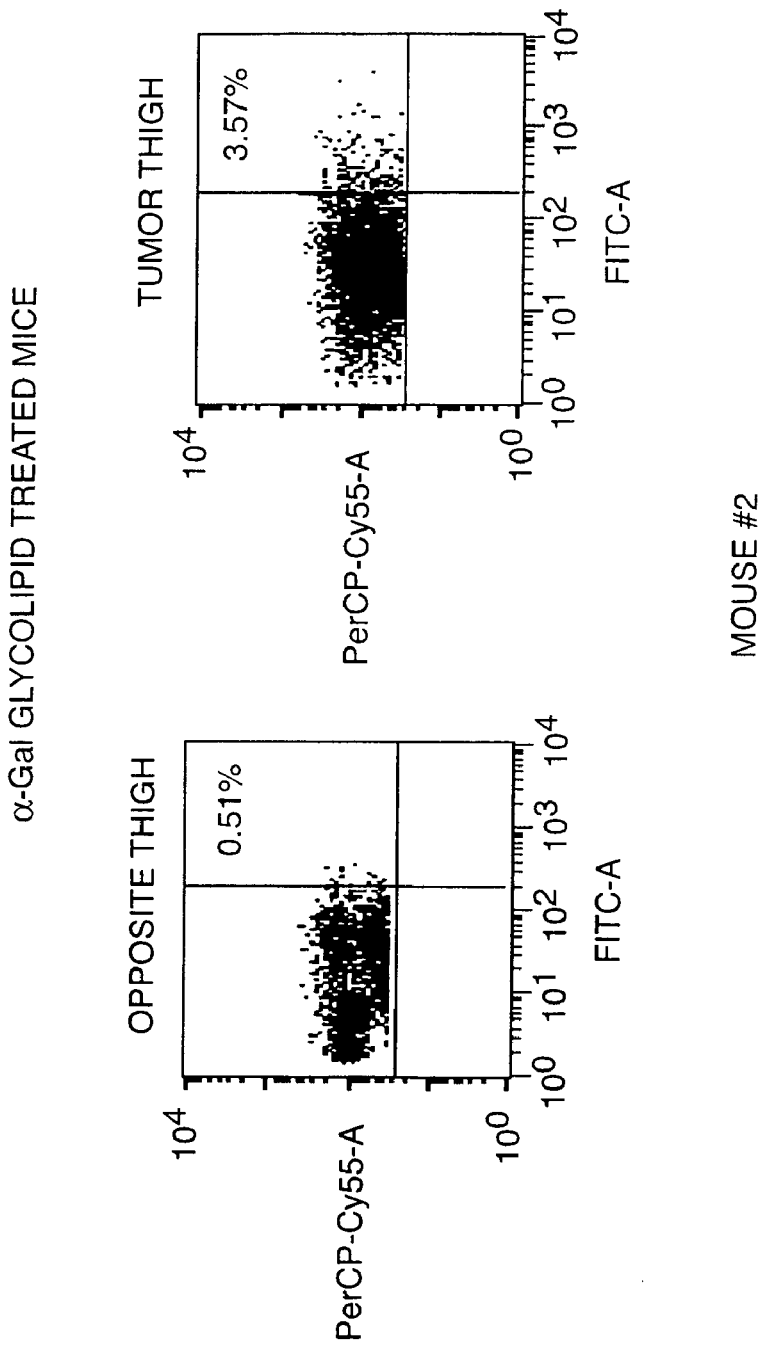
Figure 15C:
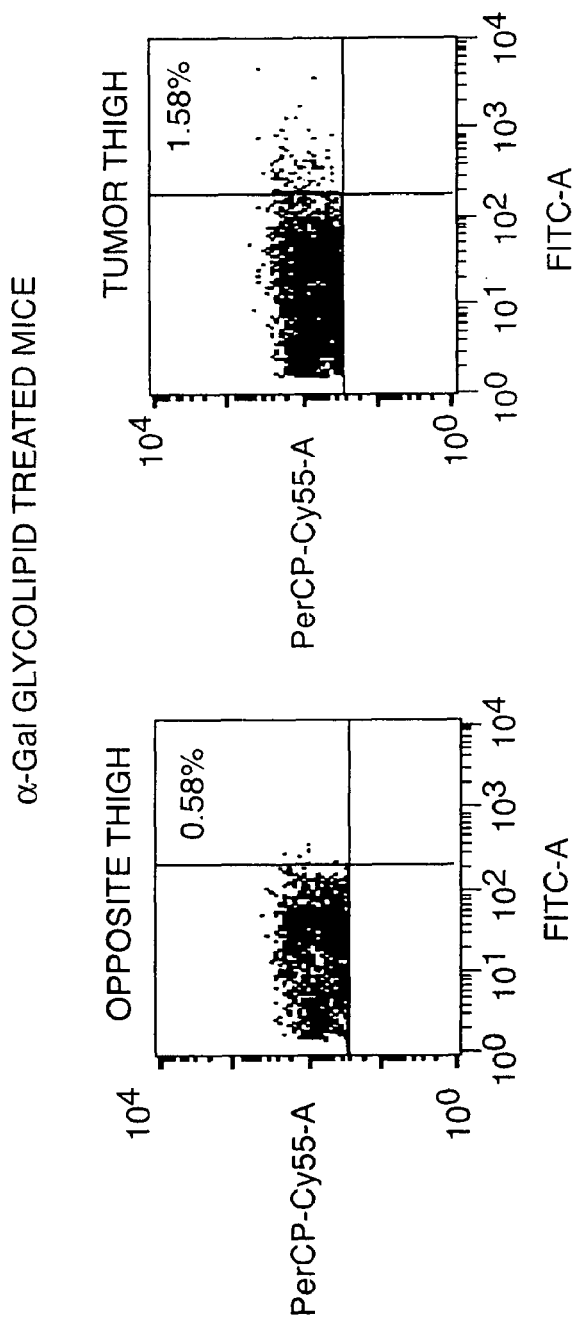
Figure 15D:
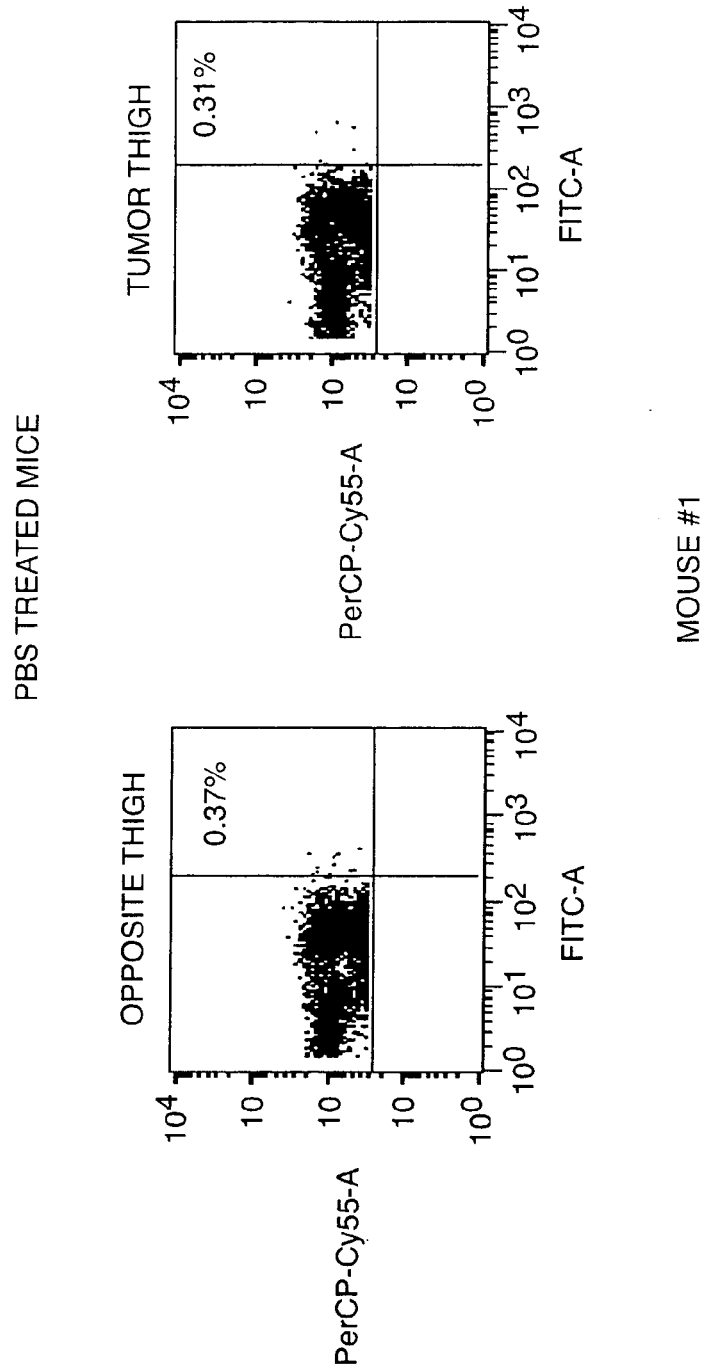
Figure 15E:
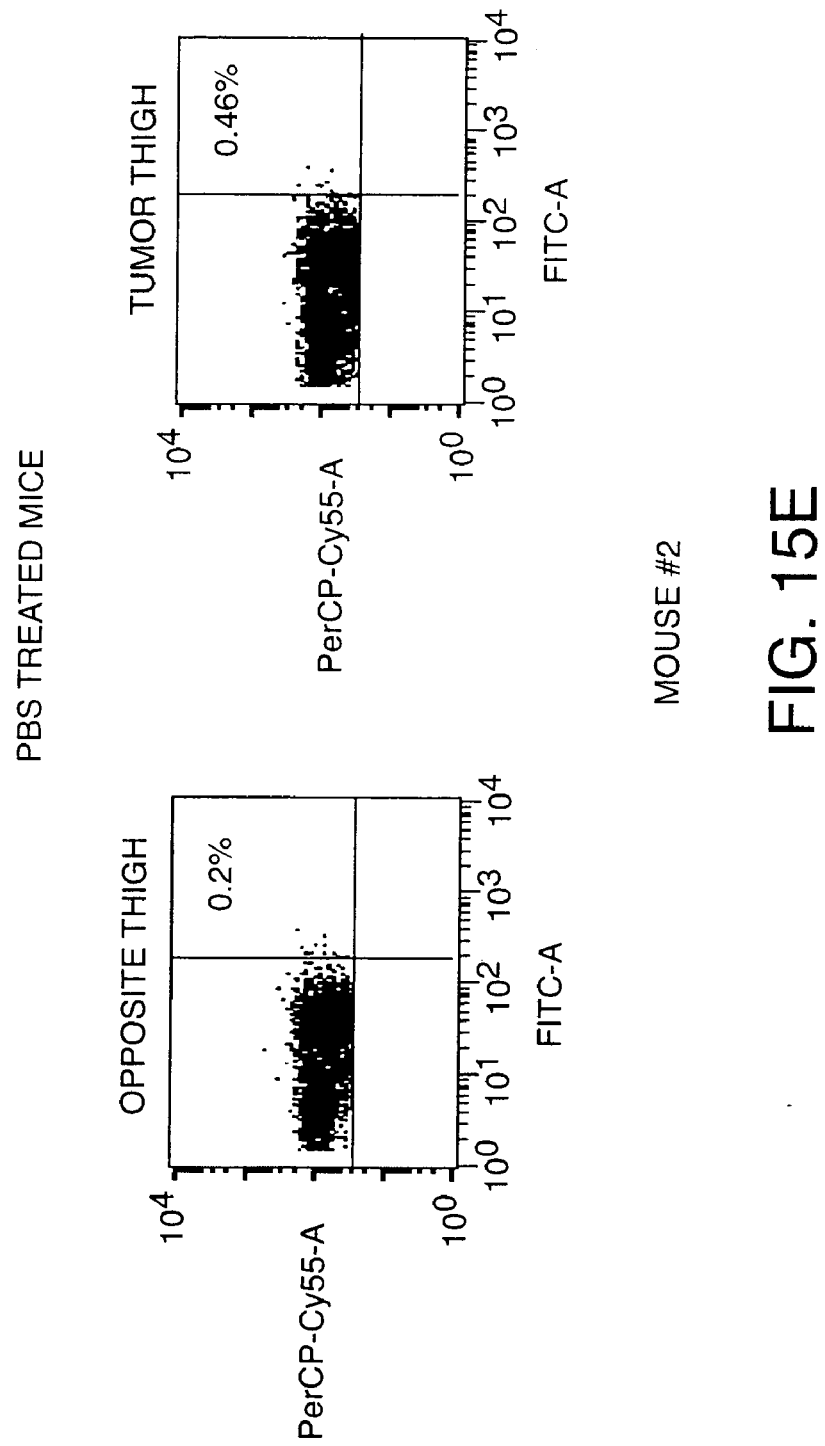
Figure 15F:

FIGS. 15A-F presents exemplary data of a flow cytometry analysis of B3Z T hybridoma cell activation by antigen presenting cells expressing the ovalbumin (OVA) peptide SIINFEKL (SEQ ID NO:1) within lymph nodes. Scatterplot data is presented for three representative mice comparing tumors injected with α-gal glycolipid (FIGS. 15A-C) or PBS (FIGS. 15D-F). The % of activated B3Z cells is indicated in the upper right quadrant for each mouse in each condition. A significant number of B3Z cells are activated by antigen presenting cells within lymph nodes from thighs of mice in which the tumors were injected with α-gal glycolipids, whereas almost no activated B3Z cells were observed when these cells were incubated with cells from lymph nodes of mice with tumors injected with PBS, or with cells from lymph nodes of the tumor free thigh.

Figure 16:
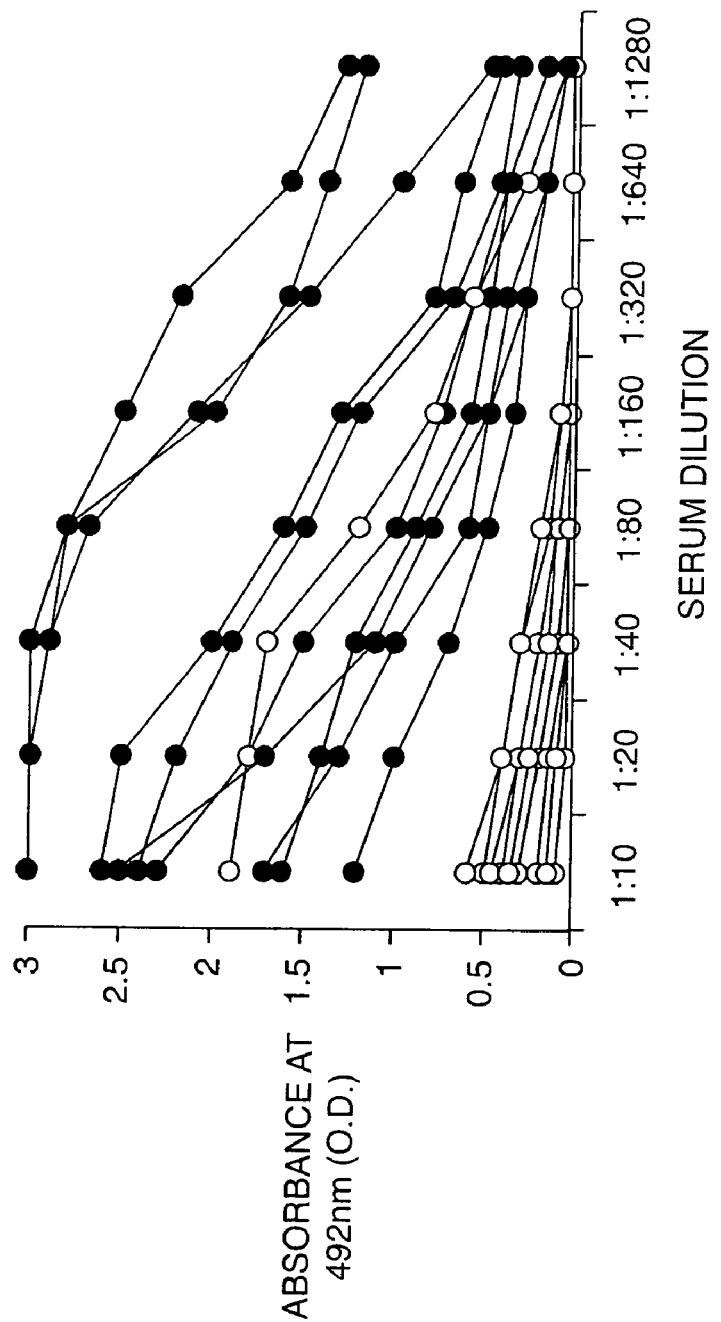

FIG. 16 presents exemplary data from an ELISA analysis of anti-OVA antibody production in twenty α1,3galactosyltransferase knockout mice with B16/OVA tumors in the right flank intratumorally injected one a week for three weeks with α-gal glycolipids or with PBS. X Axis: Serum dilution levels. Y Axis: Optical density. (●) 1 mg α-gal glycolipid injection (N=10); (○) PBS injection (N=10).

Figure 17:
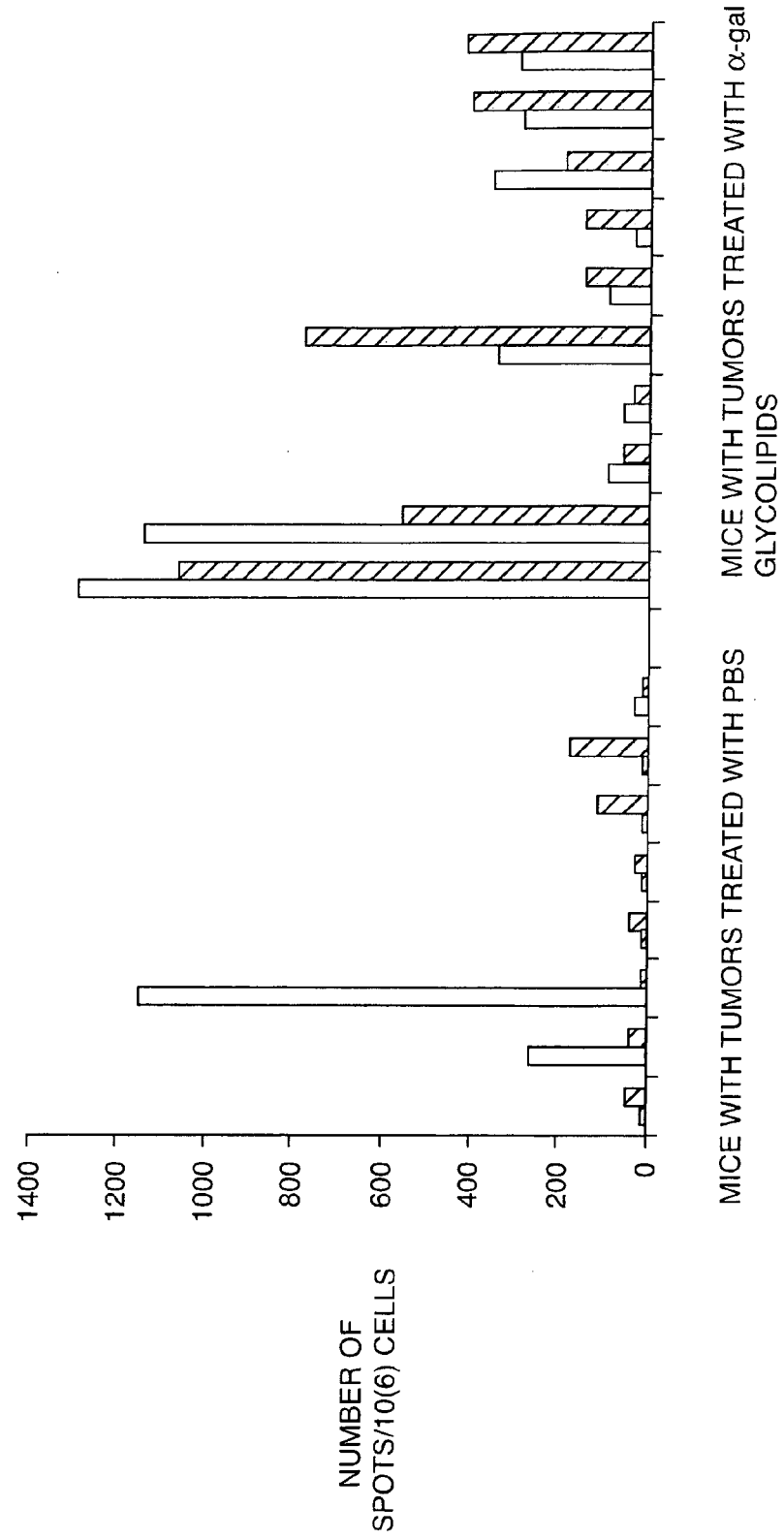

FIG. 17 presents exemplary data from ELISPOT analysis for interferon gamma (IFNγ) secretion by splenocyte T cells ($2\times10^5$ cells/ml) from eighteen α1,3galactosyltransferase knockout mice with B16/OVA tumors in the right flank intratumorally injected once a week for three weeks with α-gal glycolipids or with PBS. X Axis: Mouse number. Y Axis: Number of cell spots. Mice #1-8: PBS injection. Mice #9-18: 1 mg/injection of α-gal glycolipids. Open columns: APCs passed with 5 μg/ml of the peptide $OVA_{257-264}$ presented on class I MHC molecules. Closed columns: APCs passed with 5 μg/ml of the peptide $OVA_{323-339}$ peptide presented on class II MHC molecules.

Figure 18A:
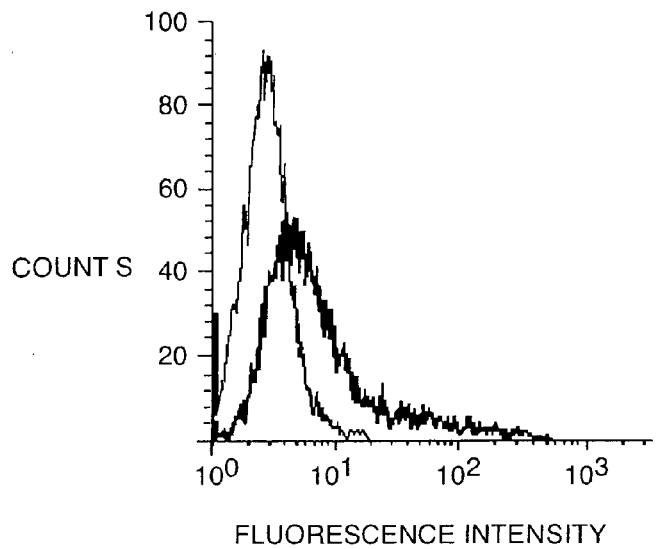
Figure 18B:
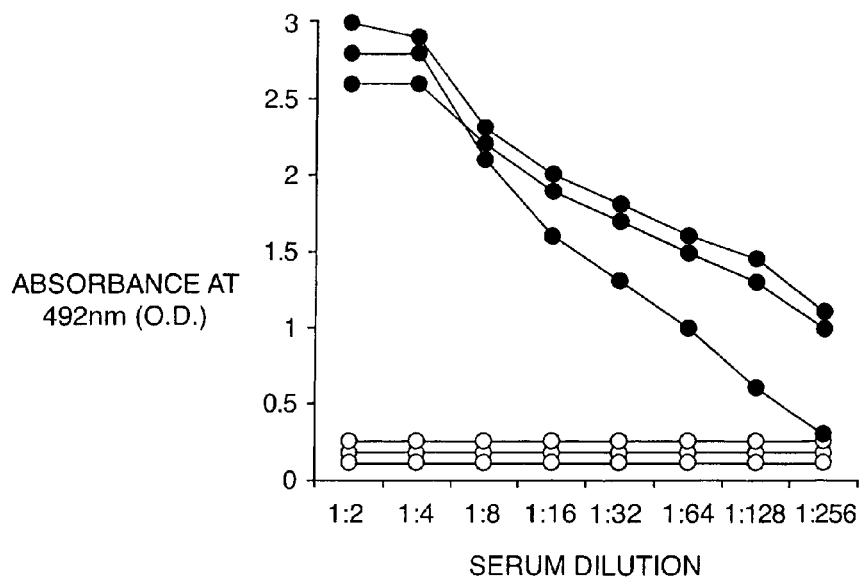

FIG. 18 presents exemplary data showing expression of α-gal epitopes on BL6 cells transduced with AdαGT.

Panel A. Flow cytometry data of BL6 cells stained with *Bandeiraea simplicifolia* IB4 lectin coupled to fluorescein (FITC). Thin line histogram: $BL6_{Adcont}$ cells (i.e. melanoma cells transduced with adenovirus containing no inserted genes). Thick line histogram: $BL6_{AdαGT}$ cells.

Panel B. Binding of anti-Gal antibody in α1,3galactosyltransferase knockout mouse serum to α-gal epitopes from: (●) $BL6_{AdαGT}$ cells; (○) $BL6_{Adcont}$ cells (N=3). X Axis: Serum dilution level. Y Axis: ELISA Optical Density.

Figure 19A:
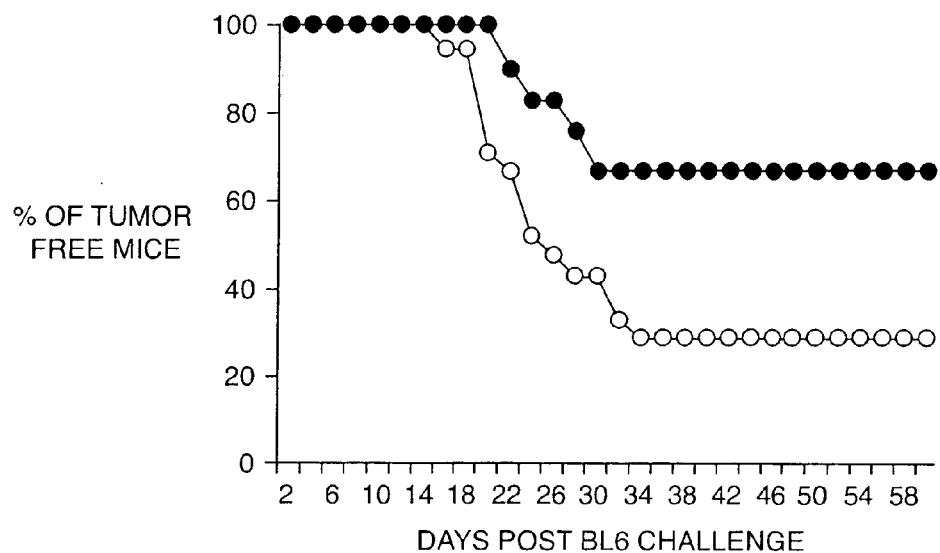

FIG. 19 presents exemplary data showing the protection of α1,3galactosyltransferase knockout mice from BL6 tumor challenge using $BL6_{AdαGT}$ vaccine. (●) α1,3 Galactosyltransferase knockout mice vaccinated with $2\times10^6$ $BL6_{AdαGT}$; (○) α1,3 Galactosyltransferase knockout mice vaccinated with $BL6_{Adcont}$. Immunizations were repeated after one week. X Axis: Day number following BL6 tumor challenge.

Panel A. Mice challenged with $0.2\times10^6$ live BL6 cells. $BL6_{AdαGT}$ (N=22). $BL6_{Adcont}$ (N=21).

Panel B. Mice challenged with $0.5\times10^6$ live BL6 cells. $BL6_{AdαGT}$ (N=21). $BL6_{Adcont}$ (N=18).

Figure 20A:

FIG. 20 presents exemplary data showing the treatment of a cutaneous B16 melanoma tumors (4-5 mm initial diameters) by intratumoral adenovector injections.

Panel A. A histological representation of tumor cells injected with AdαGT and stained with fluorescein coupled *Bandeiraea simplicifolia* IB4 (BS) lectin 72 h post injection. Note the green stained cells that are tumor cells expressing α-gal epitopes.

Panel B. A tumor size comparison in a representative mouse (N=4) 10 days after intratumoral vector injections. Arrows show AdαGT treated tumor (back tumor) and $Ad_{cont}$ treated tumor (front tumor). The treated tumors had an initial diameter of 4-5 mm.

Panel C. A histological representation of an AdαGT injected tumor 6 days post injection. Note: Inflammatory reactions are present in the treated tumor. Stain: Hematoxylin & Eosin. Magnification: 100×.

Figure 21:
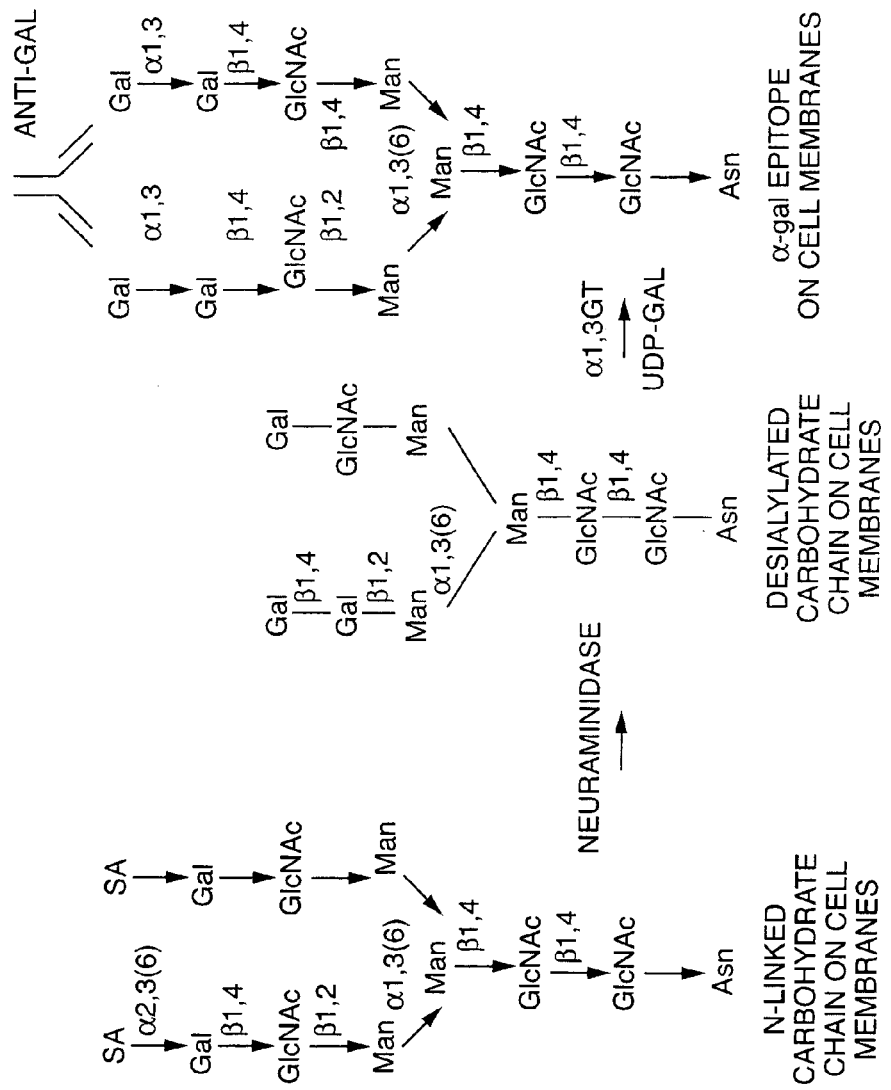

FIG. 21 presents one embodiment of the synthesis of a α-gal epitope on tumor cells by administration of neuraminidase, α1,3galactosyltransferase and UDP-Gal.

Figure 22:
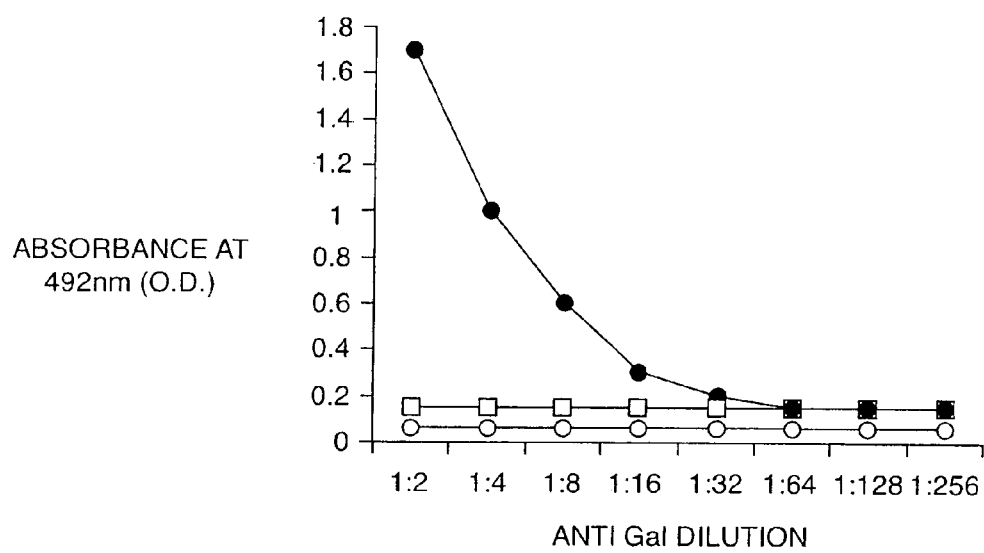

FIG. 22 presents exemplary data showing enzymatic synthesis of α-gal epitopes in accordance with FIG. 21 on freshly obtained human chronic lymphocytic leukemia cells. X Axis: Anti-Gal antibody dilution level. Y Axis: ELISA Optical Density.

(○) UDP-Gal only; (□) recombinant α1,3galactosyltransferase only; (●) neuraminidase and recombinant a α1,3galactosyltransferase.

Figure 23B:
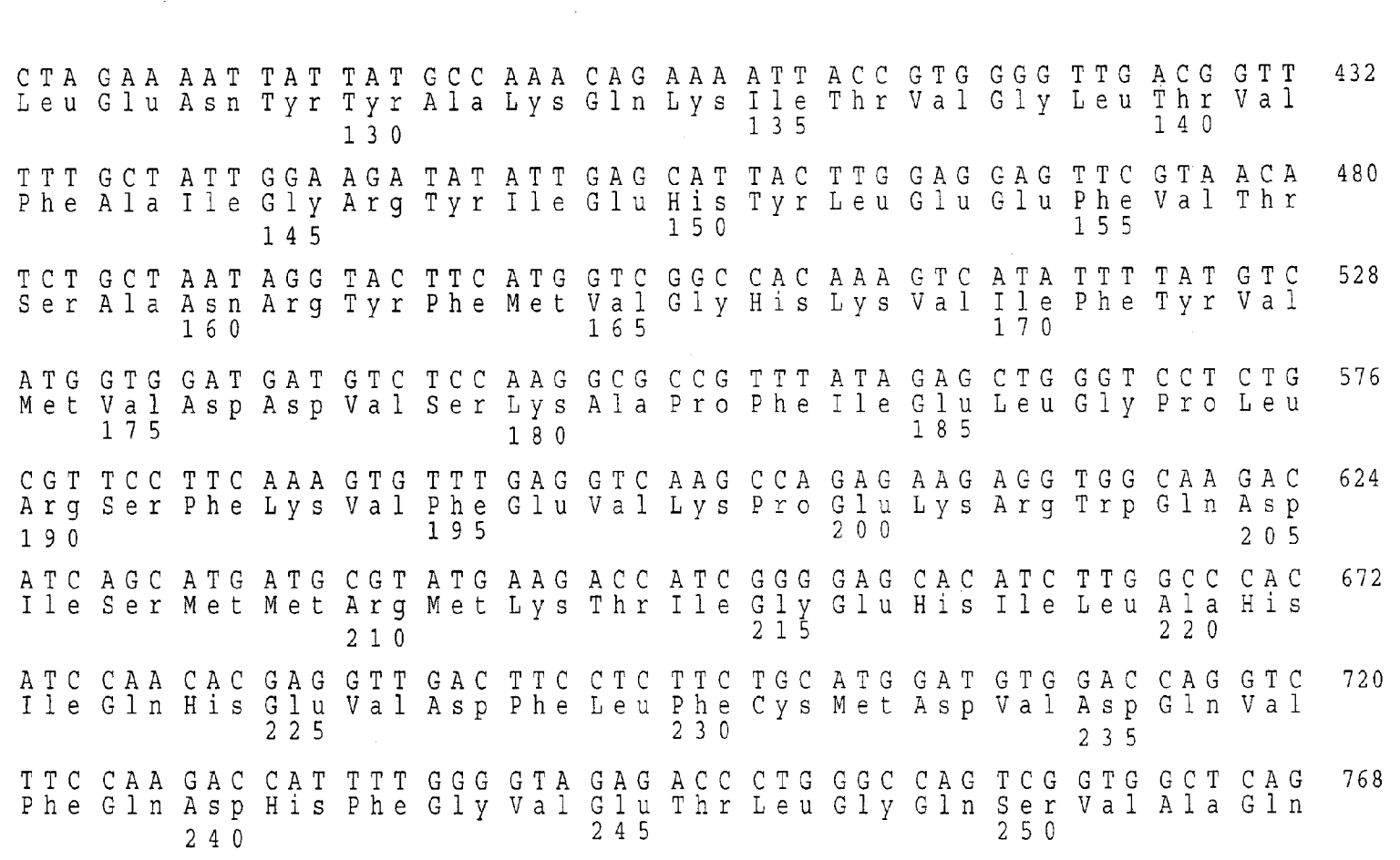
Figure 23C:
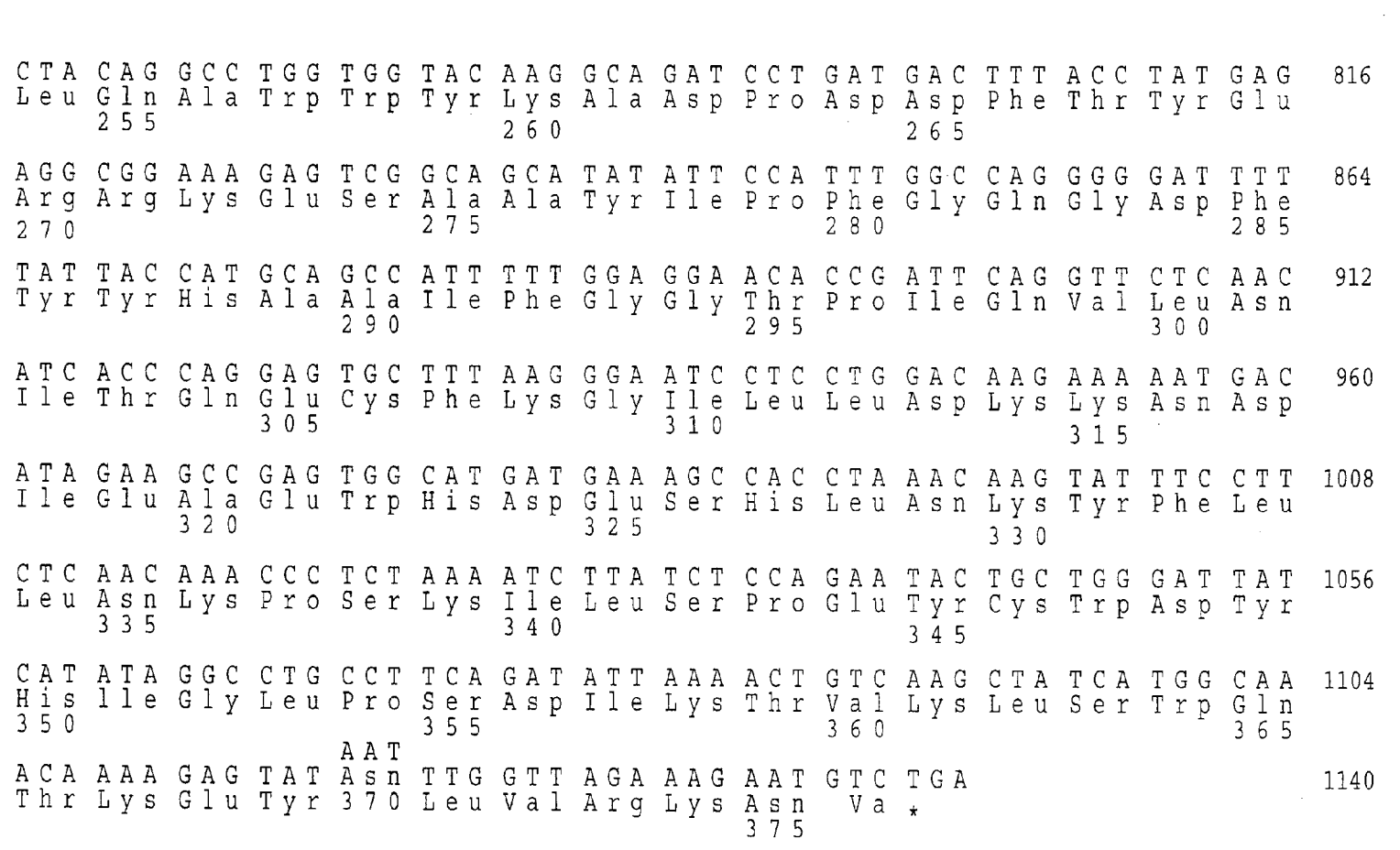

FIG. 23A-C presents one embodiment of a marmoset α-galatosyltransferase nucleic acid sequence (SEQ ID NO: 2).

FIG. 24 presents one embodiment of a marmoset α-galatosyltransferase amino acid sequence (SEQ ID NO: 3).

Figure 25:
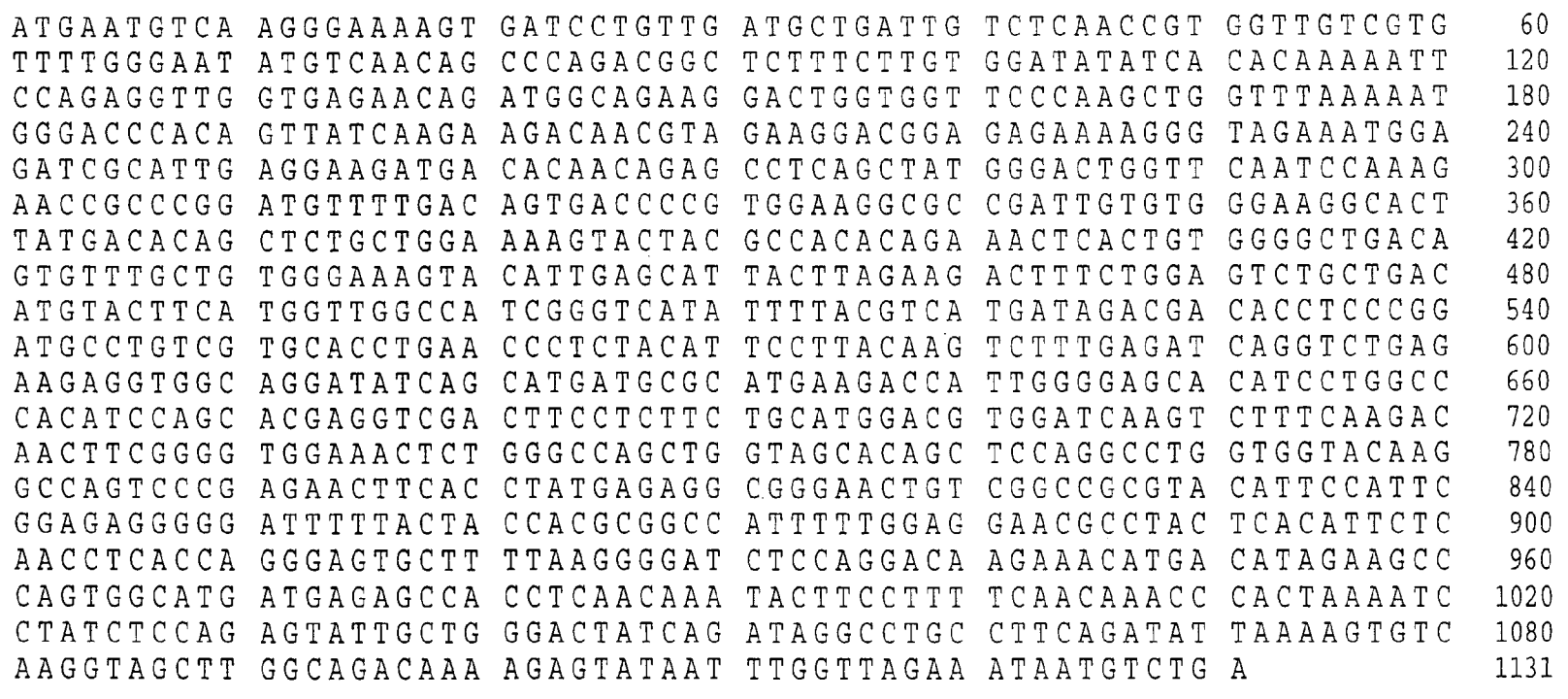

FIG. 25 presents one embodiment of a mouse α-galatosyltransferase nucleic acid sequence. (SEQ ID NO: 4).

DETAILED DESCRIPTION OF THE INVENTION

The present invention is related to the field of cancer treatment. In one embodiment, the invention contemplates administering compounds to tumor lesions that induce local expression of α-gal epitopes within the tumor. In one embodiment, the administration induces regression and/or destruction of the treated tumor lesions. In another embodiment, the administration converts the treated tumor lesions into an autologous tumor vaccine. In one embodiment, the compounds comprise glycolipids having an α-gal epitope. In another embodiment, the compounds comprise a mixture of α1,3galactosyltransferase, neuraminidase, and uridine diphosphate galactose.

Figure 1A:
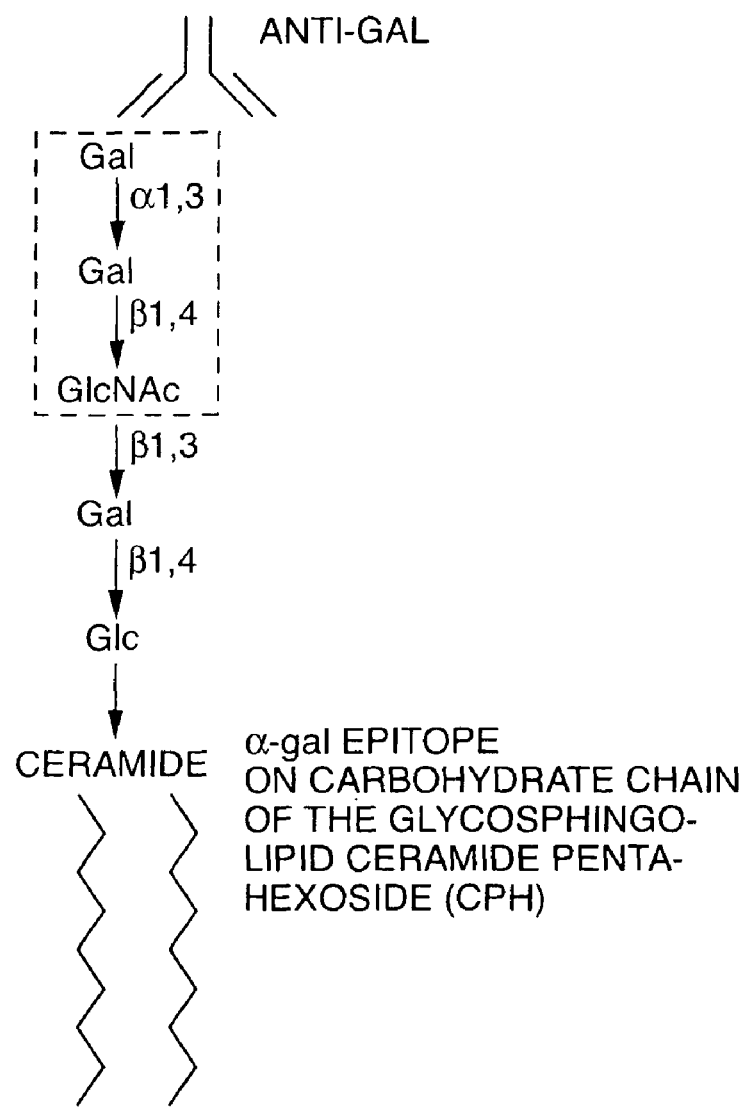
FIG. 1 presents one embodiment of the structure of α-gal epitope (Galα1-3Galβ1-4GlcNAc-R) on a representative glycolipid ceramide pentahexoside (CPH). The terminal galactosyl (Gal) is linked α1,3 to the penultimate Gal that is linked β1-4 to N-acetylglucosamine (GlcNAc) of the carbohydrate chain.
Figure 1B:
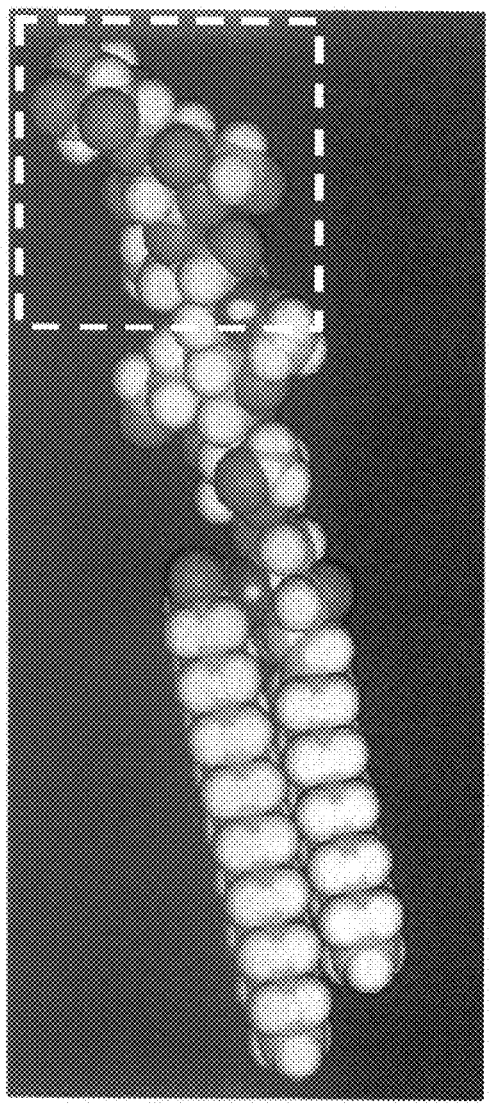

The invention described herein comprises a novel therapy treatment modality that includes, but is not limited to, intratumoral delivery of glycolipids that carry α-gal epitope and referred to as α-gal glycolipids (i.e., for example, ceramide pentahexoside (CPH); see FIG. 1A and FIG. 1B). α-gal glycolipids can be inserted into the outer leaflet of the cell membrane of tumor cells within the treated lesion. The presence of α-gal glycolipids in the tumor lesion achieves two goals:

1. Immune mediated destruction of tumor lesions by the inflammatory process that is induced within the tumor lesion by the interaction between the natural anti-Gal antibody and the α-gal epitopes of α-gal glycolipids, and 2. Effective uptake by antigen presenting cells of tumor cells and tumor cell membranes with inserted α-gal glycolipids and thus, expressing α-gal epitopes that bind in situ anti-Gal antibodies, thereby converting the treated tumor lesion into an autologous tumor vaccine (see FIG. 3 and FIG. 4).

Although it is not necessary to understand the mechanism of an invention, it is believed that this uptake results in an effective immune response against tumor antigens present on or within the tumor cells expressing α-gal epitopes. It is further believed that this immune response may result in immune mediated destruction of metastatic tumor cells that do not express α-gal epitopes, but express the tumor antigen.

In one embodiment, the invention contemplates administering by injection, or any other means, compounds into tumors that induce expression of a tumor-specific epitope. In one embodiment, the compound comprises a glycolipid having an α-gal epitope, generally referred to as an α-gal glycolipid. Such administration of α-gal glycolipids achieves the following objectives:

1. The binding of the natural anti-Gal antibody to α-gal epitopes of α-gal glycolipids may result in local complement activation, thereby generating chemotactic factors including, but not limited to, C5a and C3a. These chemotactic factors induce a strong intra-lesion inflammatory response and extensive migration of antigen presenting cells into the tumor tissue (See FIG. 3A).

2. The lipid tails of α-gal glycolipids have the capability to spontaneously insert into the tumor cell membranes within the treated lesion, resulting in expression of α-gal epitopes on tumor cells. Anti-Gal binding to these epitopes are believed to induce regression and/or destruction of tumors comprising tumor cells (See FIGS. 3B and 3C).

3. Opsonization of the tumor cell membranes by anti-Gal targets them for effective uptake by antigen presenting cells that migrate into the tumor due to the induced inflammation (See FIG. 4).

The Fc portion of the tumor cell membrane bound anti-Gal IgG molecules binds to Fcγ receptors (FcγR) on antigen presenting cells and induces uptake of the tumor cells by the antigen presenting cells. (See FIG. 4). A similar induction for uptake may occur as a result of the interaction between the C3b component of complement deposits on anti-Gal binding tumor cells and C3b receptors on antigen presenting cells. This anti-Gal mediated targeting of tumor membranes to antigen presenting cells enables effective transport of autologous tumor antigens to draining lymph nodes, and processing and presentation of immunogenic tumor antigen peptides by antigen presenting cells within the lymph nodes (See FIG. 4).

Thus, intratumoral injection of α-gal glycolipids converts a treated tumor lesion into an in situ autologous tumor vaccine that provides tumor antigens to the immune system, thereby eliciting a protective anti-tumor immune response. This immune response is capable of inducing tumor regression comprising the destruction of individual tumor cells or of small aggregates of tumor cells (i.e., for example, micrometastases). These micrometastases are usually undetectable either visually or by imaging and not accessible by conventional surgical techniques (i.e., for example, they are nonresectable because of the small size).

Tumor regression and/or destruction followed by a conversion into autologous tumor vaccine can also be achieved by an intratumoral injection of gene therapy vectors containing the α1,3galactosyltransferase gene. Successful transfection of tumor cells by a α1,3 galactosyl-transferase gene results in the expression of α-gal epitopes on the transfected cell membrane. Naturally occurring anti-Gal antibody may then bind to these de novo α-gal epitopes thereby inducing an inflammatory process. This inflammatory process can result in regression and/or destruction of the treated tumor lesions followed by conversion into autologous tumor vaccines.

Tumor regression and/or destruction by natural anti-Gal antibody and conversion of the treated tumor lesion into an autologous tumor vaccine can also be achieved by introducing into tumors a solution comprising α1,3galactosyltransferase, neuraminidase, and uridine diphosphate galactose (UDP-Gal). The α1,3galactosyltransferase enzyme synthesizes α-gal epitopes on the N-acetyllactosamine residues (Galβ1-4GlcNAc-R or Galβ1-3 GlacNAc-R) of carbohydrate chains of cell surface glycolipids and glycoproteins. Although it is not necessary to understand the mechanism of an invention, it is believed that the role of neuraminidase is to remove terminal sialic acid units from the carbohydrate chains in order to expose penultimate N-acetyllactosamine residues. Further, it is believed that if the N-acetyllactosamine residues on carbohydrate chains are not capped with sialic acid then the synthesis of α-gal epitopes by α1,3galactosyltransferase occurs without the need for neuraminidase. The α-gal epitopes on cell membranes readily bind in situ the natural anti-Gal antibody molecules, thereby inducing tumor regression and/or destruction (See FIG. 3). Following opsonization, the tumor cells become (i.e., are converted) an in situ autologous tumor vaccine providing tumor cell membranes comprising tumor antigens, also referred to as associated antigens (TAAs), for uptake by antigen presenting cells (See FIG. 4).

I. Natural Anti-Gal Antibody, α-Gal Epitope, and Xenograft Rejection

Anti-Gal is believed to be a natural IgG antibody that may be present in all humans, constituting at least 1% of serum immunoglobulins (Galili et al., *J. Exp. Med.* 1984; 160: 1519-31, and Hamadeh R M, Galili U, Zhou P, Griffis J M. *Clin. Diagnos. Lab. Immunol.* 1995; 2:125-31). Studies have presented data indicating that anti-Gal antibody might interact specifically with α-gal epitopes on cell surface or free glycolipids and glycoproteins. (Galili, U., Macher, B. A., Buehler, J. and Shohet, S. B. *J. Exp. Med.* 1985, 162: 573-82, and Galili U. *Springer Semin Immunopathol.* 1993; 15: 155-171). It is further reported that the anti-Gal antibody may be produced throughout life as a result of antigenic stimulation by bacteria of the gastrointestinal flora (Galili, U., Mandrell, R. E., Hamadeh, R. M., Shohet, S. B. and Griffis, J. M. *Infect. Immun.* 1988; 56: 1730-37).

The α-gal epitope can be abundantly synthesized on glycolipids and glycoproteins by the glycosylation enzyme α1,3galactosyltransferase within the Golgi apparatus of cells of nonprimate mammals, prosimians and in New World monkeys (Galili U, Shohet S B, Kobrin E, Stults C L M, Macher B J. *Biol. Chem.* 1988; 263; 17755-62). In contrast, humans, apes, and Old World monkeys lack α-gal epitopes, but produce the natural anti-Gal antibody in very large amounts (Galili U, Clark M R, Shohet, S B, Buehler J, Macher B A. *Proc. Natl. Acad. Sci. USA* 1987, 84: 1369-73). Based on the sequence of the α1,3galactosyltransferase pseudogene in monkeys and apes, it was estimated that the α1,3galactosyltransferase gene was inactivated in ancestral Old World primates approximately 20 million years ago (Galili U, Swanson K. *Proc. Natl. Acad. Sci. USA* 1991; 88: 7401-04). It was suggested that that this evolutionary event was associated with the appearance of an infectious microbial agent, endemic to the Old World (i.e. currently Europe, Asia and Africa), which was detrimental to primates and which expressed α-gal epitopes. Primates could produce anti-Gal as a protective antibody against such putative detrimental agent, only after they evolved under a selective pressure for the inactivation of the α1,3galactosyltransferase gene and thus, loss of immune tolerance to the α-gal epitope. Galili U, Andrews P. *J. Human Evolution* 29:433-42, 1995.

The strong protective activity of the natural anti-Gal antibody has been evolutionarily conserved in humans and monkeys. This can be inferred from xenotransplantation studies with pig organs expressing α-gal epitopes. Since cells of various mammals, including pigs, express α-gal epitopes, organs from pigs transplanted in humans, or in Old World monkeys, are rejected because of the in vivo binding of the anti-Gal antibody to these epitopes on pig cells (Galili, U. *Immunol. Today* 1993, 14: 480-82). Transplantation of pig tissues into humans or into Old World monkeys results in avid anti-Gal binding to α-gal epitopes on an in vivo graft and the subsequent induction of the xenograft rejection. Vascularized xenografts (e.g. pig heart) undergo rapid rejection (called hyperacute rejection) in monkeys within 30-60 min as a result of anti-Gal IgM molecules binding to α-gal epitopes on pig endothelial cells, activation of complement, lysis of the endothelial cells, and collapse of the vascular bed (Collins B H, Cotterell A H, McCurry K R, Alvarado C G, Magee J C, Parker W, Platt J L. *J. Immunol.* 1995; 154: 5500-10). In addition, much of the destruction of xenograft cells in extravascular areas is mediated by anti-Gal IgG binding to α-gal epitopes on various cells. This binding results in antibody dependent cell mediated cytolysis (ADCC), following the binding of the Fc portion of anti-Gal IgG to cell bound Fcγ receptors on granulocytes, macrophages, and NK cells.

The anti-Gal IgG mediated destruction of xenografts can be monitored with pig cartilage (an avascular xenograft tissue) transplanted into rhesus monkeys (i.e. monkeys that naturally produce anti-Gal antibody). Studies indicate that the binding of anti-Gal to α-gal epitopes in the pig tissue results in induction of an extensive inflammatory reaction that leads to gradual destruction of the tissue within 2 months. (See FIG. 5A) (Stone K R, Ayala G, Goldstein J, Hurst R, Walgenbach A, Galili, U. *Transplantation* 1998, 65: 1577-83). Binding of anti-Gal to α-gal epitopes on the cartilage cellular and extracellular matrix glycoproteins further opsonizes them (i.e., forms immune complexes with them) and thus, targets them to antigen presenting cells by the binding of the Fc portion of the immuno-complexed anti-Gal with Fcγ receptors on antigen presenting cells. The antigen presenting cells, in turn, transport these pig glycoproteins to draining lymph nodes where they activate the many T cells specific to the multiple pig xenopeptides. These activated T cells subsequently migrate into the cartilage xenograft implant and comprise approximately 80% of the infiltrating mononuclear cells. (See FIG. 5A). That this inflammatory response is primarily mediated by anti-Gal interaction with α-gal epitopes can be inferred from monitoring the immune response to the pig cartilage xenograft from which the α-gal epitopes were removed by an enzymatic treatment (i.e., for example, using recombinant α-galactosidase). α-galactosidase destroys the α-gal epitopes on the cartilage glycoproteins by cleaving (hydrolyzing) the terminal α-galactosyl unit. In the absence of α-gal epitopes on the pig cartilage glycoproteins, there is no anti-Gal binding to the xenograft, and thus, no effective antigen presenting cell mediated transport of the xenoglycoproteins occurs. This is indicated by a lack of significant T cell infiltration in a xenograft (See FIG. 5B).

In one embodiment, the present invention contemplates exploiting the immunologic potential of the natural anti-Gal antibody, demonstrated in pig cartilage xenograft rejection, for the regression and/or destruction of tumor lesions, treated to display α-gal epitopes and for targeting the tumor cell membranes to antigen presenting cells by anti-Gal antibody. It is believed that such treatment will convert the tumor lesions into in situ autologous tumor vaccines that elicit a systemic protective immune response against the metastatic tumor cells by similar mechanisms as those observed in rejection of pig cartilage in monkeys. It is further believed that the anti-Gal IgG molecules binding to tumor cells expressing α-gal epitopes will target tumor cell membranes to antigen presenting cells for eliciting a protective anti-tumor immune response against the autologous tumor antigens expressed on the tumor cells in the treated lesion (See FIG. 4).

II. Anti-Gal Targeting of Autologous Tumor Vaccines to Antigen Presenting Cells

Autologous tumor cells or tumor cell membranes have been reported to function as autologous tumor vaccines in cancer patients (Galili, U.S. Pat. No. 5,879,675, herein incorporated by reference and Galili, U., *Cancer Immunology Immunotherapy* 2004; 53: 935-945). These studies utilize intact tumor cells obtained from hematological malignancies, or tumor cell homogenates obtained from solid tumors, and are processed in vitro to express multiple α-gal epitopes. This is achieved by incubation of a cell culture or a cell homogenate with neuraminidase, recombinant α1,3galactosyltransferase and uridine diphosphate galactose (UDP-Gal). The '675 patent does not contemplate an intratumoral injection of a mixture of neuraminidase, recombinant α1,3galactosyltransferase, and uridine diphosphate galactose to create an in situ autologous tumor vaccine.

Alternatively, α-gal epitopes can be inserted in vitro into a tumor cell membrane by incubation with α-gal glycolipids. The co-incubation of tumor cells or tumor cell membranes with such α-gal glycolipids results in their spontaneous in vitro insertion into the tumor cell membranes and the expression of α-gal epitopes on these membranes. The autologous tumor cells or cell membranes expressing α-gal epitopes can then be used as autologous tumor vaccines. Following their intradermal injection, the natural anti-Gal IgG antibody binds in situ at the vaccination site, to the α-gal epitopes on the vaccinating tumor cell membrane and target the vaccine to antigen presenting cells. Although it is not necessary to understand the mechanism of an invention, it is believed that the binding of the Fc portion of the complexed anti-Gal to Fcγ receptors on antigen presenting cells induces effective uptake of the opsonized vaccinating tumor cell membranes into antigen presenting cells. (See FIG. 4). Thus, the uncharacterized tumor antigens of the autologous tumor are also internalized into the antigen presenting cells. After transport of vaccinating autologous tumor membranes to the draining lymph nodes, the antigen presenting cells process and present the tumor antigen peptides for activation of tumor specific cytotoxic and helper T cells (i.e., $CD8^+$ and $CD4^+$ T cells, respectively).

A proof of principle for the efficacy of tumor vaccines expressing α-gal epitopes was achieved in studies in a mouse experimental model immunized with melanoma cells expressing α-gal epitopes and challenged with the same melanoma cells which, however, lack α-gal epitopes (LaTemple D C, Abrams J T, Zhang S U, Galili, U. *Cancer Res.* 1999, 59: 3417-23, and Deriy L, Ogawa H, Gao G, Galili U. *Cancer Gene Therapy* 2005; 12: 528-39). The mice used in those studies were knockout mice for the α1,3galactosyltransferase gene (i.e., these mice lack the α-gal epitope and can produce the anti-Gal antibody). Mice immunized with melanoma cells engineered to express α-gal epitopes displayed an effective immune protection against challenge with the same tumor cells, which however lack α-gal epitopes. In contrast, mice immunized with tumor cells lacking α-gal epitopes, did not display a protective immune response against challenge with the live tumor cells lacking α-gal epitopes.

III. α-Gal Glycolipids in Tumor Therapy

Previous studies have shown that in vitro transduction of human tumor cells with the α1,3galactosyltransferase gene within a replication deficient adenovirus vector results in subsequent expression of α-gal epitopes on the tumor cell membranes and that this expression peaks within 48 h post transduction (Deriy L, Chen Z C, Gao G P, Galili. *Glycobiology* 2002, 12: 135-44). In one embodiment, the present invention contemplates that α-gal glycolipids or a vector containing the α1,3galactosyl-transferase gene may be administered by injection, or by any other technology, directly into the tumor lesion. Although it is not necessary to understand the mechanism of an invention, it is believed that an in vivo intratumoral delivery of the α-gal glycolipids, or of an α1,3galactosyltransferase gene, results in the expression of α-gal epitopes on the tumor cells within the treated tumor. The subsequent binding of anti-Gal antibody to the α-gal epitopes displayed on the tumor cell membranes either by α-gal glycolipids or by gene therapy results in an intratumoral inflammation that destroys the tumor and converts the tumor into an in situ autologous tumor vaccine.

In one embodiment, the present invention contemplates the non-surgical treatment of solid tumor masses. Particular embodiments of the present invention contemplate novel immunotherapy treatments of cancer patients that aim to immunize the individual patient against his or her own tumor lesions by conversion of the patient's own tumor into an autologous tumor vaccine. (Galili et al., "Compositions and methods for vaccines comprising α-galactosyl epitopes" U.S. Pat. No. 5,879,675 (herein incorporated by reference)). For example, the '675 patent teaches an in vitro processing of tumor cells and/or cell membranes. Upon injection of these cells into a patient the vaccine is targeted by anti-Gal antibody to APCs and elicits a protective immune response against an autologous tumor antigens. Unlike the present invention, however, the '675 patent does not teach: i) an in vivo intratumoral treatment for the induction of inflammation, regression and/or destruction of the tumor by the natural anti-Gal antibody; ii) the display of α-gal epitopes on tumor cells in vivo following an intratumoral injection of α-gal glycolipids within cancer patients; iii) gene therapy of tumor lesions using α1,3galatosyl-transferase genes within the cancer patient; and iv) an in vivo injection of a mixture of α1,3galactosyltransferse, neuraminidase, and uridine diphosphate galactose for in situ conversion of the lesions into autologous tumor vaccines.

In one embodiment of the present invention α-gal glycolipids or the α1,3galactosyl-transferase gene may be delivered into a tumor lesion comprising tumor cells by a non-surgical intratumoral injection (i.e., for example, by endoscopy, catheterization, or the like), or by a "gene gun" or by any other method for in vivo introduction into tumors of the α-gal glycolipids, or anti-Gal binding epitopes on various molecules, or the α1,3galactosyltransferase gene or by gene(s) encoding an enzyme for production anti-Gal binding epitopes, or by the injection of enzymes that synthesize anti-Gal binding epitopes within the tumor lesion.

Post surgery recurrence of chemotherapy refractory metastases, is believed the most common cause of death in patients with solid tumors. High incidence of such relapsing metastases (~80%) have been reported in patients with pancreatic and ovarian carcinomas and to somewhat lesser extent in other solid tumors such as melanoma and colorectal, lung and breast carcinoma. Many of these relapsing patients are considered to have terminal disease, as no treatment is available for them, and they die within weeks or months after detection of the metastases.

In one embodiment, the present invention contemplates a therapeutic method for regression and/or destruction of solid tumor metastases by exploiting the fact that all humans, naturally produce the anti-Gal antibody as 1% of their immunoglobulins. The immunological potential of the anti-Gal antibody can be harnessed to regress and/or destroy any tumor metastases by converting them into an in situ autologous tumor vaccine by intratumoral injection of glycolipids carrying the α-gal epitope (i.e., for example, an α-gal glycolipid).

α-Gal glycolipids may be obtained from natural sources such as, but not limited to rabbit red blood cell membranes or bovine red blood cell membranes. In general, α-Gal glycolipids are characterized as a group of glycosphingolipids (GSL) comprised of a ceramide lipid tail and carbohydrate chains of various sizes. Usually, the α-gal epitope is represented as a terminal carbohydrate structure. Ceramide pentahexoside (CPH) is an α-gal glycolipid with 5 carbohydrate units and is an abundant neutral glycolipid in either rabbit red blood cell membranes or bovine red blood cell membranes (i.e., for example, cow) (See FIGS. 1A & 1B). (Galili et al. *Proc. Natl. Acad. Sci. USA* 1987; 84: 1369-73). Incubation of α-gal glycolipids with cells results in the spontaneous insertion of these glycolipids into the outer leaflet of the membrane bilayer and the display of α-gal epitopes on the cell membrane surface. Any other molecule that has a natural or synthetic epitope capable of binding the natural anti-Gal antibody (i.e., for example, an anti-Gal binding epitope) may serve for harnessing the immunological potential of this antibody in order to regress and/or destroy the treated tumor lesions and convert these treated tumor lesions into an autologous tumor vaccine. The ability of α-gal glycolipids to achieve such effects on the treated tumor is described below.

The α-gal glycolipids extracted from rabbit red blood cell membranes are soluble in aqueous solutions in the form of micelles (See FIG. 2). When α-gal glycolipids are injected into tumor lesions they can interact with the natural anti-Gal antibody and may induce extensive inflammatory reactions within the lesion. Although it is not necessary to understand the mechanism of an invention, it is believed that the inflammation is a result of an extensive local activation of complement.

Many α-gal glycolipids will spontaneously insert into the tumor cell membranes, since the hydrophobic (i.e. lipophilic) lipid tail of the α-gal glycolipids is in a more stable energetic form when embedded in the outer leaflet of the lipid bilayer of the cell membrane as compared to a water-surrounded micellular core (See FIG. 2). Spontaneous insertion (incorporation) of other types of glycolipids called gangliosides into cell membranes has been previously demonstrated (Kanda S, Inoue K, Nojima S, Utsumi H, Wiegandt H. *J Biochem* (Tokyo). 1982; 91: 1707-18, and Spiegel S, Yamada K M, Hom B E, Moss J, Fishman P H. *J. Cell Biol.* 1985; 100: 721-26). The insertion of α-gal glycolipids into the tumor cell membranes is expected to result in the de novo display of α-gal epitopes on the cell membrane surface. α-Gal epitope expression may facilitate an anti-Gal antibody mediated regression and/or destruction of the tumor cells by such mechanisms which include, but are not limited to, complement mediated cytolysis (CDC) and antibody dependent cell mediated cytolysis (ADCC) (See FIGS. 3B & 3C, respectively). An anti-Gal opsonized tumor cell membrane will then be effectively target antigen presenting cells, thereby converting the treated tumor lesions into autologous tumor vaccines. This autologous vaccine will then stimulate the immune system to react against tumor antigens resulting in the further regression and/or destruction of tumor cells expressing these antigens within other solid tumors and/or micrometastases of the treated patient (See FIG. 4).

In yet another embodiment, such a treatment may be performed as neo-adjuvant therapy, several weeks prior to resection of the primary tumor. In one embodiment, an intratumoral injection of α-gal glycolipids, or of other anti-Gal binding molecules, decreases the size of the tumor and converts the treated tumor into an autologous tumor vaccine. Although such a tumor will be eventually resected, it is believed that prior to its resection the treated tumor will elicit an immune response against micrometastases that display the same tumor antigens.

Other embodiments of the present invention include, but are not limited to, other carbohydrates capable of binding the natural anti-Gal antibody to effect opsonization of an antigen. In one embodiment, melibiose, and like carbohydrates, may bind anti-Gal to effect opsonization. In one embodiment, synthetic α-gal epitopes, and like carbohydrate structures, may include synthetic, or naturally occurring, carbohydrate chains containing α-gal epitopes, any other carbohydrate epitopes, or peptides mimicking α-gal epitopes in their ability to interact with the anti-Gal antibody (Sandrin M S, Vaughan H A, Xing P X, McKenzie I F. Glycoconj J. 1997; 14: 97-105). In addition, another embodiment of the present invention includes anti-Gal binding epitopes such as, but not limited to, carbohydrate epitopes, or mimicking peptides capable of interacting with the anti-Gal antibody and which have chemical reactive groups that link them to cell membranes within the treated tumor. In another embodiment, the present invention includes synthetic and natural glycoconjugates that carry α-gal epitopes and other anti-Gal binding epitopes capable of interacting with the anti-Gal antibody and thus can induce an inflammatory response when injected into tumor lesions.

Various types of synthetic and natural α-gal epitopes on glycolipids and glycoproteins are commercially available and useful in the present invention, including, but not limited to: i) Galα-3Gal glycolipids: α1-3 galactobiose (G203); linear B-2 trisaccharide (GN334); and Galili pentasaccharide (L537); and ii) Glycoconjugates: Galα1-3Galβ1-4Glc-BSA (NGP0330); Galα1-3Galβ1-4(3-deoxyGlcNAc)-HSA (NGP2335); Galα1-3Galβ1-4GlcNAcβ1-HDPE (NGL0334); Galα1-3Gal-BSA (NGP0203) (Dextra Laboratories, Ltd. Reading, United Kingdom). Additional examples of available synthetic glycoconjugates which are polymeric forms of α-gal epitopes are GAS914, produced by Novartis (Zhong R, Luo Y, Yang H. et al. *Transplantation.* 2003; 75: 10), or TPC, an α-gal polyethylene glycol conjugate (Schirmer J M, Fass D N, Byrne G W, et al. *Xenotransplantation.* 2004; 11: 436). These compounds, and similar synthetic and natural glycoconjugates or oligosaccharides linked to reactive groups having anti-Gal binding epitopes, may also elicit an anti-Gal antibody mediated intratumoral inflammation and conversion of the treated tumor lesion into an in situ autologous tumor vaccine following an intratumoral injection.

IV. Mechanisms of Anti-Gal Antibody Tumor Regression and/or Destruction

U.S. Pat. No. 5,879,675 is limited to the in vitro expression of α-gal epitopes on tumor cells or tumor cell membranes. In one embodiment, the present invention contemplates using α-gal glycolipids as an oncological drug that is injected in vivo into at least one tumor lesion of a patient. Although it is not necessary to understand the mechanism of an invention, it is believed that injection of α-gal glycolipids into tumor lesions induce an extensive intratumoral inflammation, regression and/or destruction of the treated tumor lesion and induction of a systemic protective anti-tumor immune response, capable of regressing and/or destroying micrometastases. In one embodiment, the α-gal glycolipids is injected in a pharmaceutically acceptable solution (i.e., for example, sterile) selected from the group including, but not limited to, phosphate buffer saline (PBS), saline, or other aqueous solutions. In one embodiment, the solution of α-gal glycolipids may also contain deoxycholate, or other mild detergents that may increase penetration of the glycolipids into cell membranes.

Although it is not necessary to understand the mechanism of an invention, it is believed that tumor lesion regression and/or destruction by the injected α-gal glycolipids may comprise a biochemical and physiological basis as discussed below (See FIG. 3 and FIG. 4).

Induction of Inflammation within the Tumor Lesion

An intratumoral injection may result in a local rupture of tumor associated capillaries thereby providing natural anti-Gal IgM and/or anti-Gal IgG antibody molecules access to the tumor interior. Anti-Gal antibodies would then be able to interact with the α-gal epitopes on α-gal glycolipid micelles, or individual α-gal glycolipids molecules, thereby inducing local activation of complement and generation of the complement cleavage chemotactic factors C5a and C3a. (See FIG. 3A). Complement activation then initiates a local inflammatory process facilitating intratumoral granulocytes and monocyte migration directed by the de novo produced C5a and C3a chemotactic factors within the treated tumor lesions. The inflammatory process is further amplified as a result of the insertion of α-gal glycolipids into cell membranes causing an anti-Gal activation of endothelial cells (Palmetshofer A, Galili U, Dalmasso A P, Robson S C, Bach F H. *Transplantation.* 1998; 65: 844-53; Palmetshofer A, Galili U, Dalmasso A P, Robson S C, Bach F H. *Transplantation.* 1998; 65: 971-8). Endothelial cell activation and overall tumor cell damage may result in local production of additional pro-inflammatory cytokines and chemokines. These locally secreted cytokines and chemokines induce migration of macrophages, dendritic cells, and subsequently migration of lymphocytes into the lesion injected with α-gal glycolipids. This cellular migration is mediated by receptors to pro-inflammatory cytokines and chemokines on antigen presenting cells and on lymphocytes (Cravens P D, Lipsky P E *Immunol Cell Biol.* 2002; 80: 497-505). This initial induction of an inflammatory response enables the immune system to overcome its general lack of ability to detect the "stealthy nature" of developing tumor lesions. This inflammation also enables the immune system to overcome the immunosuppressive microenvironment within solid tumor lesions that is induced by the local cytokine milieu, and which normally prevent lymphocytes from penetrating into the tumor (Malmberg K J. *Cancer Immunol Immunother.* 2004; 53: 879-92; Lugade A A, Moran J P, Gerber S A, Rose R C, Frelinger J G, Lord E M. *J Immunol.* 2005; 174:7516-23).

Destruction of the tumor cells by anti-Gal binding to α-gal glycolipids inserted into cell membranes. α-gal glycolipids injected into a tumor may spontaneously insert into the outer leaflet of the phospholipid bilayer of tumor cell membranes via the lipophilic ceramide tail of α-gal glycolipids. (See FIG. 2). The subsequent binding of anti-Gal IgM and/or anti-Gal IgG to the α-gal epitopes on the inserted α-gal glycolipid induces the regression and/or destruction of the treated tumor via complement dependent cytolysis (CDC) (See FIG. 3B). The binding of anti-Gal IgG molecules to these α-gal epitopes also facilitates antibody dependent cell cytolysis (ADCC) of the tumor cells (See FIG. 3C).

In complement dependent cytolysis, anti-Gal IgM molecules binding to tumor cells expressing α-gal epitopes (due to α-gal glycolipid insertion) activate the complement system. Subsequently, the complement $C_{5-9}$ membrane attack complex formed as a result of this complement activation, then "pokes" holes in the tumor cell membranes, resulting in tumor cell lysis. This complement dependent cytolysis is similarly found when pig endothelial cells are lysed, leading to hyperacute rejection of xenografts (Collins B H, Cotterell A H, McCurry K R, Alvarado C G, Magee J C, Parker W, Platt J L. *J. Immunol.* 1995; 154: 5500-10,). In ADCC the effector cells are granulocytes, macrophages, and NK cells. These cells are attracted to the lesion because of the anti-Gal induced inflammatory process. They bind via their Fcγ receptors (FcγR) to the Fc portion of anti-Gal IgG molecules which are bound to the α-gal glycolipid inserted into the tumor cell membrane. Once attached to the tumor cells, these effector cells secrete their granzyme vesicles into the membrane contact areas generating holes in the tumor cell membrane, thus inducing the destruction of these tumor cells. The efficacy of anti-Gal IgG in inducing ADCC destruction of cells expressing α-gal epitopes was demonstrated with xenograft pig cells binding anti-Gal via their α-gal epitopes (Galili, U. *Immunol.*

Today 1993, 14: 480-82). A similar anti-Gal mediated ADCC process occurs when tumor cells bind anti-Gal via α-gal epitopes expressed on their cell surface membrane (Tanemura M, Yin D, Chong A S, Galili U. *J. Clin. Invest.* 2000; 105: 301-10).

Anti-Gal mediated targeting of tumor cell membranes to antigen presenting cells for the induction of a systemic protective anti-tumor immune response. The uptake of tumor cell membranes by antigen presenting cells may result in an induction of a protective immune response against autologous tumor antigens in order to regress and/or destroy chemotherapy refractive micrometastases. Anti-Gal IgG antibody bound to α-gal epitopes on membrane inserted α-gal glycolipids stimulates antigen presenting cells to internalize cell membranes expressing the tumor antigens (i.e., for example, tumor associated antigens, TAAs) (See FIG. 4). The internalized tumor antigens can then be transported by the antigen presenting cells from the treated tumor lesion to the draining lymph nodes. These tumor antigens may then be further processed by the antigen presenting cells and presented as immunogenic tumor peptides that activate tumor specific T cells. This process results in the induction of a systemic protective anti-tumor immune response (i.e., for example, an autologous tumor vaccine). Therefore, tumor lesions injected with α-gal glycolipids ultimately are converted into in situ autologous tumor vaccines that elicit an immune response against micrometastases expressing the tumor antigens as those in the treated tumor lesions.

As a clinical treatment modality, α-gal glycolipids can be administered into cancer lesions by various methods including, but not limited to, an intradermal injection (i.e., for example, into a melanoma tumor); an endoscopic injection (i.e., for example, into colorectal intestinal metastases); a laparoscopic injection (i.e., for example, into abdominal ovarian, colon, gastric, liver, or pancreatic carcinoma metastases (e.g. on the peritoneum or in the liver)); a transcutaneous imaging guided needle injection (i.e., for example, into lung tumors); or a cystoscopic injection (i.e., for example, into urinary bladder carcinomas).

In one embodiment, the present invention contemplates an intratumoral injection of α-gal glycolipids into primary tumors as a neo-adjuvant therapy provided before tumor resection surgery. In one embodiment, a rapid inflammatory response induced by the pre-surgical injection by an α-gal glycolipid result in decreasing the tumor lesion size, as well as converting it into an in situ autologous tumor vaccine. Although it is not necessary to understand the mechanism of an invention, it is believed that the immune response to the treated tumor may ultimately help to induce the immune destruction of micrometastases that are not detectable at the time of surgical resection of primary tumors. It is further believed that pre-surgical administration may help in preventing recurrence of the disease due to immunological destruction of micrometastases resistant to conventional adjuvant therapy (i.e., for example, chemotherapy and radiation) and which express tumor antigens as does the primary tumor. Such neo-adjuvant therapy may be administered to any solid tumor or lymphoma that can be injected directly, or by guided imaging, or any other known method.

V. Gene Therapy

According to one embodiment, the present invention contemplates an intratumoral injection of AdαGT resulting in the expression of α-gal epitopes on the transduced tumor cells. In one embodiment, an inflammatory response is induced following binding of anti-Gal antibodies to these de novo α-gal epitopes. In one embodiment, the anti-Gal/α-gal epitope binding results in the regression and/or destruction of the treated tumor lesion. In another embodiment, the anti-Gal/α-gal epitope binding converts the treated tumor lesion into an autologous tumor vaccine.

In one embodiment, the present invention contemplates anti-Gal antibody mediated regression and/or destruction of tumors by injection of vectors comprising a α1,3galactosyltransferase gene. In one embodiment, the present invention contemplates a method of treating melanoma patients with multiple metastases comprising intratumoral injections of an adenovirus comprising an α1,3galactosyltransferase gene (i.e., for example, AdαGT). In one embodiment, an intratumoral injection of AdαGT results in transduced tumor cells expressing α-gal epitopes, wherein these tumor cells display the α-gal epitopes on the cell membrane surface and induce intratumoral inflammation after binding with anti-Gal antibody. In one embodiment, the transduced tumor cells are further destroyed by complement dependent cytolysis (CDC). In another embodiment, the transduced tumor cells are further destroyed by an antibody dependent cell mediated cytolysis (ADCC). (See FIG. 3) Although it is not necessary to understand the mechanism of an invention, it is believed that the anti-Gal antibody opsonized tumor membranes within the treated lesion will be targeted to antigen presenting cells serving as an effective autologous tumor vaccine (See FIG. 4).

In another embodiment, the present invention contemplates a method of treating colorectal carcinoma patients having multiple metastases in the colon and in the liver comprising intratumoral injections of AdαGT. In one embodiment, the injection comprises colonoscopy or laparoscopy as means of delivering the viral vector into the tumor lesions.

In yet another embodiment, the present invention contemplates a method of treating lung carcinoma patients having multiple metastases in the lungs comprising intratumoral injections of AdαGT. In one embodiment, the injection comprises bronchoscopy.

In another embodiment, the present invention contemplates a method of treating patients with urinary bladder carcinoma comprising an AdαGT viral vector. In one embodiment, the vector is administered by means of cystoscopy.

In another embodiment, the present invention contemplates a method of treating patients with pancreatic adenocarcinoma comprising an AdαGT viral vector. In one embodiment, the vector is administered by means of endoscopy or laparoscopy.

Administration of an AdαGT viral vector can be performed in any solid tumor or lymphoma that is accessible to intratumoral delivery of the α1,3galactosyltransferase gene.

Alternative methods to deliver the α1,3galactosyltransferase gene can be performed also with any type of viral and non-viral vector which can deliver genes. For example, these methods include, but are not limited to adenovirus vector, adenovirus helper virus, retrovirus vector, lentivirus vector, naked DNA vectors, or naked RNA vectors.

In another embodiment, the present invention contemplates a method to administer vectors containing the α1,3galactosyltransferase gene by injection into melanoma lesions or any other tumor lesion, whereby the epitopes insert into the tumor cell membranes. As in the case of tumor cells transduced with AdαGT, the anti-Gal IgG will bind to the tumor cell membranes expressing α-gal epitopes and will target them to antigen presenting cells for eliciting a systemic immune response also against nontreated tumor lesions that express the tumor antigens. One of skill in the art should recognize the present invention contemplates conversion of the tumor lesions into autologous tumor vaccines targeted by anti-Gal to antigen presenting cells by any composition introduced into the tumor mass that results in the in situ binding of this natural antibody to the tumor cells.

VI. Intratumoral Introduction of α1,3Galactosyltransferase and Neuramimidase

One embodiment of the present invention contemplates anti-Gal mediated regression and/or destruction of tumors by intratumoral injection with recombinant α1,3galactosyltransferase. In one embodiment, the present invention contemplates a method of treating cancer patients with multiple metastases by intratumoral injections of a solution comprising a recombinant α1,3galactosyltransferase. In one embodiment, a recombinant α1,3galactosyltransferase is produced in the expression system of yeast *Pichia pastoris* transformed by an α1,3galactosyltransferase gene (Chen Z C, Tanemura M, Galili U. *Glycobiology* 2001; 11: 577-86). In one embodiment, a solution comprising α1,3galactosyltransferase (0.01 μg-10 mg), neuraminidase (0.001 mUnits-1000 Units) and uridine diphosphate galactose (UDP-Gal) (0.001-100 mM) is injected into the one or more tumor lesions. Although it is not necessary to understand the mechanism of an invention, it is believed that this results in the synthesis of α-gal epitopes on the cell membranes within the treated one or more tumor lesions according to the following enzymatic reactions:

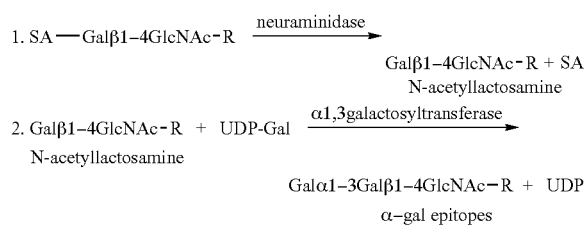

In Reaction 1, sialic acid (SA) can be removed from the carbohydrate chains by neuraminidase to expose the penultimate N-acetyllactosamine residues (Galβ1-4GlcNAC-R) on the cell surface carbohydrate chains. The N-acetyllactosamines exposed on the carbohydrate chains can then function as an acceptor for α1,3galactosyltransferase providing a link to terminal α1-3galactosyl residues thereby forming α-gal epitopes. (See FIG. 21). In one embodiment, the sugar donor providing galactose to α1,3galactosyltransferase is uridine-diphosphate galactose (UDP-Gal). The same reaction pathway occurs also when the N-acetyllactosamine is of the structure Galβ1-3GlcNAc-R.

This synthetic pathway for α-gal epitopes may also occur either in vitro within cells. (See FIG. 22). In one embodiment, an intratumoral injection of a solution comprising α1,3galactosyltransferase, neuraminidase, and uridine diphosphate galactose (UDP-Gal) results in display of α-gal epitopes on tumor cell membranes thereby inducing intratumoral inflammation after binding an anti-Gal antibody. Although it is not necessary to understand the mechanism of an invention, it is believed that these cells are further destroyed by the natural anti-Gal antibody bound to α-gal epitopes on the transduced cells via the complement dependent cytolysis (CDC) or antibody dependent cell mediated cytolysis (ADCC) mechanisms (See FIG. 3). It is further believed that the anti-Gal opsonized tumor membranes will be targeted to antigen presenting cells and serve as an effective autologous tumor vaccine. (See FIG. 4).

The α1,3galactosyltransferase can by obtained from any mammalian source and produced in any expression system. Likewise, neuraminidase can be obtained from any source provided that it can cleave sialic acid from carbohydrate chains (i.e., for example, Sigma, Cat. No. N7885, *Vibrio cholera*, St. Louis Mo.) The buffer used for the enzyme solution can be any buffer enabling the activity of these two enzymes. For example, one buffer in which the activity of these enzymes was demonstrated was an enzyme buffer containing 0.1M MES (methylethylsulfonate) pH 6.0, and 25 mM $MnCl_2$ (Chen Z C, Tanemura M, Galili U. *Glycobiology*. 2001; 11: 577-86). In various types of tumors there may be many carbohydrate chains with terminal N-acetyllactosamines that are not capped by sialic acid. The α-gal epitope may be synthesized on such carbohydrate chains in the absence of neuraminidase. Nevertheless, inclusion of neuraminidase in the solution introduced into the tumor will increase the number of N-acetyllactosamines on which α-gal epitopes are synthesized by α1,3galactosyltransfersase.

EXPERIMENTAL

The following examples are intended only as illustrative examples of embodiments of the present invention. They are not to be considered as limiting the present invention.

Example 1

Extraction of α-Gal Glycolipids from Rabbit and Bovine Red Blood Cell Membranes

Figure 1C:
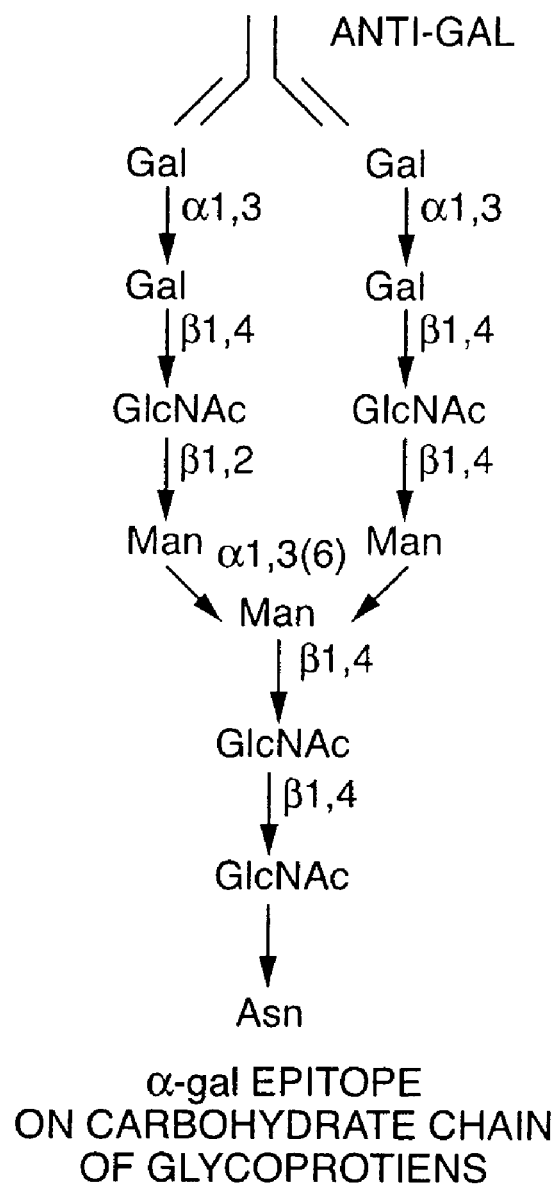

A rich source for α-gal glycolipids is rabbit red blood cells. The two major glycosphingolipids (GSL), i.e. glycolipids with ceramide tail, in rabbit red blood cell membranes are ceramide (Cer) trihexoside (CTH, with 3 sugars [hexoses], present also in human red blood cells) with the structure Galα1-4Galβ1-4Glc-Cer and ceramide pentahexoside (CPH, with 5 sugars [hexoses]) with α-gal epitopes as terminal part of the CPH structure of Galα1-3Galβ1-4GlcNAcβ1-3Galβ1-4Glc-Cer (Eto T, Iichikawa Y, Nishimura K, Ando S, Yamakawa T *J. Biochem.* (Tokyo) 1968; 64: 205-13, and Stellner K, Saito H, Hakomori S. *Arch. Biochem. Biophys.* 1973; 133: 464-72) (See FIG. 1 and FIG. 6A, lane 1). Immunostaining of rabbit α-gal glycolipids on thin layer chromatography (TLC) plates with human natural anti-Gal resulted in binding of the antibody to CPH but not to CTH (See FIG. 6A, lane 2). This immunostaining revealed also that glycolipids with longer carbohydrate chains with α-gal epitopes bind anti-Gal, but migrate less than CPH because of their length.

Relatively large amounts of α-gal glycolipids were extracted from one liter of rabbit red blood cells. The red cell membranes were obtained by lysing the red blood cells with hypotonic shock in water and the membranes washed to remove the hemoglobin. The glycolipids, cholesterol and phospholipids were extracted by mixing ~140 gm of the rabbit red blood cell membranes with 600 ml chloroform and 300 ml methanol (chloroform:methanol 1:2) for 2 hours, addition of 300 ml methanol for 2 hours extraction in chloroform:methanol 1:1 and addition of methanol to a total volume of 1600 ml for overnight extraction. Extraction of glycolipids is not limited to this procedure and may be achieved by chloroform and methanol, or other solvents. In the described method, all proteins were denatured and removed by filtration through Whatman paper.

Gradual addition of 400 ml pyrogen free sterile, distilled water resulted in partitioning into approximately 500 ml of a lower organic phase containing most of the chloroform and approximately 1500 ml of an upper aqueous phase containing most of the water. Methanol was present in both phases. The lower organic phase was highly lipophilic (i.e. hydrophobic) and contained the membrane phospholipids and cholesterol (both hydrophobic molecules). Most of the CTH preferentially remained in the organic phase because the hydrophobicity of the ceramide tail (See FIG. 6B). A portion of CPH was also retained in the lower organic phase (See FIG. 6B). The upper aqueous phase was hydrophilic and contained much of the CPH and α-gal glycolipids with longer carbohydrate chains, due to the hydrophilic characteristics of the carbohydrate chains with ≧7 sugar units (See FIG. 6B). Many of these long chain glycolipids were present in the bands beneath the CPH band of the aqueous phase (See FIG. 6B). These bands include, but are not limited to, glycolipids with 7, 10, 15 and even 30 carbohydrate forming carbohydrate chains that were previously shown to have terminal α-gal epitopes (Dabrowski U, Hanfland P, Egge H, Kuhn S, Dabrowski J. *J Biol. Chem.* 1984 25; 259: 7648-51 and Honma K, Manabe H, Tomita M, Hamada A. 1981; 90: 1187-96) and thus, they readily bind anti-Gal. (See FIG. 6A). Note that the aqueous phase was devoid of phospholipids and cholesterol (i.e. was phospholipids-free and cholesterol-free). The methanol and traces of chloroform were removed from the upper aqueous phase in a rotary evaporator, the α-gal glycolipids were concentrated in water to 30 mg/ml. The α-gal glycolipids fully dissolved in aqueous solution creating a solution of micelles. (See FIG. 2).

Extracted rabbit red blood cell α-gal glycolipids were fractionated by high pressure liquid chromatography (HPLC) and stained on TLC plates with a monoclonal anti-Gal antibody. The separation demonstrated a CPH with a 5 carbohydrate chain, as well as CHH (ceramide heptahexoside) with a 7 carbohydrate chain and a biantennary ceramide decahexoside (Cdeca) with 10 carbohydrate chains, all with terminal α-gal epitopes (See FIGS. 6C & 6D) (Buehler J, Galili U, Macher B A. *Anal Biochem.* 1987; 164: 521-25). The α-gal glycolipid also included molecules with more than 10 carbohydrates (See FIG. 6A, lane 2, low band; and FIG. 6B, aqueous phase lane, low band) (Dabrowski U, Hanfland P, Egge H, Kuhn S, Dabrowski J. *J Biol. Chem.* 1984; 259: 7648-51). These long chain glycolipids included also α-gal glycolipids with 15 carbohydrate units (i.e., for example, Cpentadeca comprising three antennae and Cdeca comprising two antennae), and longer chain α-gal glycolipids with an average of 30 carbohydrates reported to be present in these red blood cells as "mega-glycolipids" (Honma K, Manabe H, Tomita M, Hamada A. *J Biochem* (Tokyo). 1981; 90: 1187-96). These types of compounds have been characterized by NMR using rabbit red blood cell glycolipids (Dabrowski U, Hanfland P, Egge H, Kuhn S, Dabrowski J. *J Biol. Chem.* 1984; 259: 7648-51). This preparation of α-gal glycolipids from rabbit red blood cells contained approximately $2 \times 10^{16}$ α-gal epitopes per mg of glycolipids.

The use of α-gal glycolipids in the clinical setting may require much more material than that isolated from rabbit red blood cell membranes. The logistic limitations in supplies of large amounts of rabbit red blood cells can be overcome by the use of bovine red blood cells (i.e., for example, cow) instead of rabbit red blood cells since there is no practical limit to the amounts of bovine blood which can be supplied for preparation of α-gal glycolipids. Bovine red blood cells are suitable for α-gal glycolipids extraction since they contain CPH, CHH and α-gal glycolipid with longer carbohydrate chains (Uemura K, Yuzawa M, Taketomi T. *J Biochem* (Tokyo). 1978; 83: 463-71, and Chien J L, Li S C, Li Y T. *J Lipid Res.* 1979; 20: 669-73). Immunostaining of α-gal glycolipids extracted from bovine red blood cells demonstrated the abundance of CPH, CHH and long chain glycolipids with α-gal epitopes which readily interact with anti-Gal (See FIG. 7). Because bovine red blood cell glycolipids include many gangliosides (i.e. glycolipids with terminal sialic acid groups), preparation of α-gal glycolipids from these red blood cell membranes may require an additional step of removal of the gangliosides by the use of DEAE-Sephadex, DEAE-Sepharose columns, or any other method known in the art.

Example 2

Binding of Autologous Anti-Gal to Cells with Inserted α-gal Glycolipids and Subsequent Complement Mediated Lysis of Such Cells Insertion of α-gal glycolipids into autologous cell membranes can be demonstrated by incubation of human red blood cells with 1 mg/ml of α-gal glycolipids for 2 h at 37° C. After extensive washing to remove unbound α-gal glycolipids, the expression of α-gal epitopes can be demonstrated by the incubation of the red blood cells with heat inactivated autologous serum that was diluted 1:2 in phosphate buffered saline (PBS). The binding of autologous anti-Gal to the inserted α-gal glycolipids was demonstrated by incubation of these red blood cells with phycoerythrin coupled anti-human IgG and analysis of staining by flow cytometry. The bound antibodies was indicated by the shift in binding of IgG antibodies in comparison with control untreated red blood cells (See FIG. 8A, thick line histogram and dotted line histogram, respectively). The antibodies binding to the α-gal glycolipids inserted to the red blood cell membranes have anti-Gal specificity as indicated by the elimination of binding when the red blood cells were incubated with the autologous serum that was depleted of anti-Gal (See FIG. 8A, closed histogram). This depletion was achieved by absorption of the serum on rabbit red blood cells that were fixed with glutaraldehyde. These data confirm that α-gal glycolipids become inserted into the red blood cell membranes to which anti-Gal antibody subsequently binds (See FIG. 2).

Figure 3B:
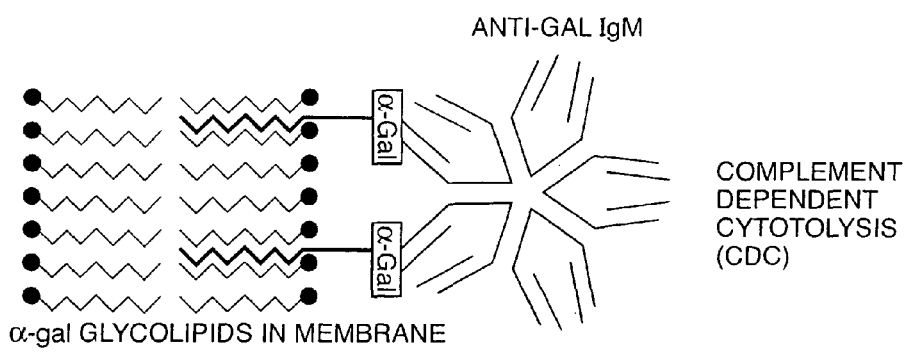
Figure 3C:
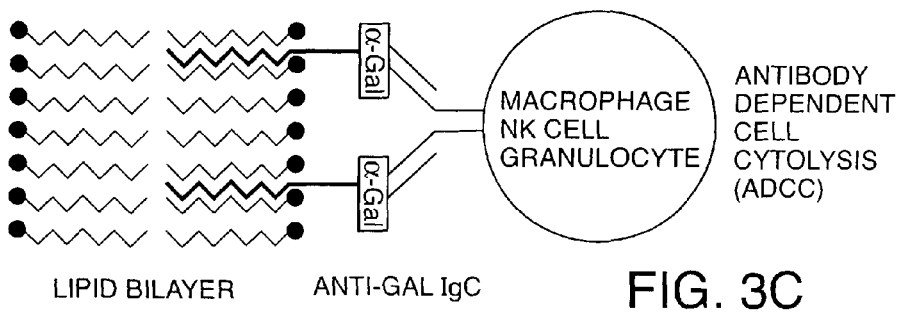

The binding of anti-Gal to α-gal epitopes on the cell membranes with embedded α-gal glycolipids may result in complement activation and lysis of the cells (See FIG. 3B). This could be demonstrated in the autologous system of human red blood cells incubated in the presence of α-gal glycolipids. (See FIG. 8A). The red blood cells were incubated at various concentrations of α-gal glycolipids and then further incubated with autologous serum at various dilutions of the serum. (See FIG. 8B). This incubation resulted in complement dependent cytolysis of the red blood cells treated with 0.1-1.0 mg/ml of α-gal glycolipids. When complement was inactivated by incubation of the serum at 56° C. no significant lysis was observed even at a serum dilution of 1:2 (See FIG. 8B). These findings indicate that one of the outcomes of α-gal glycolipids insertion into cell membranes is complement dependent cytolysis of the cells by anti-Gal. It is believed that a similar process in tumor lesions injected with α-gal glycolipids may result in regression and/or destruction of the tumor.

Example 3

Insertion of α-Gal Glycolipids into Tumor Cell Membranes and Subsequent Complement Mediated Lysis of Cells with the Inserted α-Gal Glycolipids This example demonstrates an in vitro mouse tumor model showing the insertion of α-gal glycolipids into tumor cell membranes and the subsequent binding of anti-Gal. This model utilizes B16 melanoma cells (mouse tumor cells lacking α-gal epitopes) that form tumor lesions in mice having an H-2b genetic background.

B16 cells in RPMI medium supplemented with 10% fetal calf serum were incubated with 1 mg/ml, 0.1 mg/ml, or 0.01 mg/ml of α-gal glycolipids for 2 h at 37° C. with constant rotation. After extensive washing to remove unbound α-gal glycolipids, the display of α-gal epitopes was demonstrated by binding mouse anti-Gal IgG purified on α-gal affinity column from serum of α1,3galactosyltransferase knockout mice that produce anti-Gal.

After 2 h incubation at 4° C. with the anti-Gal antibody the cells were washed and incubated with fluorescein coupled anti-mouse IgG. Anti-Gal binding was evaluated by flow cytometry (See FIG. 9A). Control B16 tumor cells did not bind anti-Gal. B16 melanoma cells, however, incubated with 1 mg/ml α-gal glycolipids readily bound anti-Gal because of α-gal epitope display on their cell membrane. The number of the inserted α-gal glycolipids is dose-dependent as indicated by the lower level of anti-Gal binding to B 16 cells incubated with 0.1 mg/ml of α-gal glycolipids and less binding after the B16 cell incubation with 0.01 mg/ml of α-gal glycolipids (See FIG. 9A). Nevertheless, even after incubation with 0.01 mg/ml of α-gal glycolipids, binding of anti-Gal was higher than the background level of anti-Gal binding to control untreated B16 cells, as indicated by the shift in the histogram (See FIG. 9A).

These findings support the conclusion that α-gal glycolipids spontaneously insert into the membrane of tumor cells incubated with α-gal glycolipid solution. (See FIG. 2). This insertion of α-gal glycolipids results in the subsequent binding of anti-Gal to the α-gal epitopes of the inserted glycolipids.

One of the outcomes of the interaction between anti-Gal and the α-gal glycolipids inserted into the tumor cell membranes is the activation of complement and induction of complement mediated cytolysis of the cells. (See FIG. 3B). This lysis was demonstrated with B16 cells with inserted α-gal glycolipids (See FIG. 9B). B16 cells incubated with 1 mg/ml of α-gal glycolipids were washed and then incubated for 2 h at 37° C. with mouse serum containing anti-Gal. The cells were then inspected for cell lysis by vital staining with Trypan blue. Cell lysis was readily observed even at a serum dilution of 1:16. (See FIG. 9B). This lysis was complement dependent as indicated by the fact that no such lysis was observed with heat inactivated serum.

Example 4

In Vivo Induction of a Local Inflammatory Response in Skin Injected with α-Gal Glycolipids The in vivo effect of α-gal glycolipid treatment on solid tumor lesions was studied in α1,3galactosyltransferase knockout mice in which syngeneic B16 melanoma cells grew into solid tumor lesions because both express major histocompatibility complex (MHC)H-2b antigens. α1,3Galactosyltransferase knockout mice are available as an experimental animal model in which anti-Gal mediated destruction of tumor injected with α-gal glycolipids can be evaluated. This is because the α-gal epitope synthesis in these mice is eliminated by disruption (i.e. knockout) of the α1,3galactosyltransferase gene (Thall A D, Maly P, Lowe J B. *J Biol. Chem.* 1995; 270: 21437-40). Because of lack α-gal epitopes, these mice respond by producing the anti-Gal antibody when immunized with xenogeneic membranes such as rabbit red blood cell membranes (LaTemple D C, Abrams J T, Zhang S U, Galili, U. *Cancer Res.* 1999, 59: 3417-23), or pig kidney membranes (Tanemura M, Yin D, Chong A S, Galili U. *J. Clin. Invest.* 2000; 105: 301-10).

The induction of inflammation due to the binding of anti-Gal to α-gal epitopes on α-gal glycolipids was demonstrated by injection of 1 mg α-gal glycolipids in a volume of 0.1 ml subcutaneously into anti-Gal antibody-producing α1,3galactosyltransferase knockout mice. The skin at the injection site is shaven prior to administration of α-gal glycolipids.

Figure 10A:
Figure 10B:
Figure 10C:
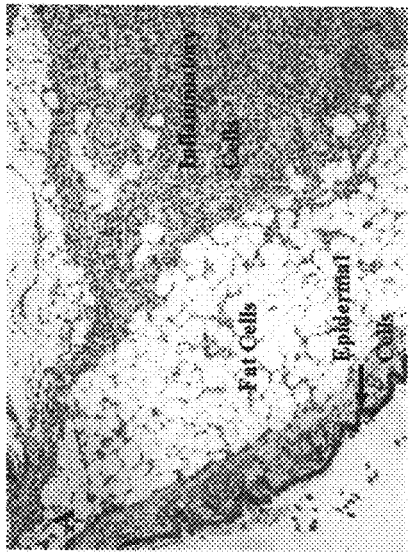
Figure 10D:
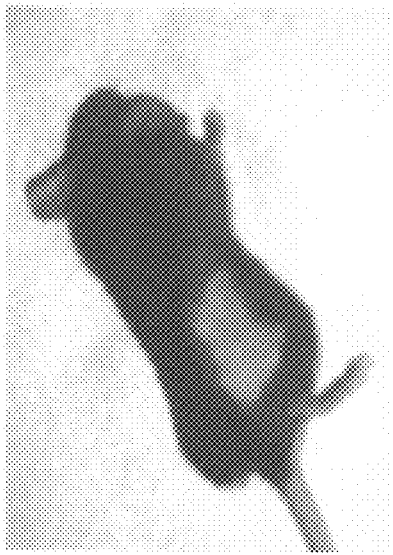

Within 4 days post injection extensive infiltration of inflammatory cells into the injection site was observed at the α-gal glycolipids injection site (See FIG. 10A). Although it is not necessary to understand the mechanism of an invention, it is believed that this inflammation is a result of anti-Gal antibody interaction with α-gal glycolipids and the activation of complement (See FIG. 3A). The infiltrates are comprised of neutrophils and monocytes/macrophages.

Control mice injected with physiologically buffer saline (PBS) displayed normal skin architecture without an inflammatory response (not shown). The various cytokines and chemokines secreted into the α-gal glycolipid injection site also stimulated the melanocytes to produce large amounts of melanin, as indicated by the black patch appearing on the skin one week post injection (See FIG. 10B). Although it is not necessary to understand the mechanism of an invention, it is believed that this stimulation of melanin production was the result of the induction of the local inflammatory reaction following interaction of α-gal glycolipids with the anti-Gal antibody, rather than a direct effect of α-gal glycolipid on melanocytes. This is indicated from the observation that subcutaneous injection of α-gal glycolipid in wild type mice (i.e. mice expressing α-gal epitopes on their cells and thus, incapable of producing anti-Gal antibody), resulted in no inflammation and no darkening of the skin at the injection site (See FIG. 10C). No skin damage or ulcerations were observed at the injection sites in α1,3galactosyltransferase knockout mice. The black color of the skin was gradually replaced by the normal pink color within 2-3 weeks (See FIG. 10D). After 3 additional weeks the black color of the skin completely disappeared and the shaven skin presents the normal pink color as in FIG. 10C.

Example 5

Effect of Intratumoral Injection of α-Gal Glycolipids on B16 Melanoma Tumor Lesion In order to demonstrate the effect of intratumoral injection of α-gal glycolipids, α1,3galactosyltransferase knockout mice (KO mice) were shaven in the right abdominal flank and injected subcutaneously with $1 \times 10^6$ B16 melanoma cells at two sites in the same flank.

On day 8 post subcutaneous injection of tumor cells, the tumors reached a diameter of 4-5 mm. One of the two tumors was injected with 1.0 mg of α-gal glycolipids in 0.1 ml phosphate buffer saline (PBS) and the second tumor injected with only 0.1 ml PBS and served as a control. Whereas the control tumors injected with PBS continued to grow, reaching the size of 15 mm within additional 10 days, many of the tumors injected with α-gal glycolipids stopped growing and displayed 30-50% decrease in size (i.e., for example, indicating tumor regression) 10 days after the α-gal glycolipids injection (See FIG. 11A). The representative mouse shown (one of 10 with similar results) had the front tumor injected with PBS and the back tumor injected with α-gal glycolipids. This differential effect is reproducible whether front or back tumors are treated with α-gal glycolipids.

Figure 11B:
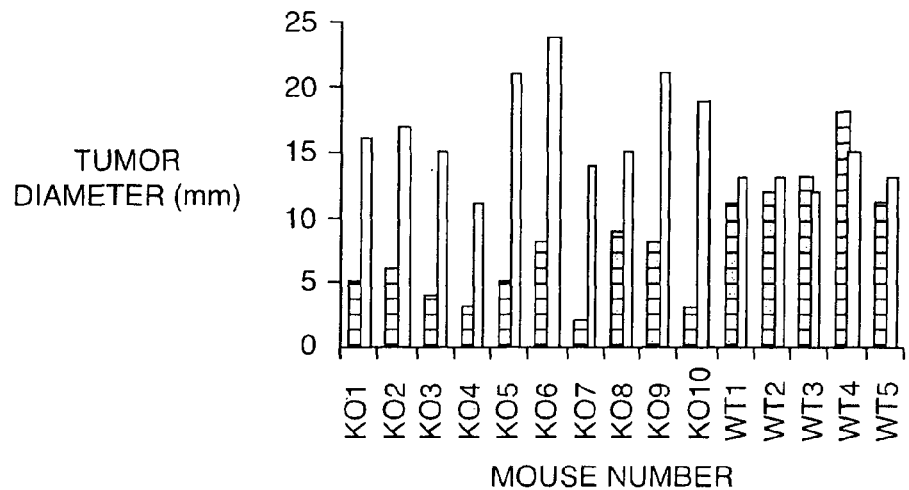

Tumor size from all ten mice (mean diameter from two measurements, perpendicular to each other), measured 10 days post injection of α-gal glycolipids or PBS is shown in FIG. 11B. The data show that tumors injected with α-gal glycolipids were much smaller than the corresponding control tumor injected with PBS in the same mouse indicating that tumor regression was in progress. No such differences were observed in five wild type (WT) mice undergoing similar treatment and lacking anti-Gal antibody (See FIG. 11B). This data allows the conclusion that the decreased size of tumors treated with α-gal glycolipids in α1,3galactosyltransferase knockout mice resulted from an interaction between anti-Gal and the injected α-gal glycolipids.

Figure 11C:
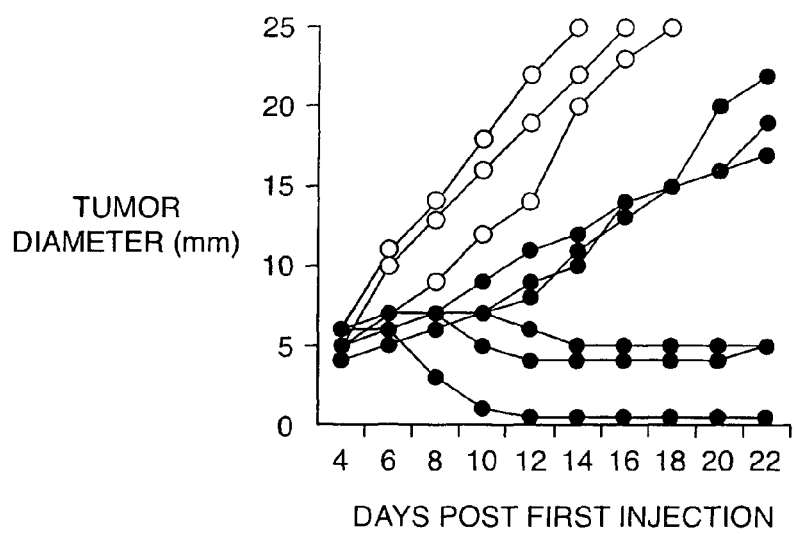

The time kinetics of tumor growth for periods longer than 10 days were monitored in eighteen α1,3galactosyltransferase knockout mice with individual tumors treated with α-gal glycolipids or with PBS (See FIG. 11C). The size of the control tumors increases very fast and reaches the maximal size of 25 mm within 14-18 days post PBS injection. In mice with tumors injected with α-gal glycolipids, some of the tumors did not develop at all, whereas others did develop at a much slower rate than that observed in tumors treated only with PBS.

In order to study the intratumoral inflammation induced by the injection of α-gal glycolipids, the treated tumors were resected at different time points after injection of the α-gal glycolipids, sectioned and stained with hematoxylin and eosin (H&E). Inflammatory cells were readily observed in peri-vascular regions of the tumors, within 4 days after α-gal glycolipids injection (See FIG. 12A). Although it is not necessary to understand the mechanism of an invention, it is believed that this inflammatory process resulted from complement activation due to an interaction between anti-Gal and α-gal glycolipids (See FIG. 3A). The inflammatory process further intensified and was much more extensive by day 14 (See FIG. 12B).

The morphology of the inflammation indicated the presence of mostly monocytes, macrophages, and neutrophils. Some of the tumors treated with α-gal glycolipids produced pro-inflammatory signals that ultimately induced extensive migration of lymphocytes into the treated tumor, to the extent of formation of organized lymphoid tissue structures (lymphoid nodules) on day 16. (See FIG. 12C). Such lymphoid nodules were previously reported to be induced by chemokines produced in inflammatory sites of autoimmune lesions. Such lesions generate chemotactic gradients recruiting dendritic cells, T cells, B cells, neutrophils, and monocytes into the site of inflammatory activity observed in the synovial membrane in rheumatoid arthritis patients (Cravens P D, Lipsky P E *Immunol Cell Biol.* 2002; 80: 497-505, and Page G, Lebecque S, Miossec P. *J. Immunol.* 2002; 168: 5333-41). No inflammatory reactions were observed within developing tumors in the absence of α-gal glycolipid such as the control tumors injected with PBS. These tumors contained no inflammatory cells further supporting the conclusion that an untreated tumor is "ignored" by the immune system and does not elicit an inflammatory reaction (See FIG. 12D).

Figure 12A:
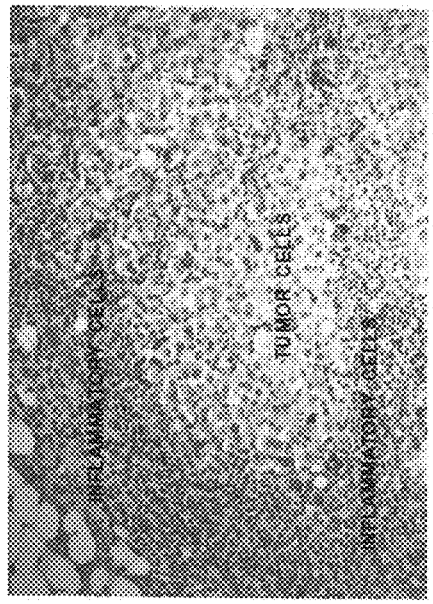
Figure 12B:
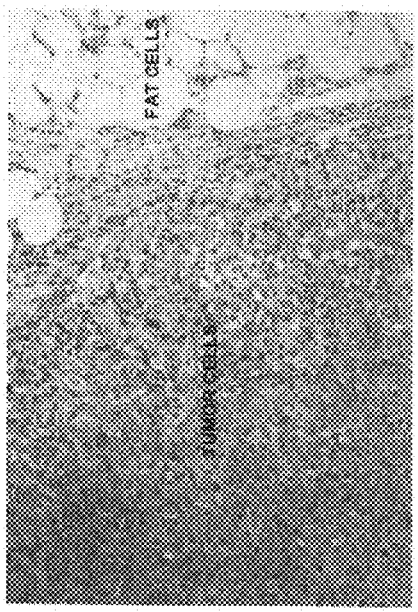
Figure 12C:
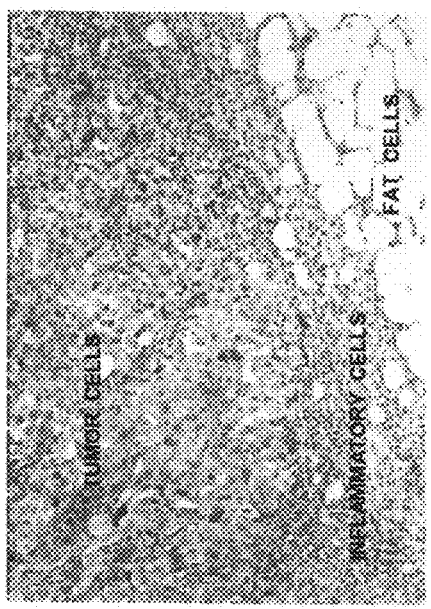
Figure 12D:
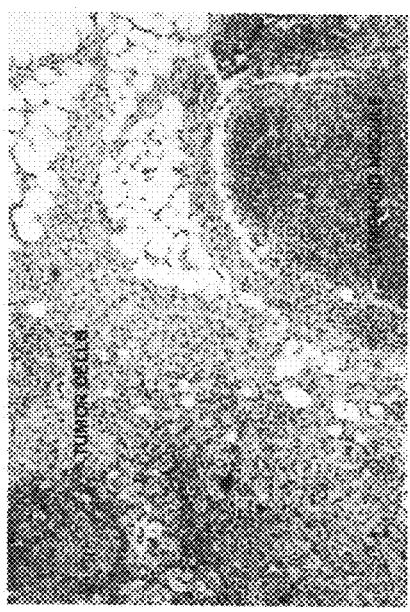

Lymphoid nodules observed within tumors injected with α-gal glycolipid further reflected a developing anti-tumor immune response (See FIG. 12C). A positive correlation has been suggested between intratumoral lymphoid infiltration, progression free survival, and overall survival in patients with solid tumors including, but not limited to, ovarian carcinoma (Zhang L, Conejo-Garcia J R, Katsaros D. et al. *N Engl J Med.* 2003; 348: 203-13), melanoma (Halpern A C, Schuchter L M. *Semin Oncol.* 1997; 24:S2-7), breast carcinoma (Marrogi A J, Munshi A, Merogi A J. et al, *Int J Cancer.* 1997; 74: 492-501), esophageal carcinoma (Schumacher K, Haensch W, Roefzaad C, Schlag P M *Cancer Res.* 2001; 61: 3932-36), colorectal carcinoma (Naito Y, Saito K, Shiiba K, et al. *Cancer Res.* 1998; 58: 3491), and renal cell carcinoma (Nakano O, Sato M, Naito Y, et al *Cancer Res.* 2001; 61: 5132-36). This correlation between the intratumoral lymphoid infiltration and cancer survival suggests that in patients displaying such infiltrates there is a protective immune response against micrometastases that are undetectable at the time of resection. Immune destruction of such metastases prevents relapse of the disease. Therefore, it is probable that infiltration of lymphocytes into solid tumors, following intratumoral injection α-gal glycolipids will have a similar outcome of induction of a protective immune response, thereby improving prognosis of the treated patient.

An intratumoral α-gal glycolipid injection was observed to progressively reduce the size of a treated tumor (i.e., for example, induction of a regression). (See FIG. 13). A fully developed cutaneous melanoma lesion is shown having protrusions and a fibrotic ring. (See FIG. 13A). Injection of α-gal glycolipids into the tumor mass results in gradual regression of the tumor after 5 days (See FIG. 13B). Finally, an almost complete elimination of the tumor tissue was observed within 15 days (See FIG. 13C).

It should be noted that a B16 melanoma tumor (as used in this experimental model) is an aggressive tumor that can double its size every 4-6 days as shown in PBS treated tumors (See FIG. 11C). The growth rate of human tumors are believed much slower, resulting in tumor doubling their size within a month to several months. Although it is not necessary to understand the mechanism of an invention, it is believed that intratumoral injection of α-gal glycolipids in humans is likely to be much more effective in preventing tumor development than that observed in the mouse with B16 melanoma, since the inflammatory response induced by this treatment can affect the slowly developing tumor lesion for prolonged periods. Moreover, because of this relatively slow tumor growth, α-gal glycolipids treatment can be delivered repeatedly into the human tumor lesions.

Example 6

Anti-Gal Mediated Phagocytosis of Tumor Cells by Antigen Presenting Cells

The conversion of a tumor lesion injected with α-gal glycolipids or with AdαGT, or with neuraminidase, α1,3galactosyltransferase, and uridine-diphosphate galactose into autologous tumor vaccines is based on the assumption that tumor cell membranes expressing α-gal epitopes and opsonized by the anti-Gal antibody will be taken up (phagocytized) effectively by antigen presenting cells such as macrophages and dendritic cells that migrate into the treated tumor lesion. The internalized tumor membranes may then be transported to the draining lymph nodes where the tumor antigen peptides are presented by the antigen presenting cells for activation of tumor specific T cells.

This phagocytosis was demonstrated with in vitro human lymphoma cells that were incubated with neuraminidase, α1,3galactosyltransferase, and uridine-diphosphate galactose (UDP-Gal) resulting in the synthesis of α-gal epitopes on these tumor cells (Galili U. *Cancer Immunology Immunotherapy* 2004; 53: 935-45, and Manches O, Plumas J, Lui L et al *Haematologica* 2005; 90: 625-34). Such an incubation resulted in synthesis of $1 \times 10^6$-$10 \times 10^6$ α-gal epitopes per cell. Binding of anti-Gal IgG molecules to these epitopes induced phagocytosis of the opsonized tumor cells by the antigen presenting cells. (See FIG. 14). The cells displayed α-gal epitopes and were then opsonized by anti-Gal IgG and effectively taken up by macrophages and/or dendritic cells (See FIGS. 14A & 14B, respectively).

It is believed that an in situ opsonization of tumor cells expressing α-gal epitopes in tumors injected with α-gal glycolipids, or in tumors injected with gene therapy vectors containing the α1,3galactosyltransferase gene, or in tumors injected with neuraminidase, α1,3galactosyltransferase, and uridine-diphosphate galactose will result in a similar anti-Gal antibody mediated targeting of tumor cells, or tumor cell membranes, to antigen presenting cells, thereby eliciting a protective anti-tumor immune response (i.e., for example, an autologous tumor vaccine).

Example 7

Demonstration of Increased Transport of Tumor Antigens by Antigen Presenting Cells from Tumors Treated with α-Gal Glycolipids to Draining Lymph Nodes In order to study the effect of α-gal glycolipids treatment on transport of tumor antigens from the treated tumor lesion to the draining lymph nodes a B 16 melanoma tumor was engineered to produce the protein chicken ovalbumin (OVA) as a surrogate tumor antigen (Lugade A A, Moran J P, Gerber S A, Rose R C, Frelinger J G, Lord E M. *J Immunol.* 2005; 174: 7516-23). These cells are referred to as B16/OVA cells.

KO mice were injected with one million B16/OVA cells subcutaneously into the right thigh. This results in the development of a tumor lesion having a 3-4 mm diameter within 8 days. These tumors were then injected with 1 mg α-gal glycolipids in a volume of 0.1 ml or with 0.1 ml of PBS as control. The injection was repeated after one week. Fourteen days after the first α-gal glycolipid injection, the transport of OVA by antigen presenting cells to the draining lymph nodes was evaluated.

The draining lymph nodes are the inguinal lymph nodes in the right thigh. The inguinal lymph nodes were removed from the right thigh which bears the tumor and cells were obtained from these lymph nodes. In parallel, cells were obtained from the inguinal lymph nodes of the left thigh that lacks the tumor.

To determine whether the lymph nodes from the two thighs contain antigen presenting cells that present OVA peptides as peptides of the surrogate tumor antigen, the cells from the lymph nodes were incubated in vitro at 37° C. with an equal number of B3Z cells. The B3Z cells are CD8+ T hybridoma cells expressing an α-β T cell receptor (TCR) that is specific for the immune dominant OVA peptide 257-264 ($OVA_{257-264}$ having the amino acid sequence SIINFEKL; SEQ ID NO:1) presented on MHC class I molecule $K^b$ (same as that on α1,3galactosyltransferase knockout mouse cells). The cells contain a reporter construct of the β-galactosidase lacZ gene, under the control of IL-2 regulatory elements (Karttunen J, Sanderson S, Shastri N. *Proc Natl Acad Sci USA.* 1992; 89: 6020-4). When the OVA-specific T cell receptor engages $OVA_{257-264}$ presented on class I MHC of antigen presenting cells from C57BL/6 mice or from α1,3galactosyltransferase knockout mice (KO) mice, these T hybridoma cells are activated resulting in activation of the lacZ gene, because this gene is under the IL-2 promoter. Therefore, following the binding of the T cell receptor to $OVA_{257-264}$ on antigen presenting cells, the B3Z cell is activated, resulting in activation of the IL-2 promoter and the subsequent activation of lacZ for the production of the enzyme β-galactosidase.

The B3Z cells were loaded by hypotonic shock with a substrate for β-galactosidase (fluorescein di-β-D galactopyranoside) which can be cleaved by this enzyme into fluorescein-galactoside detectable by flow cytometry. The B3Z cells were also immunostained with anti-CD8 antibodies coupled to phycoerythrin since these hybridoma T cells express the CD8+ cell marker (Karttunen J, Sanderson S, Shastri N. *Proc Natl Acad Sci USA.* 1992; 89: 6020-4).

The cells are gated in the flow cytometer for CD8+ cells (i.e. phycoerythrin positive cells) and measured for fluorescein (i.e. measuring α-galactosidase activation). If the draining lymph nodes contain antigen presenting cells that migrated from the tumor lesion and if these antigen presenting cells internalize B 16/OVA cells, then such cells would present $OVA_{257-264}$ and activate in vitro the B3Z cells. This activation was detected by fluorescein-galactoside light emission in the flow cytometer.

Data was obtained from α1,3galactsyltransferase knockout mice draining lymph nodes and opposite lymph nodes comparing α-gal glycolipid and PBS injected tumors (See FIG. 15A-C and FIG. 15D-F, respectively, showing a representative 3 out of 8 mice for each group). Lymph nodes from mice with tumors treated with PBS displayed very low numbers of $OVA_{257-264}$ antigen presenting cells, as indicated by the detection of only 0.0-0.14% of B3Z cells that were activated. In contrast, lymph node cells from mice with B16/OVA tumors injected with α-gal glycolipids displayed at least 10 fold higher activation of B3Z cells (1.07%-3.66% activated B3Z cells). In the 3 mice treated with glycolipids, cells from the lymph nodes of the tumor-free leg did not activate B3Z cells above background level. These findings support the conclusion that injection of tumor lesions with α-gal glycolipids resulted in an increased uptake and transport of the tumor antigens by antigen presenting cells to the lymph nodes, thereby converting the treated lesion into an in situ autologous tumor vaccine. (See FIG. 4)

Example 8

Increased Antibody Response to OVA in Mice with B16/OVA Tumor Injected with α-Gal Glycolipids One manifestation of an immune response to tumor antigens is the production of antibodies against these antigens (i.e., for example, a humoral response). This type of immune response was analyzed in α1,3galactosyltransferase knockout mice bearing B16/OVA tumor lesions that were injected either with α-gal glycolipids, or injected with PBS.

The mice were injected subcutaneously in the right flank with one million B16/OVA cells. After 8 days, the tumors reached a size of 4-5 mm and were injected with 1 mg α-gal glycolipid solution in a volume of 0.1 ml, or with 0.1 ml PBS. The injections were repeated once a week for two additional weeks. One week after the third injection (i.e. 3 weeks after the first injection) serum samples were obtained from the mice and analyzed for anti-OVA antibody production.

Anti-OVA antibody analysis was performed in ELISA wells coated overnight with OVA (20 µg/ml) and subsequently blocked with 1% bovine serum ovalbumin (BSA) in PBS.

The data showed that 9 out of 10 mice with tumors treated with PBS displayed no significant production of anti-OVA IgG antibodies (See FIG. 16). In contrast, most of the mice with B16/OVA tumors that were injected with α-gal glycolipids produced significant amounts of anti-OVA IgG antibodies. These findings imply that injection of α-gal glycolipids into tumor lesions converts the tumor into an effective vaccine, thus activiting OVA specific helper T cells that assist in antibody formation against the tumor antigens. These antibodies react against tumor antigens and together with tumor specific T cells contribute to the destruction of micrometastases that can not be identified visually or by imaging.

The data showing a lack of inflammatory response in PBS-injected tumors support the conclusion that most tumors remain "invisible" to the immune system and do not elicit a significant immune response against the tumor antigens within the tumor lesion. (See FIG. 12D).

Example 9

Increased T Cell Response to OVA Peptides in Mice with B16/OVA Tumor Injected with α-Gal Glycolipids One manifestation of the immune response to tumor lesions injected with α-gal glycolipids is a cellular immune response represented by generation of tumor specific T cells in the lymphoid organs. The ability of α-gal glycolipids treatment to elicit an anti-tumor T cell response was evaluated in α1,3galactosyltransferase knockout mice bearing subcutaneous B16/OVA tumors developed in accordance with Example 8.

These tumors received 3 intratumoral injections (once a week for three weeks) of 1 mg α-gal glycolipids or of PBS as control. The generation of primed T cells specific to OVA peptides was determined in the spleen of the mice by an ELISPOT assay measuring in vitro secretion of IFNγ as previously described (Lugade A A, Moran J P, Gerber S A, Rose R C, Frelinger J G, Lord E M. *J Immunol.* 2005; 174: 7516-23).

Spleen cells (splenocytes) from α1,3galactosyltransferase knockout mice injected with α-gal glycolipids or PBS were placed in Multiscreen Immobilon-P® plates (Millipore) at $2 \times 10^5$ splenocytes/well and coated with anti-mouse IFNγ for the detection of TH1 and CD8+ T cell activation. The immunodominant peptide $OVA_{257-264}$ (presented on claim I MHC molecules) or peptide $OVA_{323-339}$ (presented on class II MHC molecules) were added to the ELISPOT wells (in triplicate) at a final concentration of 5 µg/ml. The antigen presenting cells among the splenocytes (i.e. dendritic cells and macrophages) bind the peptides to their class I or class II MHC molecules, respectively, and present them to the corresponding OVA peptide specific T cells. After their T cell receptor engages the specific peptide, the T cells with these T cell receptors are activated and secrete IFNγ.

The plates with the cultured splenocytes were incubated for 24 h at 37° C. Subsequently, the wells were washed, and the anti-IFNγ detector antibody coupled with horseradish peroxidase (HRP) was added for analysis of IFNγ production. This was followed by a color reaction that detected spots reflecting the location of individual T cells secreting IFNγ. Control wells contained no peptides and represented spontaneous background secretion of the cytokine.

The number of T cells activated by each of the two peptides to secrete IFNγ was calculated as the number of spots per $10^6$ splenocytes after subtraction of the number of spots in the corresponding control wells lacking OVA peptides. Activation of T cells by each of the peptides was considered significant if at least 50 spots per $10^6$ splenocytes were counted in the individual mouse.

The data show that only 2 out of the 8 mice with PBS treated tumors were significantly activated by the class I MHC presented peptide $OVA_{257-264}$, or by the class II MHC presented peptide $OVA_{323-339}$. (See FIG. 17). In contrast, 9 out of the 10 mice with α-gal glycolipid treated tumors were significantly activated by each of these two peptides. These data imply that intratumoral injection of α-gal glycolipids resulted in an increased activation of tumor specific T cells by tumor antigen peptides.

Taken together, the data in Examples 7, 8, and 9 support the conclusion that intratumoral injection of α-gal glycolipids results in the conversion of the tumor into an autologous tumor vaccine in which the tumor antigens are taken up effectively by antigen presenting cells and transported to the lymphoid organs where they are presented as tumor antigen peptides that elicit humoral and cellular anti-tumor immune responses.

In one embodiment, the present invention contemplates that a patient treated with an intratumoral injection of α-gal glycolipids capable of inducing an immune response against tumor antigens will reduce the growth rate, induce regression, and/or develop an antitumor immune response that destroys undetectable micrometastases expressing the tumor antigens.

Example 10

Expression of α-Gal Epitopes on B16-BL6 Melanoma Cells Transduced with Adenovirus Vector Containing the α1,3Galalctosyltransferase Gene The α1,3galalctosyltransferase gene may be introduced into cells by insertion into a replication incompetent adenovirus vector. (Deriy L, Chen Z C, Gao, G P, Galili, U, *Glycobiology* 2002, 12: 135). The resulting vector was designated AdαGT and is very effective in inducing expression of α-gal epitopes on human tumor cells (Deriy L, Chen Z C, Gao, G P, Galili, U, *Glycobiology* 2002, 12: 135).

The expression of α-gal epitopes was determined on AdαGT transduced B 16-BL6 melanoma cells. These cells are a subclone of B 16 melanoma and are referred to as BL6 cells. The transduction of BL6 cells with AdαGT results in intracellular production of α1,3galactosyltransferase that is encoded by the a 1,3galactosyltransferase gene within the transducing AdαGT. The de novo expression of α-gal epitopes on cell surface glycoconjugates following synthesis of this epitope by the α1,3galactosyltransferase was evaluated 48 hour post transduction.

α-Gal epitopes were detected by the binding of *Bandeiraea (Griffonia) simplicifolia* IB4 lectin (BS lectin—a lectin specific to α-gal epitopes) and by the binding of the anti-Gal antibody to the transduced cells. BL6 cells transduced with AdαGT (referred to as $BL6_{AdαGT}$ cells) displayed a significant shift following BS lectin binding, as measured by flow cytometry, in comparison to BL6 cells transduced with the control "empty" adenovirus that lacks the α1,3galactosyltransferase gene insert (referred to as $BL6_{Adcont}$ cells) (See FIG. 18A). In addition, ~15% of the $BL6_{AdαGT}$ cells displayed a much higher degree of lectin binding than the rest of the population, indicating that these cells express α-gal epitopes in high numbers of epitopes per cell.

The ability of mouse anti-Gal IgG to bind to the α-gal epitopes on BL6$_{AdαGT}$ cells was demonstrated by ELISA. (See FIG. 18B). The BL6$_{cont}$ cells or BL6$_{AdαGT}$ cells were attached to ELISA wells by drying. Subsequently, serum containing anti-Gal IgG was added at serial twofold dilutions to the wells and anti-Gal IgG binding determined by the binding of horseradish peroxidase (HRP) conjugated goat anti-mouse IgG antibody. Nonspecific IgG binding values were subtracted by parallel measurement of IgG binding to wells coated with non-transduced BL6 cells. Anti-Gal readily bound to BL6$_{AdαGT}$ cells even at serum dilution of 1:128, whereas no binding was observed in wells coated with BL6$_{Adcont}$ cells in any of the serum dilutions (See FIG. 18B).

Example 11

Efficacy of BL6$_{AdαGT}$ Cells in Eliciting a Protective Anti-Tumor Immune Response The efficacy of AdαGT transduced tumor cells as vaccines was studied in α1,3galactosyltransferase knockout mice. The B16-BL6 cells served as the tumor model.

Anti-Gal antibody producing mice were vaccinated with 2×10$^6$ irradiated BL6$_{AdαGT}$ cells, or with 2×10$^6$ irradiated BL6 cells that were transduced with the control parental adenovirus vector lacking the α1,3galactosyltransferase gene. The latter cells, referred to as BL6$_{Adcont}$, did not express α-gal epitopes and served for immunization of the control mice. The immunization was repeated after one week.

Figure 19B:
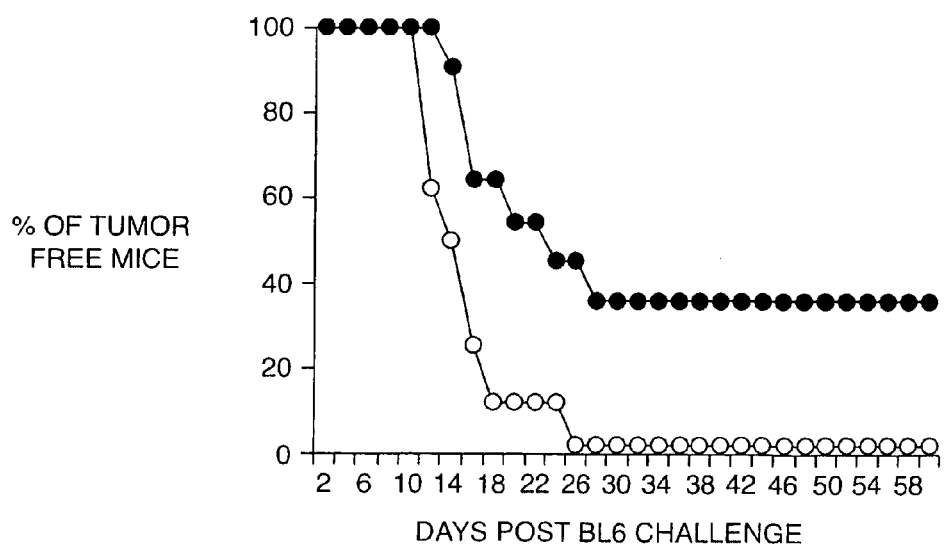

One week after the second immunization, the mice were challenged subcutaneously with 0.2×10$^6$ or 0.5×10$^6$ live BL6 cells. Tumor development was monitored for 2 months. Two thirds of the mice immunized with BL6$_{AdαGT}$ cells and challenged with 0.2×10$^6$ nontransduced parental BL6 cells were protected against the challenge, whereas only 20% of the control group did not develop tumors. (See FIG. 19A). When the mice were challenged with the higher dose of 0.5×10$^6$ live BL6 cells, one third of the mice immunized with BL6$_{AdαGT}$ cells developed protection against the tumor challenge, whereas all control mice vaccinated with BL6 cells transduced with the control virus Ad$_{cont}$, developed tumors within 25 days post challenge with BL6 cells. (FIG. 19B).

These results support the conclusion that AdαGT transduced tumor cells expressing α-gal epitopes can serve as tumor vaccines that are effectively targeted to antigen presenting cells and thus can induce an immune response against the same tumor cells which lack α-gal epitopes. The invention uses the same principle of converting tumor cells into vaccines by in vivo transduction of tumor cells with AdαGT, or with any other vector containing the α1,3galactosyl-transferase gene.

Example 12

Regression and/or Destruction of Tumor Lesions by Intratumoral Injection of AdαGT The present example demonstrates the regression and/or destruction of a tumor lesion following the intratumoral injection of AdαGT. (See FIG. 11A).

α1,3galactosyltransferase knockout mice were shaven and injected with 1×10$^6$ subcutaneously with B16 melanoma cells at two sites in the same flank. On day 8, when the tumors reached a diameter of 4-5 mm a first tumor was injected with 10$^9$ infectious units (IU) of AdαGT in 0.1 ml phosphate buffer saline (PBS) and a second tumor is injected with 0.1 ml Ad$_{cont}$ serving as a control. After 72 h, the de novo α-gal epitopes were readily detectable within the treated tumors by staining with fluorescent *Bandeiraea simplicifolia* IB4 (BS lectin) (See FIG. 20A).

Figure 20B:
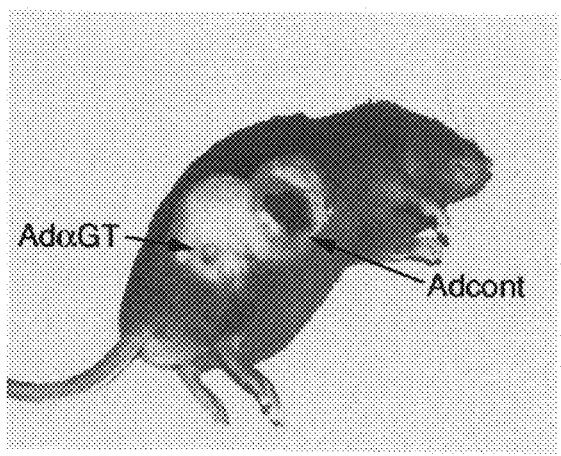
Figure 20C:
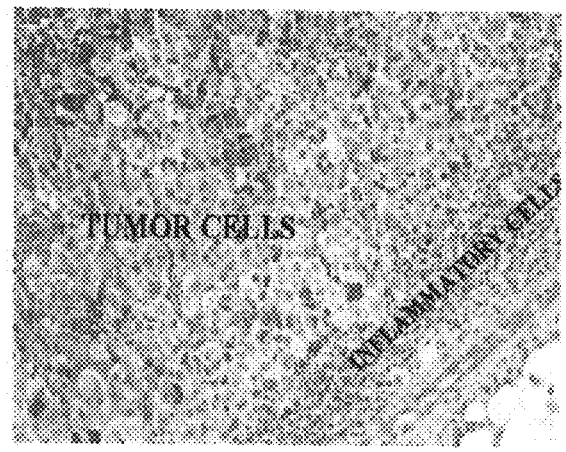

Ten days post injection, many of the tumors injected with AdαGT stopped growing or showed a 50% decrease in size (i.e., regression). A representative mouse (one of four with similar results) with tumors injected with Ad$_{cont}$ or with AdαGT (front and back tumors, respectively) is shown in FIG. 20B. Tumor growth inhibition is clearly associated with an inflammatory reaction within the AdαGT treated tumors (See FIG. 20C). Thus, intratumoral injection of AdαGT induces inflammation and tumor regression as a result of anti-Gal binding to α-gal epitopes de novo expressed on transduced tumor cells.

Example 13

Synthesis of α-Gal Epitopes on Human Tumor Cells by α1,3 Galactosyltransferase and Neuramimidase This example describes the in vitro enzymatic synthesis of α-gal epitopes within human tumor cells using recombinant α1,3galactosyltransferase and neuraminidase. These two enzymes can synthesize α-gal epitopes on N-linked carbohydrate chains of tumor cells as outlined in a two step reaction (See FIG. 21A):

1. The terminal sialic acid (SA) is removed from the carbohydrate chains by the activity of neuraminidase, and
2. The α1,3galactosyltransferase links terminal α-galactosyl units in an α1-3 linkage to the galactose (Gal) of the N-acetyllactosamine (Galβ1-4GlcNAc-R or Galβ1-3GlacNAc-R) to generate the α-gal epitopes. The sugar donor for the galactose is uridine diphosphate galactose (UDP-Gal).

In the absence of sialic acid on the carbohydrate chains, the synthesis of α-gal epitopes is believed not to require neuraminidase.

This de novo synthesis of α-gal epitopes can also be achieved with cell surface glycolipids. Recombinant α1,3galactosyltransferase was produced in the expression system of yeast *Pichia pastoris* transformed by an α1,3galactosyltransferase gene (Chen Z C, Tanemura M, Galili U. *Glycobiology*. 2001; 11: 577-86).

The present example shows α-gal epitope synthesis on human tumor cells. (See FIG. 21B). Leukemia cells were obtained from a chronic lymphocytic leukemia patient and incubated as 5×10$^6$ cells/ml for 2 h at 37° C. in MES buffer containing 25 mM MnCl$_2$ and 2 mM UDP-Gal. The cell were incubated in: i) the absence of enzymes; ii) only 30 µg/ml recombinant α1,3galactosyltransferase; or iii) both 1 mM neuraminidase and 30 µg/ml recombinant α1,3galactosyltransferase. At the end of incubation, the cells were washed and attached by drying in ELISA wells as 10×10$^6$ cells/ml. After blocking the wells with 1% bovine serum albumin (BSA) in PBS, the binding of the mouse monoclonal anti-Gal antibody M86 to the cells displaying de novo synthesized α-gal epitopes was determined using peroxidase coupled goat anti-mouse IgM antibodies as secondary antibody and color reaction developed with o-phenylene diamine (OPD).

The data was calculated using optical density (OD) units after subtraction of nonspecific binding of the antibodies to untreated leukemia cells. No α-gal epitopes were expressed on the untreated human leukemia cells, or on these cells incubated only with α1,3galactosyltranferase. (See FIG. 21B). Although it is not necessary to understand the mechanism of an invention, it is believed that no α-gal epitopes were synthesized because N-acetyllacosamines on carbohydrate chains are capped by carbohydrate chains and thus are not accessible to α1,3galactosyltransferase. However, cells that were incubated with neuraminidase and α1,3galactosyltransferase expressed numerous α-gal epitopes and thus, readily bind the anti-Gal antibody.

A similar synthesis of α-gal epitopes on tumor cells would be expected to occur in vivo in tumor lesions that are intratumorally injected with α1,3galactosyltransferase, neuraminidase and UDP-Gal. α-Gal epitope display resulting from this de novo synthesis would also be expected to induce anti-Gal antibody mediated phagocytosis by antigen presenting cells in a similar manner as for human lymphoma cells (See FIG. 14).

I claim:

1. A method for introducing a glycolipid into a solid tumor in a human subject, comprising:
   a) providing
      i) a human subject comprising at least one solid tumor that comprises a plurality of cancer cells having a cell surface; and
      ii) a glycolipid having a non-reducing end that comprises an α-gal epitope comprising Galactosyl α1-3Galactosyl (Galα1-3Gal); and
   b) introducing said glycolipid into at least one said solid tumor to create a solid tumor displaying said α-galactosyl epitope on its said cell surface.

2. The method of claim 1, wherein said introducing comprises a procedure selected from the group consisting of intradermal injection, transcutaneous imaging guided injection, endoscopic injection, bronchoscopic injection, cytoscopic injection, colonoscopic injection, and laparoscopic injection.

3. The method of claim 1, wherein said solid tumor is a tumor originating from an organ selected from the group consisting of peritoneum, liver, pancreas, lung, urinary bladder, prostate, uterus, cervix, vagina, breast, skin, brain, lymph node, head and neck, stomach, intestine, colon, and ovaries.

4. The method of claim 1, wherein said subject was treated previously to surgically remove said tumor.

5. The method of claim 1, wherein said subject was not previously treated to remove said tumor.

6. The method of claim 1, wherein said tumor comprises a primary tumor.

7. The method of claim 1, wherein said glycolipid is derived from a nonprimate mammalian cell.

8. The method of claim 1, wherein said tumor comprises melanoma cells.

9. The method of claim 8, wherein said introducing comprises a topical application.

10. The method of claim 1, further comprising wherein said solid tumor displaying said [alpha]-galactosyl epitope undergoes regression, wherein said solid tumor is selected from the group consisting of a melanoma and a liver metastasis.

11. The method of claim 1, further comprising wherein said solid tumor displaying an alpha-galactosyl epitope is destroyed, wherein said solid tumor is selected from the group consisting of a melanoma and a liver metastasis.

12. The method of claim 1, wherein said glycolipid comprises a lipid selected from the group consisting of fatty acid, sphingosine, and ceramide.

13. The method of claim 1, wherein said glycolipid comprises a saccharide selected from the group consisting of α1-3 Galactobiose (Galα1-3Gal), α1-3, β1-4 Galactotriose (Galα1-3Galβ1-4Gal), and Galili pentasaccharide (Galα1-3Galβ1-4GlcNAcβ1-3Galβ1-4G1c).

14. The method of claim 7, wherein said nonprimate mammalian cell comprises a rabbit red blood cell.

15. The method of claim 7, wherein said nonprimate mammalian cell comprises a bovine red blood cell.

16. The method of claim 1, wherein said tumor comprises carcinoma cells.

17. The method of claim 1, wherein said tumor comprises a metastasis.

18. The method of claim 1, wherein said introducing further comprises regression of a second tumor in said subject, wherein said second tumor is selected from the group consisting of a melanoma and a liver metastasis.

19. The method of claim 1, wherein said introducing further comprises destruction of a second tumor in said subject, wherein said second tumor is selected from the group consisting of a melanoma and a liver metastasis.

20. The method of claim 1, wherein said tumor comprises leukemia cells.

21. A method of introducing a glycolipid into a solid tumor in a mouse, comprising:
   a) providing;
      i) a mouse
         1) lacking an α1,3 galactosyltransferase gene,
         2) having anti-Gal antibodies, and
         3) comprising at least one solid tumor comprising a plurality of cancer cells having a cell surface; and
      ii) a glycolipid having a non-reducing end that comprises an α-galactosyl epitope comprising Galactosylα1-3Galactosyl (Galα1-3Gal); and
   b) introducing said glycolipid into at least one said solid tumor to create a solid tumor displaying said a-galactosyl epitope on said cell surface.

22. The method of claim 21, wherein said solid tumor is a tumor originating from an organ selected from the group consisting of peritoneum, liver, pancreas, lung, urinary bladder, prostate, uterus, cervix, vagina, breast, skin, brain, lymph node, head and neck, stomach, intestine, colon, and ovaries.

23. The method of claim 21, wherein said mouse was treated previously to surgically remove said tumor.

24. The method of claim 21, wherein said mouse was not previously treated to remove said tumor.

25. The method of claim 21, wherein said tumor comprises a primary tumor.

26. The method of claim 21, wherein said glycolipid is derived from a nonprimate mammalian cell.

27. The method of claim 21, wherein said tumor comprises melanoma cells.

28. The method of claim 27, wherein said introducing comprises a topical application.

29. The method of claim 21, further comprising wherein said solid tumor displaying said [alpha]-galactosyl epitope undergoes regression, wherein said solid tumor is selected from the group consisting of a melanoma and a liver metastasis.

30. The method of claim 21, further comprising wherein said solid tumor displaying an [alpha]-galactosyl epitope is destroyed, wherein said solid tumor is selected from the group consisting of a melanoma and a liver metastasis.

31. The method of claim 21, wherein said glycolipid comprises a lipid selected from the group consisting of fatty acid, sphingosine, and ceramide.

32. The method of claim 21, wherein said glycolipid comprises a saccharide selected from the group consisting of α1-3 Galactobiose (Galα1-3Gal), α1-3, β1-4 Galactotriose (Galβ1-3Galβ1-4Gal), and Galili pentasaccharide (Galα1-3Gal1-4GlcNAcβ1-Galβ1-4Glc).

33. The method of claim 26, wherein said nonprimate mammalian cell comprises a rabbit red blood cell.

34. The method of claim 6 wherein said nonprimate mammalian cell comprises a bovine red blood cell.

35. The method of claim 1, wherein said tumor comprises carcinoma cells.

36. The method of claim 1, wherein said tumor comprises leukemia cells.

37. The method of claim 1, wherein said tumor comprises a metastasis.

38. The method of claim 21, wherein said introducing further comprises regression of a second tumor in said mouse, wherein said second tumor is selected from the group consisting of a melanoma and a liver metastasis.

39. The method of claim 21, wherein said introducing further comprises destruction of a second tumor in said mouse, wherein said second tumor is selected from the group consisting of a melanoma and a liver metastasis.

40. The method of claim 21, wherein said introducing comprises a procedure selected from the group consisting of intradermal injection, transcutaneous imaging guided injection, endoscopic injection, bronchoscopic injection, cytoscopic injection, colonoscopic injection, and laparoscopic injection.

* * * * *

```
                         SEQUENCE LISTING

<160> NUMBER OF SEQ ID NOS: 4

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
1               5

<210> SEQ ID NO 2
<211> LENGTH: 1140
<212> TYPE: DNA
<213> ORGANISM: Callithrix jacchus

<400> SEQUENCE: 2
gagaaaataa tgaatgtcaa aggaaaagta attctgtcga tgctggttgt ctcaactgtg     60
attgttgtgt tttgggaata tatcaacagc ccagaaggct ctttcttgtg gatatatcac    120
tcaaagaacc cagaagttga tgacagcagt gctcagaagg actggtggtt tcctggctgg    180
tttaacaatg ggatccacaa ttatcaacaa gaggaagaag acacagacaa agaaaaagga    240
agagaggagg aacaaaaaaa ggaagatgac acaacagagc ttcggctatg ggactggttt    300
aatccaaaga aacgcccaga ggttatgaca gtgacccaat ggaaggcgcc ggttgtgtgg    360
gaaggcactt acaacaaagc catcctagaa aattattatg ccaaacagaa aattaccgtg    420
gggttgacgg ttttttgctat tggaagatat attgagcatt acttggagga gttcgtaaca    480
tctgctaata ggtacttcat ggtcggccac aaagtcatat tttatgtcat ggtggatgat    540
gtctccaagg cgccgtttat agagctgggt cctctgcgtt ccttcaaagt gtttgaggtc    600
aagccagaga agaggtggca agacatcagc atgatgcgta tgaagaccat cggggagcac    660
atcttggccc acatccaaca cgaggttgac ttcctcttct gcatggatgt ggaccaggtc    720
ttccaagacc attttggggt agagaccctg ggccagtcgg tggctcagct acaggcctgg    780
tggtacaagg cagatcctga tgactttacc tatgagaggc ggaaagagtc ggcagcatat    840
attccatttg gccaggggga tttttattac catgcagcca tttttggagg aacaccgatt    900
caggttctca acatcaccca ggagtgcttt aagggaatcc tcctggacaa gaaaaatgac    960
atagaagccg agtggcatga tgaaagccac ctaaacaagt atttccttct caacaaaccc   1020
tctaaaatct tatctccaga atactgctgg gattatcata taggcctgcc ttcagatatt   1080
aaaactgtca agctatcatg gcaaacaaaa gagtataatt tggttagaaa gaatgtctga   1140

<210> SEQ ID NO 3
<211> LENGTH: 376
<212> TYPE: PRT
<213> ORGANISM: Callithrix jacchus

<400> SEQUENCE: 3

Met Asn Val Lys Gly Lys Val Ile Leu Ser Met Leu Val Val Ser Thr
```

```
              1               5              10              15
Val Ile Val Val Phe Trp Glu Tyr Ile Asn Ser Pro Glu Gly Ser Phe
                     20                  25                  30

Leu Trp Ile Tyr His Ser Lys Asn Pro Glu Val Asp Asp Ser Ser Ala
             35                  40                  45

Gln Lys Asp Trp Trp Phe Pro Gly Trp Phe Asn Asn Gly Ile His Asn
         50                  55                  60

Tyr Gln Gln Glu Glu Glu Asp Thr Asp Lys Glu Lys Gly Arg Glu Glu
 65                  70                  75                  80

Glu Gln Lys Lys Glu Asp Asp Thr Thr Glu Leu Arg Leu Trp Asp Trp
                 85                  90                  95

Phe Asn Pro Lys Lys Arg Pro Glu Val Met Thr Val Thr Gln Trp Lys
             100                 105                 110

Ala Pro Val Val Trp Glu Gly Thr Tyr Asn Lys Ala Ile Leu Glu Asn
             115                 120                 125

Tyr Tyr Ala Lys Gln Lys Ile Thr Val Gly Leu Thr Val Phe Ala Ile
130                 135                 140

Gly Arg Tyr Ile Glu His Tyr Leu Glu Glu Phe Val Thr Ser Ala Asn
145                 150                 155                 160

Arg Tyr Phe Met Val Gly His Lys Val Ile Phe Tyr Val Met Val Asp
                 165                 170                 175

Asp Val Ser Lys Ala Pro Phe Ile Glu Leu Gly Pro Leu Arg Ser Phe
                 180                 185                 190

Lys Val Phe Glu Val Lys Pro Glu Lys Arg Trp Gln Asp Ile Ser Met
                 195                 200                 205

Met Arg Met Lys Thr Ile Gly Glu His Ile Leu Ala His Ile Gln His
210                 215                 220

Glu Val Asp Phe Leu Phe Cys Met Asp Val Asp Gln Val Phe Gln Asp
225                 230                 235                 240

His Phe Gly Val Glu Thr Leu Gly Gln Ser Val Ala Gln Leu Gln Ala
                 245                 250                 255

Trp Trp Tyr Lys Ala Asp Pro Asp Asp Phe Thr Tyr Glu Arg Arg Lys
             260                 265                 270

Glu Ser Ala Ala Tyr Ile Pro Phe Gly Gln Gly Asp Phe Tyr Tyr His
             275                 280                 285

Ala Ala Ile Phe Gly Gly Thr Pro Ile Gln Val Leu Asn Ile Thr Gln
         290                 295                 300

Glu Cys Phe Lys Gly Ile Leu Leu Asp Lys Lys Asn Asp Ile Glu Ala
305                 310                 315                 320

Glu Trp His Asp Glu Ser His Leu Asn Lys Tyr Phe Leu Leu Asn Lys
                 325                 330                 335

Pro Ser Lys Ile Leu Ser Pro Glu Tyr Cys Trp Asp Tyr His Ile Gly
             340                 345                 350

Leu Pro Ser Asp Ile Lys Thr Val Lys Leu Ser Trp Gln Thr Lys Glu
         355                 360                 365

Tyr Asn Leu Val Arg Lys Asn Val
370                 375

<210> SEQ ID NO 4
<211> LENGTH: 1131
<212> TYPE: DNA
<213> ORGANISM: Mus musculus

<400> SEQUENCE: 4
```

-continued

```
atgaatgtca agggaaaagt gatcctgttg atgctgattg tctcaaccgt ggttgtcgtg    60 tttttgggaat atgtcaacag cccagacggc tctttcttgt ggatatatca cacaaaaatt  120
ccagaggttg gtgagaacag atggcagaag gactggtggt tcccaagctg gttttaaaaat 180 gggacccaca gttatcaaga agacaacgta gaaggacgga gagaaaaggg tagaaatgga  240
gatcgcattg aggaagatga cacaacagag cctcagctat gggactggtt caatccaaag  300
aaccgcccgg atgttttgac agtgaccccg tggaaggcgc cgattgtgtg ggaaggcact  360
tatgacacag ctctgctgga aaagtactac gccacacaga aactcactgt ggggctgaca  420
gtgtttgctg tgggaaagta cattgagcat tacttagaag actttctgga gtctgctgac  480
atgtacttca tggttggcca tcgggtcata ttttacgtca tgatagacga cacctcccgg  540
atgcctgtcg tgcacctgaa ccctctacat tccttacaag tctttgagat caggtctgag  600
aagaggtggc aggatatcag catgatgcgc atgaagacca ttggggagca catcctggcc  660
cacatccagc acgaggtcga cttcctcttc tgcatggacg tggatcaagt ctttcaagac  720
aacttcgggg tggaaactct gggccagctg gtagcacagc tccaggcctg gtggtacaag  780
gccagtcccg agaacttcac ctatgagagg cgggaactgt cggccgcgta cattccattc  840
ggagaggggg atttttacta ccacgcggcc attttttggag gaacgcctac tcacattctc  900
aacctcacca gggagtgctt taaggggatc ctccaggaca agaaacatga catagaagcc  960
cagtggcatg atgagagcca cctcaacaaa tacttccttt tcaacaaacc cactaaaatc 1020
ctatctccag agtattgctg ggactatcag ataggcctgc cttcagatat taaaagtgtc 1080
aaggtagctt ggcagacaaa agagtataat ttggttagaa ataatgtctg a          1131
```